US007364739B2

(12) United States Patent
Richards et al.

(10) Patent No.: US 7,364,739 B2
(45) Date of Patent: Apr. 29, 2008

(54) HAEMOPHILUS INFLUENZAE LIPOPOLYSACCHARIDE INNER-CORE OLIGOSACCHARIDE EPITOPES AS VACCINES FOR THE PREVENTION OF HAEMOPHILUS INFLUENZAE INFECTIONS

(75) Inventors: James C. Richards, Ottawa (CA); Andrew Cox, Gloucester (CA); Richard Moxon, Oxford (GB); Derek Hood, Oxford (GB); Elke K. H. Schweda, Atlasvagan 16, S-131 34, Naka (SE); Martin Månsson, Grondalsvagen 60, S-151 65, Sodertalje (SE)

(73) Assignees: National Research Council of Canada, Ottawa (CA); The Chancellor, Masters, and Scholars of the University of Oxford, Oxford (GB); Elke K. H. Schweda, Naka (SE); Martin Månsson, Sodertalje (SE)

( * ) Notice: Subject to any disclaimer, the term of this patent is extended or adjusted under 35 U.S.C. 154(b) by 327 days.

(21) Appl. No.: 10/362,458

(22) PCT Filed: Aug. 27, 2001

(86) PCT No.: PCT/CA01/01225

§ 371 (c)(1),
(2), (4) Date: Nov. 1, 2004

(87) PCT Pub. No.: WO02/16440

PCT Pub. Date: Feb. 28, 2002

(65) Prior Publication Data

US 2005/0153057 A1    Jul. 14, 2005

Related U.S. Application Data

(60) Provisional application No. 60/227,850, filed on Aug. 25, 2000.

(51) Int. Cl.
*A61K 39/00* (2006.01)
(52) U.S. Cl. .................................. 424/184.1
(58) Field of Classification Search .............. 424/184.1
See application file for complete search history.

(56) References Cited

U.S. PATENT DOCUMENTS

| 5,057,546 | A |   | 10/1991 | Sudan ..................... 521/107 |
| 5,153,312 | A |   | 10/1992 | Porro ..................... 530/405 |
| 5,204,098 | A |   | 4/1993 | Szu et al. .................... 424/92 |
| 5,283,185 | A |   | 2/1994 | Epand et al. ............. 435/172.3 |
| 5,527,928 | A |   | 6/1996 | Nantz et al. ................ 554/105 |
| 6,207,157 | B1 |   | 3/2001 | Gu et al. ................. 424/184.1 |
| 6,248,329 | B1 | * | 6/2001 | Chandrashekar et al. 424/184.1 |

FOREIGN PATENT DOCUMENTS

DE    198 44 191 A1    3/2000

| EP | 0941738 | 9/1999 |
| WO | 8806626 | 9/1988 |
| WO | 9000594 | 1/1990 |
| WO | 9113157 | 9/1991 |
| WO | 9201796 | 2/1992 |
| WO | 9211361 | 7/1992 |
| WO | 9221376 | 12/1992 |
| WO | 9416737 | 8/1994 |
| WO | 9517211 | 6/1995 |
| WO | 9534323 | 12/1995 |
| WO | 9606627 | 3/1996 |
| WO | WO 00/70060 | 11/2000 |

OTHER PUBLICATIONS

Phillips et al. Characterization of two transposon mutants from Haemophilus influenzae Type b with altered Lipooligosaccharid Biosynthesis. Biochemistry. 1996, 35, 5937-5947.*
Kahler et al 2005 Glycobiology vol. 15 No. 4 pp. 409-419.*
Greenspan et al. (Nature Biotechnology 7: 936-937, 1999).*
Bowie et al (Science, 1990, 247:1306-1310).*
Ellis (Chapter 29 of Vaccines, Plotkin, et al. (eds) WB Saunders, Philadelphia, 1988, especially p. 571, paragraph 2).*
Cripps et al Current Opinion in Immunology 2002, 14 pp. 553-557.*
Alexander et al., "Determination of Inherited Traits of H. Influenzae by desoxyribonucleic acid fractions isolated from Type-Specific Cells", *J. Exp. Med.*, 93:345-359, 1951.
Allen et al., "Identification and Cloning of waaF (rfaF) from *Bordetella pertussis* and Use to Generate Mutants of *Bordetella* spp. With Deep Rough Lipopolysaccharide", *J. Bacteriol.*, 180:35-40, 1998.
Barenkamp et al., "Development of serum bactericidal activity following nontypable *Haemophilus influenzae* acute otitis media", (Pediatr. Infect. Dis. J., 9:333-339, 1990).
Black et al., "ADP-Ribosyltransferase Activity of Pertussis Toxin Immunomodulation by *Bordetella pertussis*", Science, 240:656-659, 1988.

(Continued)

Primary Examiner—Mark Navarro
Assistant Examiner—Nina A. Archie

(57) ABSTRACT

The present invention relates to a lipopolysaccharide moiety comprising a conserved triheptosyl inner-core moiety of lipopolysaccharide substantially free of variable outer core oligosaccharide chain extension, and to vaccines obtaines therefrom which are cross-reactive for *Haemophilus influenzae* strains. The invention also relates to defined mutations in the biosynthetic machinery for lipopolysaccharide (LPS;) expression in *Haemophilus influenzae* useful to obtain the abovementioned moiety. The invention also relates to using conjugates of the LPS from the mutant strains so obtained to elicit a heterologous immune response against a wide range of disease-causing *H. influenzae* strains. More specifically, the invention relates to vaccines for prevention of bacterial infections comprising core lipopolysaccharide of *Haemophilus influenzae*.

16 Claims, 17 Drawing Sheets

OTHER PUBLICATIONS

Blakeney et al, "Methylation of carbohydrates with lithium methylsulphinyl carbanion", Carbohydr. Res., 140:319-324, 1985.

Brooke et al., "Molecular Cloning of the *Haemophilus influenzae gmhA* (*IpcA*) Gene Encoding a Phosphoheptose Isomerase Required for Lipooligosaccharide Biosynthesis", J. Bacteriol., 178:3339-3341, 1996.

Campagnari et al., "Antigenic Diversity of Lipooligosaccharides of Nontypable *Haemophilus influenzae*", (Infect. Immun., 55:882-887, 1987).

Fleischmann et al., "Whole-Genome Random Sequencing and Assembly of *Haemophilus influenzae*Rd", Science, 269:496-512, 1995.

Flynn J.L., "Review Recombinant BCG As An Antigen Delivery System", Cell. Mol. Biol., 40(suppl. I):31-36, 1994.

Gibson et al., "Investigation of the Structural Heterogeneity of Lipooligosaccharides from Pathogenic *Haemophilus* and *Neisseria* Species and of R-Type Lipopolysaccharides from *Salmonella typhimurium* by Electrospray Mass Spectrometry", J. Bacteriol., 175:2702-2712, 1993.

Gotschlich, E.C., "Genetic Locus for the Biosynthesis of the Variable Portion of *Neisseria gonorrhoeae* Lipooligosaccharide", J. Exp. Med., 180:2181-2190, 1994.

Gu et al., "Synthesis, Characterization, and Immunologic Properties of Detoxified Lipooligosaccharide from Nontypeable *Haemophilus influenzae* Conjugated to Proteins", Infect. Immun., 64:4047-4053, 1996.

Helander et al., "Chemical structure of the lipopolysaccharide of *Haemophilus influenzae* strain I-69 RD$^-$/b$^+$ Description of a novel deep-rough chemotype", Eur. J. Biochem., 177:483-492, 1988.

Herriott et al., "Defined Nongrowth Media for Stage II Development of Competence in *Haemophilus influenzae* ", J. Bacteriol., 101:517-524, 1970.

High et al., "The role of a repetitive DNA motif,(5'-CAAT-3') in the variable expression of the *Haemophilus influenzae* lipopolysaccharide epitope αGal(1-4)βGal", Mol. Microbiol., 9:1275-1282, 1993.

Holst et al., "Structural analysis of two oligosaccharide bisphosphates isolated from the lipopolysaccharide of a recombinant strain of *Escherichia coli* F515 (Re chemotype) expressing the genus-specific epitope of *Chlamydia* lipopolysaccharide", Eur. J. Biochem., 214:703-710, 1993.

Hood et al., "DNA repeats identify novel virulence genes in *Haemophilus influenzae*", Proc. Natl. Acad. Sci. USA, 93:11121-11125, 1996.

Hood et al., "Use of the complete genome sequence information of *Haemophilus influenzae* strain Rd to investigate lipopolysaccharide biosynthesis", Mol. Microbiol., 22:951-965, 1996.

Hood et al., "Sialic acid in the lipopolysaccharide of *Haemophilus influenzae*: strain distribution, influence on serum resistance and structural characterization", Mol. Microbiol., 33:679-692, 1999.

Hood et al., "Identification of a lipopolysaccharide α-2,3-sialytransferase from *Haemophilus influenzae*", Mol. Microbiol., 39:341-350, 2001.

Jarosik et al., "Identification of a New Locus Involved in Expression of *Haemophilus influenzae* Type b Lipooligosaccharide", Infect. Immun., 62:4861-4867, 1994.

Kahler et al., "Two Glycosyltransferase Genes, *IgtF* and *rfaK*, Constitute the Lipooligosaccharide *ice* (Inner core Extension) Biosynthesis Operon of *Neisseria meingitidis*", J. Bacteriol., 178:6677-6684, 1996.

Kyd et al., "Enhanced Respiratory Clearance of Nontypeable *Haemophilus influenzae* following Mucosal Immunization with P6 in a Rat Model", Infect. Immun., 63:2931-2940, 1995; Deich et al., Vaccine Res., 2:31-39, 1995.

Lesse et al., "Increased resolution of lipopolysaccharides and lipooligosaccharides utilizing tricine-sodium dodecyl sulfate-polyacrylamide gel electrophoresis", J. Immunolog. Methods, 126:109-117, 1990.

Lysenko et al., "The position of phosphorylcholine on the lipopolysaccharide of *Haemophilus influenzae* affects binding and sensitivity to C-reactive protein-mediated killing", Mol. Microbiol., 35:234-245, 2000.

Masoud et al., "Structure of the Variable and Conserved Lipopolysaccharide Oligosaccharide Epitopes Expressed by *Haemophilus influenzae* Serotype b Strain Eagan", Biochem., 36:2091-2103, 1997 (1997).

McGehee et al., "Effect of Primary Immunization on Pulmonary Clearance of Nontypable *Haemophilus influenzae*", (Am. Journal Respir. Cell Biol., 1:201-210, 1989).

Medaglini et al., "Mucosal and systemic immune responses to a recombinant protein expressed on the surface of the oral commensal bacterium *Streptococcus gordonii* after oral colonization", Proc. Natl. Acad. Sci. USA, 92:6868-6872, 1995.

Pappenheimer et al., "An Immunological Study of the Diphtheria Toxin Molecule", Immunochem., 9:891-906, 1972.

Patrick et al., "Antigenic Characterization of the Oligosaccharide Portion of the Lipooligosaccharide of Nontypable *Haemophilus influenzae*", Infect Immun., 55:2902-2911, 1987.

Phillips et al., "Structural Characterization of the Cell Surface Lipooligosaccharides from a Nontypable Strain of *Haemophilus influenzae*¦", Biochem., 31:4515-4526, 1992.

Phillips et al., "Characterization of Two Transposon Mutants from *Haemophilus influenzae* Type b with Altered Lipooligosaccharide Biosynthesis†", Biochem., 35:5937-5947, 1996.

Potter et al., "Cloning and characterization of a gene from *Pasteurella haemolytica* A1 involved in lipopolysaccharide biosynthesis", FEMS Microbiol. Lett., 129:75-82, 1995.

Preston et al., "Altered Lipopolysaccharide Characteristic of the 169 Phenotype in *Haemophilus influenzae* Results from Mutations in a Novel Gene, *isn*", J. Bacteriol., 178:396-402, 1996.

Rahman et al., "The structural heterogeneity of the lipooligosaccharide (LOS) expressed by pathogenic non-typeable *Haemophilus influenzae* strain NTHi 9274", Glycobiology, 9:1371-1380, 1999.

Risberg et al., "Structural analysis of the lipopolysaccharide oligosaccharide epitopes expressed by a capsule-deficient strain of *Haemophilus influenzae* Rd", Eur. J Biolchem., 261:171-180, 1999.

Risberg et al., "Structural studies of the cell-envelope oligosaccharide from the lipopolysaccharide of *Haemophilus influenzae* strain RM.118-28", Eur. J. Biochem., 243:701-707, 1997.

Risberg et al., "Structural analysis of the lipopolysaccharide oligosaccharide epitopes expressed by *Haemophilus influnezae* strain RM.118-26", Eur. J. Biochem., 265:1067-1074, 1999.

Roche et al., "Phase variation of *Haemophilus influenzae* lipopolysaccharide: Characterization of lipopolysaccharide from individual colonies", FEMS Microbiol. Lett., 120:279-284, 1994.

Schweda et al., "Structural studies of the saccharide part of the cell envelope lipopolysaccharide from *Haemophilus influenzae* strain AH1-3 (*lic3+*)", Carbohydr. Res., 246:319-330, 1993.

Schweda et al., "Structural studies of the saccharide part of the cell envelope lipooligosaccharide from *Haemophilus influenzae* strain galEgalK", Carbohydr. Res., 272:213-224, 1995.

Schweda et al., "Characterization of the phosphocholine-substituted oligosaccharide in lipopolysaccharides of type b *Haemophilus influenzae*", Eur. J. Biochem., 267:3902-3913, 2000.

Sizemore et al., "Attenuated *Shigella* as a DNA Delivery Vehicle for DNA-Mediated Immunization", Science, 270:299, 1995.

Stool et al., "The impact of otitis media", Pediatr. Infect. Dis. Suppl. J., 8:S11-S14, 1989.

Sun et al., "Biological activities of antibodies elicited by lipooligosaccharide based-conjugate vaccines of nontypeable *Haemophilus influenzae* in an otitis media model", Vaccine, 18:1264-1272, 2000.

Thibault et al., "Applications of Combined Capillary Electrophoresis-Electrospray Mass Spectrometry in the Characterization of Short-Chain Lipopolysaccharides", Methods in Molecular Biology, vol. 145, Bacterial Toxins: Methods and Protocols (Holst, O., ed.) pp. 327-344, Humana Press, 2000.

Virji et al., "Antigenic similarities in lipopolysaccharides of *Haemophilus* and *Neisseria* and expression of a digalactoside structure also present on human cells", Microb. Pathogen., 9:441-450, 1990.

Wakarchuk et al., "Functional Relationships of the Genetic Locus Encoding the Glycoyltransferase Enzymes Involved in Expression of the Lacto-*N*-neotetraose Terminal Lipopolysaccharide Structure in *Neisseria meningitidis*", J. Biol. Chem., 271:19166-19173, 1996.

Wakarchuk et al., "Role of paired basic residues in the expression of active recombinant galactosyltransferases from the bacterial pathogen *Neisseria meningitidis*", Protein Eng., 11:295-302, 1998.

Weiser et al., "The Molecular Mechanism of Phase Variation of H. influenzae Lipopolysaccharide", Cell, 59:657-665, 1989.

Weiser et al., "Characterization of Repetitive Sequences Controlling Phase Variation of *Haemophilus influenzae* Lipopolysaccharide", J. Bacteriol., 172:3304-3309, 1990.

Weiser et al., "Decoration of Lipopolysaccharide with Phosphorylcholine: a Phase-Variable Characteristic of *Haemophilus influenzae*", Infect. Immun., 65:943-950, 1997.

Weiser et al., "Adaptation of *Haemophilus influenzae* to acquired and innate humoral immunity based on phase variation of lipopolysaccharide", Mol. Microbiol., 30:767-775, 1998.

Westphal et al., "Bacterial Lipopolysaccharides—Extraction with Phenol-Water and Further Applications of the Procedure", Meth. Carbohydr. Chem., 5:83-91, 1965.

White et al., "A *Haemophilus influenzae* Gene That Encodes a Membrane Bound 3-Deoxy-D-*manno*-octulosonic Acid (Kdo) Kinase", J. Biol. Chem., 274:31391-31400, 1999.

Zamze et al., "Composition of the Lipopolysaccharide from Different Capsular Serotype Strains of *Haemophilus influenzae*", J. Gen. Microbiol., 133:1443-1451, 1987.

Berlind, C. et. al. 1998. J. Org. Chem. 63:7780-7788.

Risberg, A. et. al. 1999. Eur. J. Biochem. 261:171-180.

Phillips, N.J. et. al. 1996. Biochemistry. 35:5937-5947.

M. Mahbubur Rahman et. al. 1999. Glycobiology. 9,12:1371-1380.

* cited by examiner

HAEMOPHILUS INFLUENZAE LIPOPOLYSACCHARIDE INNER-CORE OLIGOSACCHARIDE EPITOPES AS VACCINES FOR THE PREVENTION OF HAEMOPHILUS INFLUENZAE INFECTIONS

CROSS-REFERENCE TO RELATED APPLICATIONS

This is a U.S. national phase application of International Patent Application No. PCT/CA01/01225 filed Aug. 27, 2001, which claims priority from U.S. Provisional Patent Application Ser. No. 60/227,850 filed Aug. 25, 2000.

FIELD OF THE INVENTION

The present invention relates to defined mutations in the biosynthetic machinery for lipopolysaccharide (LPS) expression in *Haemophilus influenzae*. The invention also relates to using conjugates of the LPS from the mutant strains so obtained to elicit a heterologous immune response against a wide range of disease-causing *H. influenzae* strains. More specifically, the invention relates to vaccines for prevention of bacterial infections comprising core lipopolysaccharide of *Haemophilus influenzae*.

BACKGROUND OF THE INVENTION

*Haemophilus influenzae* is a major cause of disease worldwide. Six capsular serotypes ("a" to "f") and an indeterminate number of acapsular (non-typeable) strains of *H. influenzae* are recognised. Type b capsular strains are associated with invasive diseases, including meningitis and pneumonia, while non-typeable *H. influenzae* (NTHi) is a primary cause of otitis media in children and respiratory tract infections in adults. Otitis media is a common childhood disease which accounts for the highest frequency of paediatric visits in the United States (Stool et al., Pediatr. Infect. Dis. Suppl., 8:S11-S14, 1989).

The development of a vaccine for NTHi diseases has proved difficult because of a lack of understanding of the antigens that confer protective immunity. Efforts in developing a NTHi vaccine have been focused on cell surface antigens such as outer membrane proteins and pili or fimbria (Kyd et al., Infect. Immun., 63:2931-2940, 1995; Deich et al., Vaccine Res., 2:31-39, 1995).

Recent advances in molecular genetics, molecular structure analysis and immunochemistry provide powerful tools which have permitted the identification of carbohydrate: structures as candidate vaccine antigens.

Gram-negative bacteria have an outer membrane comprised of components including proteins, lipoproteins, phospholipids, and glycolipids. The glycolipids comprise primarily endotoxin lipopolysaccharides (LPS). LPS are molecules comprised of a) a Lipid A portion which consists of a glucosamine disaccharide that is substituted with phosphate groups and long chain fatty acids in ester and amide linkages; b) a core polysaccharide which is attached to Lipid A by an eight carbon sugar, Kdo (ketodeoxyoctonate), and heptose, glucose, galactose, and N-acetylglucosamine; and, optionally, c) O-specific side chains comprised of repeating oligosaccharide units which, depending on the genera and. species of bacteria, may contain mannose, galactose, D-glucose, N-acetylgalactosamine, N-acetylglucosamine, L-rhamnose, and a dideoxyhexose (abequose, colitose, tyvelose, paratose, trehalose). LPS which lacks repeating O-side chains is sometimes referred to as short chain lipopolysaccharide, or as lipooligosaccharide (LOS). In this application, the term lipopolysaccharide (or LPS) includes short chain lipopolysaccharide and lipooligosaccharide (and LOS).

The major antigenic determinants of gram-negative bacteria are believed to reside in the complex carbohydrate structure of LPS. These carbohydrate structures vary significantly, even among different species of the same genus of gram-negative bacteria, primarily because of variations in one or more of the sugar composition, the sequence of oligosaccharides, the linkage between the monomeric units of the oligosaccharides and between the oligosaccharides themselves, and substitutions/modifications of the oligosaccharides (particularly the terminal oligosaccharide). For this reason, development of a vaccine having a broad spectrum effect against *Haemophilus influenzae* (particularly against NTHi) has been unsuccessful.

LPS is a bacterial component which has potential as a vaccine immunogen because of the antigenic determinants ("epitopes") residing in its carbohydrate structures. However, the chemical nature of LPS detracts from its use in vaccine formulations; i.e., active immunization with LPS is unacceptable due to the inherent toxicity, in some animals, of the Lipid A portion. The pathophysiologic effects induced (directly or indirectly) by Lipid A of LPS in the bloodstream include fever, leucopenia, leucocytosis, the Shwartzman reaction, disseminated intravascular coagulation, abortion, and in larger doses, shock and death.

It has been established that vaccines comprised of capsular polysaccharides are effective at preventing human disease caused by the homologous encapsulated bacteria. These carbohydrate antigens are often poorly immunogenic in humans due to a lack of T-cell dependent response. However, by conjugating the specific polysaccharide antigen to a suitable protein carrier, the immunogenicity of the carbohydrate antigen can be greatly enhanced in patients who do not respond to the polysaccharide alone. Glycoconjugate vaccines based on the specific capsular polysaccharide of type b *H. influenzae* (Hib), e.g. ProHiBit™, and ActHib™, have already proven successful in the control of invasive Hib disease in infants. Capsular polysaccharide-protein conjugate Hib vaccines do not provide protection against disease caused by acapsular (non-typeable) strains of *H. influenzae* (i.e. against disease caused by NTHi) because they are only protective against infections caused by *H. influenzae* strains bearing the type b capsule.

Lipopolysaccharide (LPS) is a major NTHi cell surface antigen. LPS of *Haemophilus influenzae* has only been found to contain lipid A and oligosaccharide (OS) components. Because the lipid A component of LPS is toxic, it must be detoxified prior to conjugation to an immunogenic carrier, as discussed above.

Barenkamp et al. (Pediatr. Infect. Dis. J., 9:333-339, 1990) demonstrated that LOS stimulated the production of bactericidal antibodies directed against NTHi. McGehee et al. (Am. Journal Respir. Cell Biol., 1:201-210, 1989) showed that passive immunization of mice with monoclonal antibodies directed against LOS from NTHi enhanced the pulmonary clearance of NTHi.

Green et al. (Vaccines, 94:125-129, 1994) disclose a NTHi vaccine comprising a conjugate of NTHi oligosaccharide and the mutant nontoxic diphtheria protein CRM.sub.197. The lipid A moiety was removed from LOS by treatment with acid, followed by derivatizing the resulting OS with adipic acid dihydrazide (ADH) and coupling to CRM.sub.197. Despite the showing of Barenkamp et al. that LOS stimulated production of bactericidal antibodies against NTHi, the conjugates of Green et al. were determined to be poorly immunogenic after injection into mice. Moreover, the conjugates did not elicit bactericidal antibodies against NTHi.

Gu et al. (U.S. Pat. No. 6,207,157) is concerned with the detoxification of isolated NTHi LOS by removal of ester-linked fatty acids therefrom, so that it may be made suitable for vaccine preparation. However, Gu does not describe any other modifications to or desired chemical attributes of NTHi LOS.

There is currently no vaccine available to provide broad spectrum protection against infections caused by *Haemophilus influenzae*. Thus, there is a need for a vaccine having broad spectrum efficacy against *Haemophilus influenzae*, particularly NTHi.

In order to utilise an antigen for vaccine development, four essential criteria must be fulfilled. That is, the immunogenic epitope must be:
1. genetically stable;
2. conserved in all clinically relevant strains across the species;
3. accessible (in vitro and in vivo) to host immune mechanisms; and,
4. able to induce protective antibodies in vivo.

There is a need to identify LPS carbohydrate epitopes of *H. influenzae*, particularly NTHi, which satisfy these criteria.

SUMMARY OF THE INVENTION

The present disclosure is directed at immunity providing B-cell activating molecules derived from *H. influenzae* lipopolysaccharide (LPS), said molecules comprising one or more epitopes of a conserved inner-core oligosaccharide portion of the lipopolysaccharide. There is also disclosed a strategy to identify and characterise said epitopes that are representative of LPS expressed by *H. influenzae* strains across the range of disease causing isolates. There is also disclosed methods for obtaining such epitopes, both synthetically and through genetic engineering techniques and conjugates of molecules comprising said epitopes with suitable carriers, optionally in liposome formulations.

In one aspect, the invention provides a lipopolysaccharide moiety comprising a conserved triheptosyl inner-core moiety of lipopolysaccharide substantially free of variable outer core oligosaccharide chain extensions.

In another aspect, the invention provides a lipopolysaccharide moiety comprising a triheptosyl inner-core moiety of *Haemophilus influenzae* lipopolysaccharide having the following structure [I]:

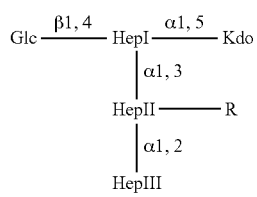

wherein R is hydrogen or phosphoethanoelamine, Glc is D-glucopyranose, and Kdo is 3-deoxy-D-manno-2-octulosonic acid.

In another aspect, the invention provides an isolated lipopolysaccharide moiety consisting essentially of a trihep-tosyl inner-core moiety of *Haemophilus influenzae* lipopolysaccharide having the following structure:

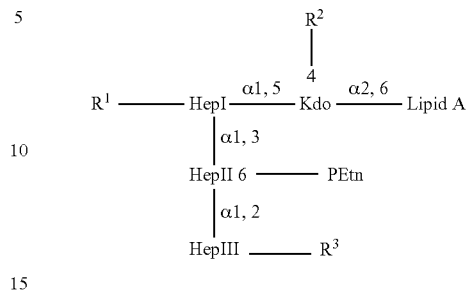

wherein
$R^1$ is hydrogen, β-D-Glcp(1→4), or PCho→6)-β-D-Glcp (1→4);
$R^2$ is phosphate (P) or pyrophosphoethanolamine (P-PEtn);
$R^3$ is hydrogen, β-D-Glcp, or β-D-Galp, and when $R^1$ is hydrogen or β-D-Glcp(1→4), then $R^3$ may also be β-D-Galp-(1→4)-β-D-Glcp,
α-D-Galp-(1→4)-β-D-Galp-(1→4)-β-D-Glcp,
β-D-GalpNAc-(1→3)-α-D-Galp-(1→4)-β-D-Galp-(1→4)-β-D-Glcp, or
α-NeuAc(2→3)-β-D-Galp-(1→4)-β-D-Glcp-(1→3),
wherein $R^3$ is attached at either the O-3 or O-2 position of HepIII; Kdo is 3-deoxy-D-manno-2-octulosonic acid; and Lipid A is detoxified.

In another aspect, the invention provides an immunogenic composition for conferring protection in an animal host against a disease caused by *Haemophilus influenzae*, comprising either of the lipopolysaccharide moieties described above.

In another aspect, the invention provides a glycoconjugate comprising either of the lipopolysaccharide moieties described above, and an immunogenic carrier cross-linked to the lipopolysaccharide moiety.

In another aspect, the invention provides a use of at least one gene in a biosynthetic pathway for the production of lipopolysaccharide in *Haemophilus influenzae* to obtain a *Haemophilus influenzae* strain comprising either of the lipopolysaccharide moieties described above.

In another aspect, the invention provides a process for preparing a lipopolysaccharide moiety consisting essentially of a conserved triheptosyl inner-core moiety having the structure II:

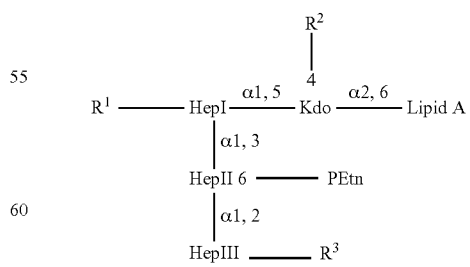

wherein
$R^1$ is hydrogen, β-D-Glcp(1→4), or PCho→6)-β-D-Glcp (1→4);

$R^2$ is phosphate (P) or pyrophosphoethanolamine (P-PEtn); $R^3$ is hydrogen, β-D-Glcp, β-D-Galp, β-D-Galp-(1→4)-β-D-Glcp, α-D-Galp-(1→4)-β-D-Galp-(1→4)-β-D-Glcp, and when $R^1$ is hydrogen or β-D-Glcp(1→4), then $R^3$ may also be β-D-GalpNAc-(1→3)-α-D-Galp-(1→4)-β-D-Galp-(1→4)-β-D-Glcp, or α-NeuAc(2→3)-β-D-Galp-(1→4)-β-D-Glcp-(1→3), wherein $R^3$ is attached at either the O-3 or O-2 position of HepIII; and Kdo is 3-deoxy-D-manno-2-octulosonic acid; said process comprising:

transforming a recipient *Haemophilus influenzae* bacterial strain with one or more inactivated genes selected from the group consisting of lpsA, lic1, lic2, lic2A, lic2orf3, lic2B, lic3A, lgtC, lgtD, and lgtF;

culturing the transformed *Haemophilus influenzae* bacterial strain under conditions suitable for expressing the lipopolysaccharide moiety;

isolating the lipopolysaccharide moiety; and detoxifying the Lipid A portion of the lipopolysaccharide moiety.

In another aspect, the invention provides a use of at least one immunogenic epitope to elicit a functional cross-reactive antibody against *Haemophilus influenzae* wherein the epitope comprises either of the lipopolysaccharide moieties described above.

In another aspect, the invention provides a functional antibody which is cross-reactive against *Haemophilus influenzae* and which is elicited by either of the lipopolysaccharide moieties described above.

In another aspect, the invention provides a method for the production of a functional cross-reactive antibody against *Haemophilus influenzae* which comprises: (a) generating antibodies to either of the lipopolysaccharide moieties described above, (b) testing such antibodies against a plurality of *Haemophilus influenzae* strains, and (c) selecting those antibodies which are cross-reactive.

In another aspect, the invention provides a method of immunizing a host against disease caused by infection with *Haemophilus influenzae* which comprises administering to the host an immunoeffective amount of the immunogenic composition described above.

DETAILED DESCRIPTION OF THE INVENTION

Figure 1:
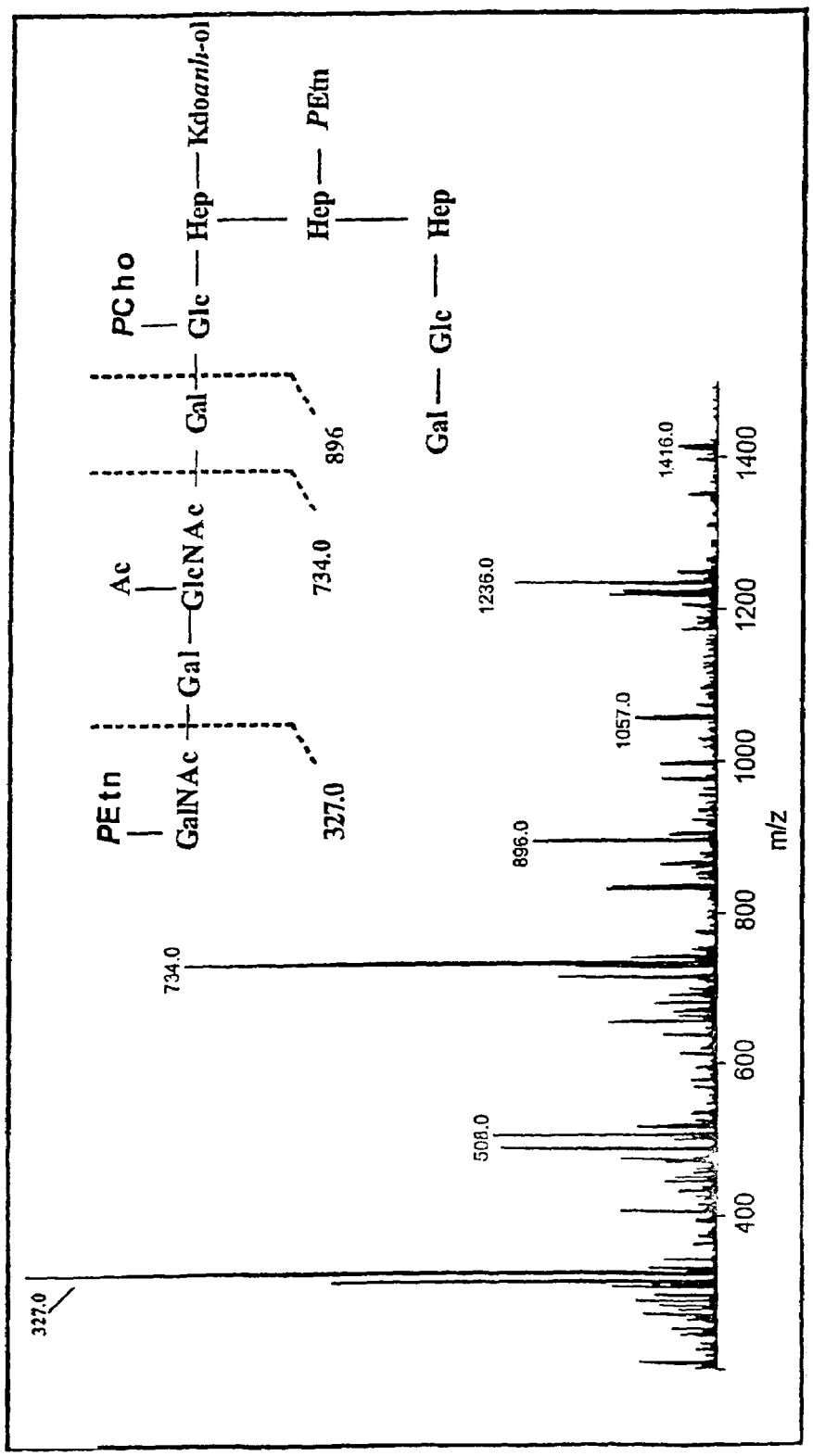
FIG. 1 is a structural verification of the high molecular weight form RM118.

Lipopolysaccharide (LPS) is an essential and characteristic surface-exposed antigen of *H. influenzae*. (As discussed above, the terms lipopolysaccharide and LPS as used herein encompass short chain lipopolysaccharide and lipooligosaccharide (LOS).) *H. influenzae* strains express heterogeneous populations of low-molecular-weight LPS which can exhibit extensive antigenic diversity among multiple oligosaccharide epitopes. The LPS carbohydrate structures of *H. influenzae* described by the Applicant herein can provide a source of protective antigens when they are presented to the human immune system in an appropriate fashion, for example, as a protein-conjugate or in a liposome formulation. Antibodies against certain NTHi LPS have shown bactericidal activity in vitro (Sun et al. Vaccine 18:1264-1272). A recent study (Gu et al., U.S. Pat. No. 6,207,157) has indicated that: immunization with LPS-based conjugates can reduce the incidence of NTHi-induced otitis media due to a homologous strain in an animal model. LPS proved useful as a vaccine candidate in Applicant's study because, surprisingly, surface expressed carbohydrate antigens were identified which possess oligosaccharide epitopes that are genetically and physiologically stable, that are conserved across the range of clinically relevant strains, and that are accessible to host clearance mechanisms.

The carbohydrate regions of *H. influenzae* LPS molecules provide targets for recognition by host immune responses. Expression of certain oligosaccharide epitopes is known to contribute to the pathogenesis of *H. influenzae* infections. Determination of structure is crucial to understanding the biology of *H. influenzae* LPS and its role in bacterial virulence. *H. influenzae* LPS comprises a heterogeneous mixture of molecules consisting of a variable oligosaccharide moiety and a membrane anchoring-Lipid A component (Zamze et al., J. Gen. Microbiol., 133:1443-1451, 1987). Based on the experiments described herein, a structural model was developed for *Haemophilus* LPS consisting of a conserved triheptosyl inner-core moiety which is attached via a phosphorylated ketodeoxyoctonoate residue to a lipid A component. In every strain investigated by Applicant to date this triheptosyl moiety consists of the following structural element

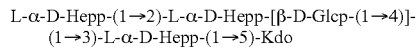

L-α-D-Hepp-(1→2)-L-α-D-Hepp-[β-D-Glcp-(1→4)]-(1→3)-L-α-D-Hepp-(1→5)-Kdo

Additionally, in every strain investigated by Applicant to date, the 1,2-linked heptose residue (HepII) is substituted with a phosphoethanolamine moiety at the 6 position.

Each of the heptose residues within the inner-core region can provide a site for elongation by hexose-containing oligosaccharide chains or for attachment of non-carbohydrate substituents. Published data (Masoud et al., Biochem. 36:2091-2103, 1997; Risberg et al., Eur. J. Biochem. 261: 171-180, 1999) indicates that the distal heptose residue (HepIII) in this conserved inner-core moiety can be substituted by a β-D-Glcp or β-D-Galp residue at the O-2 position. Substitutions are also possible on HepII, specifically by an α-D-glucose or a substituted α-D-glucose at the 3 position. The β-D-glucose residue which is 1,4-linked to the proximal heptose residue (HepI) can itself be further substituted by a β-D-glucose, a β-D-galactose, a heptose (including L-glycero-D-manno-heptose and D-glycero-D-manno-heptose), or oligosaccharides thereof. Additionally to these sugar residues, oligosaccharide chain extensions can comprise β-D-galactose, β-D-glucosamine, β-D-galactosamine, and 5-N-acetylneuraminic acid (sialic acid).

The degree of substitution and chain extension from the triheptosyl moiety varies within and between strains (Masoud et al., Biochem. 36:2091-2103, 1996; Risberg, et al., Eur. J. Biochem. 261:171-180, 1999). Phosphate-containing substituents which include free phosphate groups (P), phosphoethanolamine (PEtn), pyrophosphoethanolamine (PPEtn), and phosphocholine (PCho) contribute to the structural variability of these molecules. Moreover, ester substituents (including O-acetyl and O-glycyl) also contribute to the structural variability of LPS. Other modifications of LPS are possible such as addition of sialic acid residues. Sialylated oligosaccharides are commonly found in mammalian tissue and this modification is believed to improve mimicry of human tissue structures.

Detailed structural studies of LPS from defined mutants of the type b strain RM7004 (Schweda et al., Carbohydr. Res. 246:319-330, 1993; Schweda et al., Carbohydr. Res. 272: 213-224, 1995), transformed variants of the type d derived strain RM118 (Risberg et al., Eur. J. Biochem. 243:701-707, 1997; Risberg et al., Eur. J. Biochem. 265:1067-1074, 1999), and transposon mutants of the type b strain A2 (Phillips et al., Biochem. 35:5937-5947, 1996) provide further evidence for the presence of a common heptose-containing trisaccharide inner-core moiety in *H. influenzae* LPS. There has been reported the structure of a globotetraose (β-D-GalpNAc-(1→3)-β-D-Galp-(1→4)-β-D-Galp-(1→4)-β-D-Glcp) containing. LPS from *H. influenzae* strain RM118 (Risberg et al., Eur. J. Biochem. 261:171-180, 1999), the strain (Rd) for which the complete genome sequence has been determined (Fleischmann et al., Science 269:496-512, 1995). In this study, three major populations of LPS glycoforms were identified, all containing a PCho→6)-β-D-Glcp group off the Hep attached to the Kdo moiety (HepI), but differing in the length of the oligosaccharide chains off the distal Hep (HepIII) of the inner-core element. In addition to LPS glycoforms expressing a fully assembled globotetraose side-chain, sequentially truncated glycoforms containing globoside (α-D-Galp-1→4)-β-D-Galp-(1→4)-β-D-Glcp) and lactose (β-D-Galp-(1→4)-(β-D-Glcp) have been characterised (Risberg et al., Eur. J. Biochem. 261:171-180, 1999).

The availability of the complete genome sequence of *H. influenzae* strain Rd facilitated a comprehensive study of multiple LPS biosynthetic loci in representative Hi strains. Non-typeable strains were obtained from Prof. Eskola as part of a Finnish Otitis Media Cohort Study and are mainly isolates obtained from the inner ear of children. These strains are further described in Hood et al., Mol. Microbiol. 33:679-792, 1999. 102 NTHi otitis media strains were sent to Richard Goldstein in Boston to be included in a survey of the diversity of over 600 *H. influenzae* capsulate and NTHi strains, obtained from around the world and over a 35 year period, by ribotyping analysis. When a dendrogram was drawn from the results of the ribotyping, the NTHi otitis media isolates were found to be present in almost all of the branches obtained. The 25 representative strains were selected from branches spanning the dendrogram and thus represent the known diversity associated with the species *H. influenzae*. Included in the 25 strains are some selected from the same cluster to allow an assessment of the diversity of closely related isolates.

Many predicted gene functions were correlated with particular steps in the synthesis of the LPS by analysis of LPS structure from the appropriate mutant strains (Hood. et al., Mol. Microbiol. 22:951-965). The genetic basis for expression of the globotetraose structure has not previously been reported.

As described in the examples, Applicant employed a structural fingerprinting strategy to determine and compare the structures of LPS obtained from a series of defined-mutants in LPS biosynthetic genes in *H. influenzae* strain RM118. (For a description of strain RM118, see Risberg et al., 1999, supra.) By examination of LPS from strains in which specific genes are inactivated, Applicant presents definitive evidence leading to the identification of the glycosyltransferases involved in the biosynthesis of the inner-core region of the LPS molecule. Applicant has also identified genes involved in the assembly of sialylated lactose side chain, as further described below. Moreover, the transferase functions of genes involved in addition of α-2,3-linked Neu5Ac (lic3A), α-1,4-linked Galp (lgtC) and β-1,3-linked GalpNAc (lgtD) to give the globotriose and globotetraose structures, respectively, were unambiguously determined by enzymatic assays with synthetic acceptors. This is the first study to identify a genetic blueprint for biosynthesis of a LPS oligosaccharide moiety for a strain of *H. influenzae*.

In our investigation of the *H. influenzae* LPS inner-core, attempts to remove Kdo, the first sugar added to the Lipid A, have repeatedly failed presumably as Kdo is required to complete Lipid A synthesis and is thus likely essential for cell viability. The Kdo transferase function of kdta has been demonstrated by complementation experiments in *E. coli* (White et al., FASEB J. 12:L44, 1998).

Applicant's studies indicate that opsX, rfaF and orfH are the genes encoding the enzymes which add the first, second and third heptoses (HepI, HepII and HepIII), respectively, to the Kdo to form the inner-core. opsX has some homology to heptosyl transferases of the enteric bacteria (Hood et al., Mol. Microbiol. 22:951-965, 1996) and corresponds to a gene responsible for adding HepI to Kdo. The rfaF mutant has a functional opsX gene and its LPS has a single Hep attached to Kdo-Lipid A. The rfaF gene of RM118 (Rd) has homology to other heptosyl transferases (Allen et al., J. Bacteriol. 180:35-40, 1998). LPS from RM118orfH which has functional opsX and rfaF genes comprise structures containing two heptose residues. The data on structural analyses of LPS from RM118opsX, rfaF and orfH mutants is consistent with that obtained with the same mutations in the type b strains RM153 (also known as strain Eagan) and RM7004 (Hood et al., Mol. Microbiol. 22:951-965, 1996). In the type b strains, opsX, rfaF and orfH are proposed as the genes encoding the HepI, HepII and HepIII transferases respectively.

Applicant has shown that the LPS of *H. influenzae* has the aforementioned triheptosyl inner-core moiety in which each heptose residue provides a point for elongation by oligosaccharide chains (Masoud et al., Biochem. 36:2091-2103, 1996; Risberg et al., Eur. J. Biochem. 261:171-180, 1999). Each of the genes lpsA, lic2A, lic3A, lgtC, lgtD and lgtF encode glycosyltransferase enzymes involved in oligosaccharide elongation.

These results indicate that the lpsA gene product plays a role in controlling oligosaccharide chain extension from HepIII. A mutation in the lpsA gene affords a truncated LPS in which HepIII is devoid of oligosaccharide chain extensions. ESI-MS analysis of the RM118lpsA derived O-deacylated LPS indicated a Pcho-containing glycoform containing a single hexose residue as the major LPS species, confirming that HepI can be substituted in the absence of hexose extension from HepIII. The lic2A, lgtC and lgtD mutants which contain a functional lpsA gene are capable of adding a β-D-Glcp residue in a 1,2-linkage to initiate chain extension from HepIII. lpsA is a homologue of a gene encoding a glycosyltransferase in *Pasteurella haemolytica* (Potter et al., FEMS Microbiol. Lett. 129:75-81, 1995), the protein of which has homology to the group of galactosyltransferases typified by Lic2A and LgtB of *Haemophilus* and *Neisseria* respectively. In strain RM153, it was also found that LPS from a lpsA mutant lacked any chain extension from the third heptose (Hood et al., Mol. Microbiol. 22:951-965, 1996). Moreover, Applicant has confirmed that LpsA mutants in several NTHi strains lack chain extensions from HepIII. Thus, LpsA is the transferase for the addition of the first sugar to HepIII in *H. influenzae* LPS biosynthesis.

The RM118lic2A mutant showed a PCho-containing Hex2 glycoform as a major LPS species (Structure 4; Table 1) and RM118lgtC, which contains a functional lic2A gene, elaborates LPS containing a lactose side chain at HepIII (Structure 5; Table 1). This is consistent with the involvement of the lic2A gene to add the β-D-Galp unit in a 1,4 linkage to the terminal β-D-Glcp residue attached to HepIII. Lic2A homologues in the type b strains, RM153 and RM7004 have been shown to be involved in expression of the digalactoside-containing $P^K$ epitope (the globoside trisaccharide having the structure α-D-Galp-(1→4)-β-D-Galp-(1→4)-β-D-Glcp). The role of lic2A in phase variable expression of this epitope has been previously demonstrated (High et al., Mol. Microbiol. 9:1275-1282, 1993). Homology comparisons with other data bank sequences support the function of Lic2A as a β-galactosyltransferase. Importantly, it has significant homology to the Neisseria LgtB and LgtE proteins, both of which are galactosyltransferases (Wakarchuk et al., J. Biol. Chem. 271:1916-1917, 1996).

Structural analysis of LPS from an RM118 strain, mutated in lgtC, confirmed the loss of α-D-Galp supporting the α-galactosyltransferase function for this gene. A homologue of this gene in *N. meningitidis* has been demonstrated to be an α-galactosyltransferase (Gotschlich, J. Exp. Med. 180: 2181-2190, 1994; White et al., FASEB J. 12:L44, 1998; Wakarchuk et al., Protein Eng. 11:295-302, 1998). lgtC from *H. influenzae* has an associated tetranucleotide repeat (5'-GACA-3') just within the 5' end of the reading frame (Hood et al., Proc. Natl. Acad. Sci. USA 93:11121-11125, 1996) and therefore contributes to the variable phenotype of the oligosaccharide in RM118 LPS. Correspondingly, the lgtD mutant and the parent strain which contain a functional lgtC gene are capable of adding an α-D-Galp in a 1,4 linkage to the terminal β-D-Galp of the lactose epitope (Structure 6; Table 1). The function of LgtC was confirmed by demonstrating α-galactosyltransferase activity with the recombinant LgtC protein and a synthetic FCHASE-Lac acceptor. It follows that the lgtC gene encodes the specific α-galactosyltransferase for the synthesis of the α-D-Galp-(1→4)-β-D-Galp of the RM118 Hex4 LPS glycoform.

The *H. influenzae* lgtD gene is a homologue of two Neisseria genes, lgtA and lgtD, which add GlcNAc and GalNAc respectively to N. gonorrhoeae LPS (Gotschlich, J. Exp. Med. 180:2181-2190, 1994). The lgtA gene product has been demonstrated to be a glycosyltransferase in N. meningitidis (Wakarchuk et al., J. Biol. Chem. 271:1916-1917, 1996) There is significant homology between the Neisseria lgtA and lgtd genes and the best database match of RM118 HI1578 is to the N. gonorrhoeae lgtd gene. Enzyme assays with extracts of RM118 and the RM118lgtD mutant established the presence of. β-D-GalpNAc transferase activity. The parent strain RM118 that contains a functional lgtD gene is capable of elaborating the complete globotetraose unit which is indicative of its role in adding the terminal β-D-GalpNAc. The lgtd gene has been investigated previously (called lgtA in Hood et al., Mol. Microbiol. 22:951-965, 1996) and was found not to be present in the type b strains RM153 and RM7004. Correspondingly, the LPS elaborated by strain RM153 does not contain a GalNAc moiety (Masoud et al., Biochem. 36:2091-2103, 1996). Many NTHi strains have been found to contain the LgtD gene and the LPS oligosaccharide side chains of these strains have been found to contain a GalNAc moiety.

It is noteworthy that, while the glycosyltransferase activities encoded by the genes involving addition of the distal residues of the globotetraose (lgtD) and globoside (lgtC) oligosaccharide side-chains could be confirmed in an enzymatic assay with the appropriate synthetic acceptor, experiments to assay the transferase activity of the genes involved in synthesis of the lactose moiety (lic2A and lpsA) were unsuccessful. It is likely that the two latter enzymes have more stringent specificities that require the acceptor sugar to be linked to the inner-core heptose residues, thereby precluding recognition of the simple synthetic FCHASE-glycoside acceptors.

Figure 6:
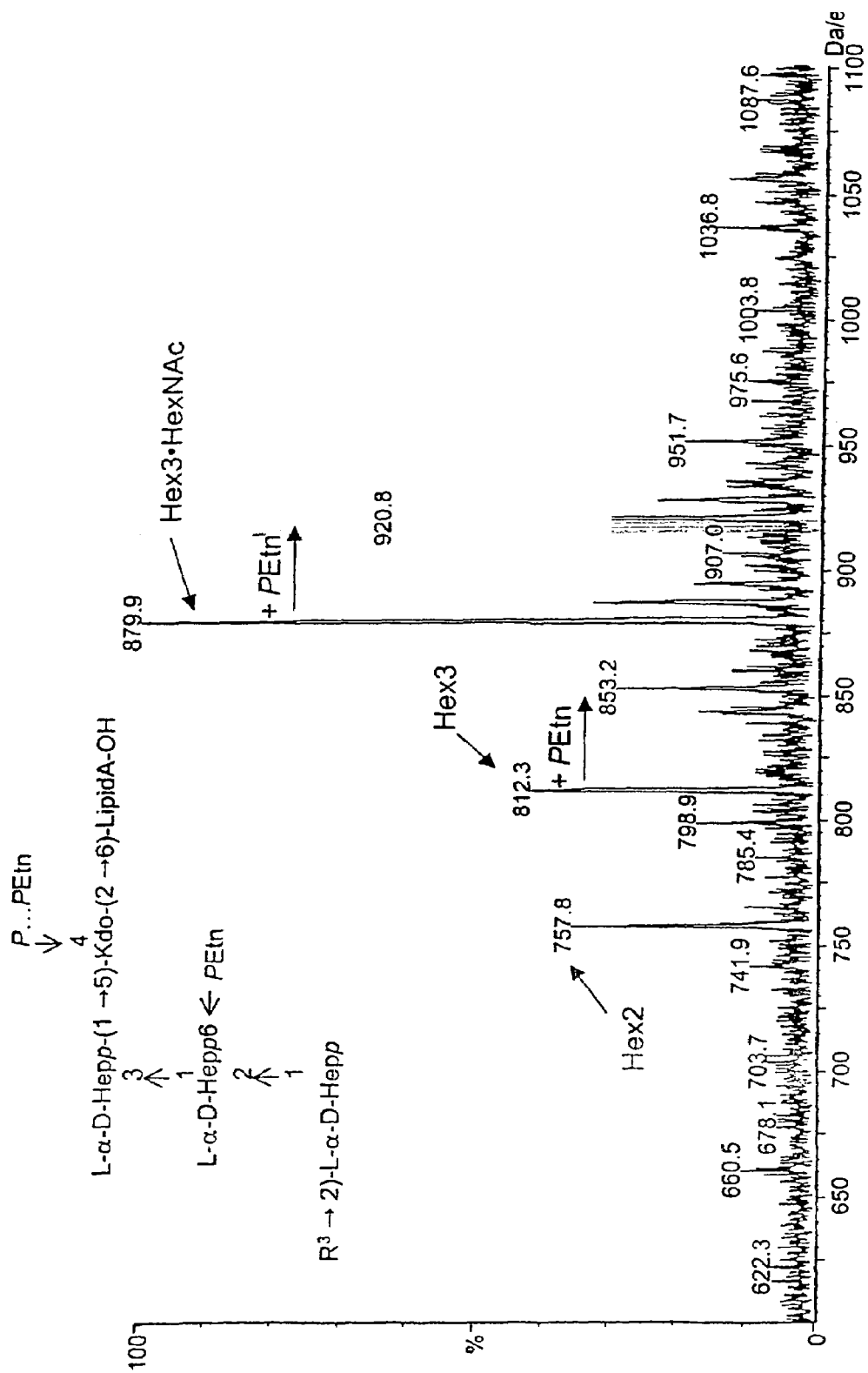
FIG. 6 is a negative ion ESI-MS of the triply charged molecular ion region of the O-deacylated LPS from the lgtF mutant of *H. influenzae* RM118 wherein peaks arising from the Hex 2 (β-D-Galp-(1→4)-β-D-Glcp), Hex 3 (α-D-Galp-(1→4)-β-D-Galp-(1→4)-β-D-Glcp), and Hex3.HexNAc (β-D-GalpNAc-(1→3)-α-D-Galp-(1→4)-β-D-Galp-(1→4)-β-D-Glcp) are indicated.

Characterisation of the initial set of genes and mutant strains available for study of RM118 LPS biosynthesis gave no obvious candidate responsible for the addition of β-D-Glcp unit to HepI. Further candidate LPS genes were investigated by searching the strain Rd genome sequence for low homology matches to genes adding hexose sugars to heptose residues in the LPS of other organisms. Search sequences included the rfaK and lgtF genes of *Neisseria*, genes involved in addition of hexose residues to heptose (Kahler et al., J. Bacteriol. 178:6677-6684, 1996). A lgtF homologue was identified in strain RM118 and analysis of the LPS from the strain mutated in this gene was indicative of the role of LgtF in chain extension from HepI. The ESI-MS showed molecular ions corresponding to a mixture of glycoforms having chain extensions from HepIII of a triheptosyl inner-core moiety, which lacks PCho→6)-β-D-Glcp at HepI (FIG. 6).

The lgtF and lpsA genes are key to the hexose extensions from the heptose containing inner-core unit of RM118 LPS, encoding the glycosyl transferase enzymes responsible for adding the first glycose to HepI and HepIII, respectively. The processes of chain extension from both HepI and HepIII appear to be largely independent in the LPS of strain RM118. Mutant strain RM118lpsA produces LPS which includes the β-D-Glcp moiety from HepI. Strain RM118lgtF produces a heterogeneous LPS containing oligosaccharide extensions from HepIII that include lactose and globotetraose chains. In strain RM153, lpsA apparently plays a slightly different role being responsible for the addition of galactose as the sole extension from the third heptose (Hood et al., Mol. Microbiol. 22:951-965, 1996). Surprisingly, it was determined that in certain non-typeable strains, lpsA can add either glucose or galactose at the O-3 position instead of the O-2 position.

The heterogeneity of *H. influenzae* LPS structure must be due in part to intrinsic variation in the biosynthesis of such a complex structure whereby not every molecule will be synthesised to completion. However, the majority of variation observed appears to be due to specific LPS biosynthetic genes capable of variable expression (phase variation). Structural analysis of LPS derived from wild-type and mutant RM118 strains has allowed Applicant for the first time to confirm the genes involved in the synthesis of an important phase variable epitope of *H. influenzae* LPS, the digalactoside. In strain RM118, Lic2A adds the proximal β-D-Galp and LgtC the terminal α-D-Galp to the digalactoside (α-D-Galp-(1→4)-β-D-Galp) as part of the oligosaccharide extension from HepIII whereas, the same epitope is expressed as the terminal extension from the second heptose in the type b strain RM153 (Masoud et al., Biochem. 36:2091-2103, 1996). Both lic2A and lgtC are phase variable. genes, making the expression of the epitope highly variable within and between organisms. The digalactoside epitope is expressed in the LPS of many of the NTHi strains disclosed in the present invention as well as in related bacteria, including *Neisseria* (Virji et al., Microb. Pathogen. 9:441-450, 1990). The epitope is potentially immunodominant and is of interest in pathogenesis as its presence offers the potential for molecular mimicry of host structures and can influence the survival of *Haemophilus influenzae* within experimental systems (Weiser et al., Mol. Microbiol. 30:767-775, 1998; Hood et al., Proc. Natl. Acad. Sci. USA. 93:11121-11125, 1996).

Sialylation of oligosaccharides is one modification which is believed to improve mimicry of human tissue structures, since sialylated oligosaccharides are commonly found in mammalian tissue. As described in the examples, Applicant has identified sialylated LPS in NTHi strains 375, 486 and strain RD, elucidating a role for lic3A in LPS synthesis (Hood et al., Mol. Microbiol. 39:341-350, 2001). A survey of 25 NTHi strains representative of the diversity of the species identified sialylated LPS oligosaccharide chain extensions in all but one. The mutation of lic3A in some NTHi strains, such as NTHi 486, has been demonstrated to have a major influence upon resistance to the killing effect of normal human serum. A comparison of the structures of LPS from NTHi 486 and its lic3A mutant revealed the presence of sialylated glycoforms (sialyl-lactose) only in the parent strain, which points to the importance of Lic3A for serum resistance in this strain. Addition of a charged sialic acid residue to LPS in Haemophilus influenzae appears to modulate antigenic mimicry of LPS epitopes.

In addition to the order and stereochemistry of the sugar residues which constitute the oligosaccharide portion of the LPS molecules, the location, type and frequency of substituents such as P, PEtn and PCho can have a profound affect on LPS structure and biological function. The lic1 locus has been shown to be essential for the phase-variable addition of PCho to the *H. influenzae* LPS molecule (Weiser et al., Infect. Immun. 65:943-950, 1997; Lysenko et al., Mol. Microbiol. 35:234-245, 2000). It has been demonstrated that PCho contributes to the resistance of *H. influenzae* to innate humoral immunity (Weiser et al., Mol. Microbiol. 30:767-775, 1998, Lysenko et al., Mol. Microbiol. 35:234-245, 2000). The gene encoding a Kdo kinase, kdkA, responsible for phosphorylation of Kdo, has been identified (White et al., J. Biol. Chem. 274:31391-31400, 1999). This gene has previously been investigated by the applicant as orfZ and when mutated was shown to alter bacterial survival in an infant rat model of infection (Hood et al., Mol. Microbiol. 22:951-965, 1996). The only remaining substituents in the core oligosaccharide, whose genetic control remains unknown, therefore, are the PEtn residues that are attached to the 6-position of the HepII residue stoichiometrically and sometimes to the phosphate group on Kdo.

In summary, the genetic blueprint for complete synthesis of the major oligosaccharide chain extensions of *Haemophilus influenzae* have been elucidated.

Applicant has investigated in excess of 25 strains representative of the known diversity of *Haemophilus influenzae*. Applicant has confirmed that the triheptosyl inner-core moiety of LPS (labelled HepI-HepIII) is conserved in all strains tested. This determination permits the synthesis of suitable oligosaccharides from the inner-core moiety of LPS for use in the preparation of vaccines which afford broad spectrum protection against *Haemophilus influenzae*, including NTHi. It also permits the selection and modification of strains of *Haemophilus influenzae* which synthesize suitable oligosaccharides from the inner-core moiety of LPS for use in the preparation of vaccines.

Figure 7:
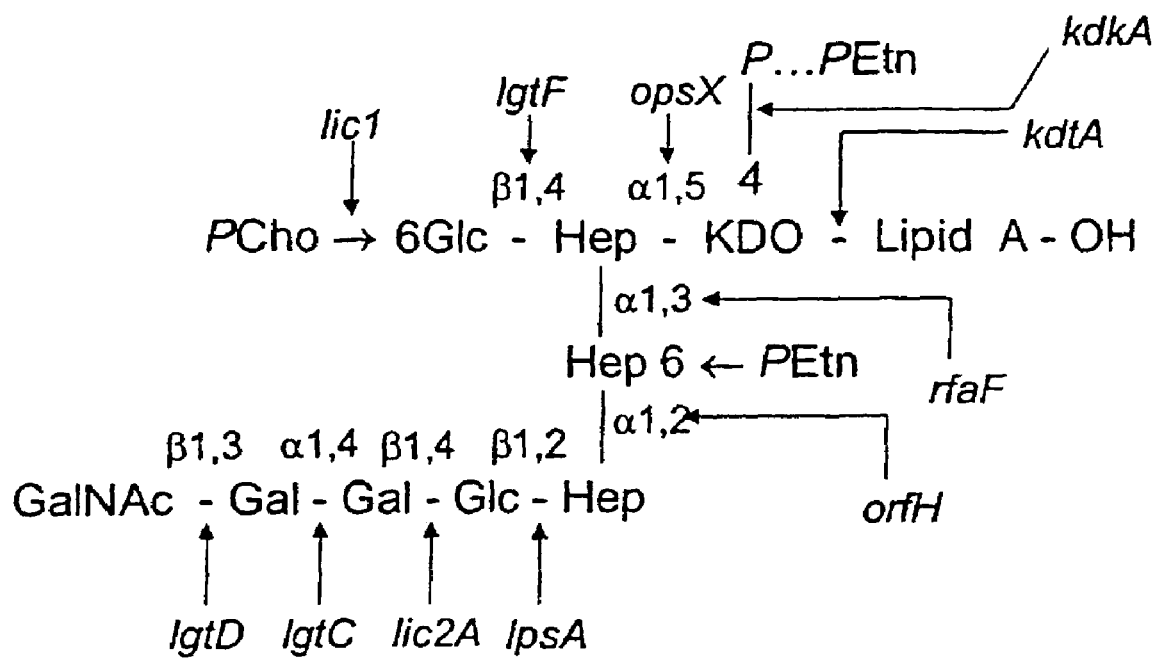
FIG. 7 is a schematic representation of the structure of LPS from *H. influenzae* strain RM118 based on the results of the analysis of Risberg et al. The proposed site of action in LPS biosynthesis of loci characterised in this study are shown, linked by arrows to the relevant saccharide linkage. Phase variable loci are underlined. Represented in the LPS structure: KDO, 2-keto-3-deoxyoctulosonic acid; Hep, L-glycero-D-manno-heptose; Glc, D-glucose; Gal, D-galactose; GalNAc, N-acetylgalactosamine; PEtn, phosphoethanolamine; P, phosphate; Pcho, phosphocholine. For the heptose residues, listed top to bottom are heptose I, heptose II then heptose III.

FIG. 7 summarizes the genes involved in the biosynthesis of the major globotetraose-containing oligosaccharides of LPS in *H. influenzae* Rd which have been identified. Applicant has identified the genes which; are responsible for chain extension from HepI (lgtF) and HepIII (lpsA). Furthermore, some strains of *Haemophilus influenzae* (eg. Eagan and RM7004) elaborate LPS which can show chain extension from HepII. Applicant has shown that a gene in the lic2 locus (orf3) initiates chain extension from HepII. Differential expression of these genes can lead to a manifold of variable oligosaccharide epitopes emanating from the conserved triheptosyl inner-core moiety. Through defined mutations in these genes, Applicant can control not only the degree of complexity that a particular *Haemophilus influenzae* strain expresses, but also the available epitopes on the resulting core region of the LPS. Thus, LPS from *H. influenzae* strains with defined mutations in their biosynthetic machinery provided suitable candidates for developing a broad spectrum LPS-based vaccine. Applicant has determined that this strategy is useful for vaccine design because it provides cross-reactivity against a variety of pathogenic strains of *Haemophilus influenzae*, including non-typeable strains which have hitherto exhibited such LPS variability as to discourage development of vaccines.

Variation in the substitution patterns at HepII and HepIII in the LPS triheptosyl inner-core leads to alternate inner-core oligosaccharide epitopes. The following are examples of useful substitutions and modifications of the inner core region of LPS of *Haemophilus influenzae* which illustrate the invention. These are not intended to be limiting and one of skill in the art will appreciate that other substitutions and modifications are possible in keeping with the teachings of the invention.

Based on genomic and phenotypic analysis of LPS from a collection of NTHi strains, Applicant has identified, for the first time, *Haemophilus influenzae* strains expressing LPS with an alternate inner-core structure in which chain extension occurs from O-3 of HepIII instead of O-2. Homologous lpsA genes mediate the specific addition of β-D-Gal or β-D-Glc to the O-2 or O-3 position of HepIII depending on the strain. Furthermore, some *Haemophilus influenzae* strains express LPS in which HepIII is not substituted by oligosaccharide chains. These findings are detailed in the examples.

The results in the examples confirm the presence of a conserved inner-core element in NTHi. These results also provide for the first time evidence for a new structural motif, namely an alternate substitution site on HepIII. HepIII has earlier been found to be substituted by hexose residues at the O-2-position, and this was found to be the case in NTHi, for example in strains 285 and 1158. In other NTHi strains, for example 176 and 486, this substitution pattern is not observed. Instead, substitution occurs at the O-3 position of HepIII. Surprisingly, it has been shown that the lpsA gene can add a β-D-Glcp in some strains (strain RD, FIG. 9) or a β-D-Galp in others (type b, eg strain Eagan) in a 1,2-linkage to initiate chain extension from HepIII. Applicant has found that a homologue of lpsA is responsible for addition of a β-D-Glcp residue or a β-D-Galp residue in a 1,3-linkage to HepIII.

Another useful modification of the inner-core region relates to the PCho epitope. This is a common feature on surface structures of pathogens residing in the human respiratory tract, including *H. influenzae*. In *H. influenzae* strain Rd, PCho is attached to O-6 of a terminal β-D-Glcp residue at HepI (PCho→6)-β-D-Glcp). In other *H. influenzae* strains, for example type b strain Eagan, PCho is attached to O-6 of a terminal β-D-Galp residue at HepIII. (PCho→6)-β-D-Galp) (Schweda et al. Eur. J. Biochem. 267:3902-3913, 2000). Both of these substitution patterns have been found in NTHi strains. Furthermore, PCho has been found on the terminal α-D-Glcp residue (PCho→6)-α-D-Glcp). The expression and phase variation of the PCho epitope on the *H. influenzae* LPS require the four genes of the lic7 locus (Weiser et al. Infec. Immun. 65:943-950, 1997). These genes have been found on every NTHi strain investigated. Applicant has determined that polymorphism in the licD gene affects the site at which the PCho is added.

The nature of the substitution pattern to the triheptosyl inner-core moiety is relevant to the way in which inner-core epitopes are presented to the immune system and recognised by monoclonal antibodies. For example, Applicant has found that a murine IgG2a monoclonal antibody (L6A9). recognises a LPS inner-core oligosaccharide epitope in strains containing a β-D-Galp residue at O-2 of HepIII, but not when the β-D-Galp residue is absent or attached to the O-3 position. Structural verification of the high molecular weight form is shown in FIG. 1.

As stated above, key biosynthetic genes involved in. *H. influenzae* LPS expression have been identified. This gave Applicant the ability to construct mutant strains of *H. influenzae* that comprise the conserved inner-core moiety, but not oligosaccharide extensions that mimic human tissues structures. The examples set out the results of this procedure.

Applicant has found that oligosaccharides containing the conserved triheptosyl inner-core moiety of *H. influenzae* LPS are immunogenic when formulated as, e.g. protein conjugates, using methods known to those skilled in the art (Gu patent, supra). For example, Applicant has shown that the immunization of mice with an oligosaccharide-protein conjugate comprised of O-deacylated LPS from Hi strain Rdlic1lpsA conjugated with bovine serum albumum (BSA) produces immune serum which is cross reacitve with a majority of LPS samples from a genetically diverse set of NTHi strains (Table 3). O-deacylation of the LPS is achieved by using anhydrous hydrazine. This has the effect of solubilizing the LPS, oligosaccharide for the subsequent conjugation reaction with protein and leads to significant detoxification of the Lipid A component (Gu patent, supra). The O-deacylated LPS is conjugated via the carboxyl group of the Kdo moiety according to methods known to those skilled in the art (Gu patent, supra). Mice were given a final intraperitoneal boost with O-deacylated LPS from Hi strain 1003lic1lpsA (see the examples). Mouse immune sera from this experiment reacted with LPS from NTHi strains which have multiple chain extensions from the inner core.

Rdlic1lpsA LPS elaborates LPS that is representative of the conserved triheptosyl inner-core moiety, and contains minor glycoforms having lacto-N-neotetraose (LNnT)-containing oligosaccharide chain extensions. This is evident from the reactivity with Mab LLA5 (Table 4). The Rdlic1lpsA O-deacylated LPS-BSA conjugate also showed reactivity with Mab LLA5 as well as the inner-core Mab, LLA4. NTHi strain 1003 does not elaborate LPS having LNnT containing oligosaccharide chains. Applicant determined this by structural, genetic and immunochemical analyses. LPS from this strain does not react with LLA5, does not contain the rfb genetic locus. The double mutant, 1003lic1lpsA expresses LPS having the conserved inner-core moiety with no chain extensions. It is recognized by Mab LLA4.

The above shows that the conserved inner-core moiety of the *H. influenzae* LPS (which is present in Rdlic1lpsA for example) can elicit an immune response that is cross reactive with LPS from strains representative of the diversity of the bacterium. Lactose, LNnT and their sialylated analogues are oligosaccharide structures that are found on human tissues. To develop a LPS based vaccine, it is therefore preferable to ensure these oligosaccharide extensions are not present in the vaccine formulation. The above experiments provide evidence that these oligosaccharide extensions are common throughout *H. influenzae* strains, and that Applicant has taught the methodology to identify them and to construct strains without them.

By the same means, other mutant strains of Hi can be constructed with substitutions to or modifications of the conserved triheptosyl inner-core moiety of LPS which result in epitopes which elicit a broad spectrum immune response to Hi, including NTHi, and/or which elicit an improved immune response because of mimicry of, or avoidance of mimicry of animal tissues.

Vaccination methods for treating or preventing infection in a mammal comprise use of a vaccine formulation of the invention to be administered by any conventional route, particularly to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine formulation. Treatment may be effected in a single dose or repeated at intervals. The appropriate dosage depends on various parameters understood by skilled artisans such as the vaccine formulation itself, the route of administration or the condition of the mammal to be vaccinated (weight, age and the like).

Standard laboratory techniques for preparing and purifying lipopolysaccharides are used in the preparation of lipopolysaccharide therapeutics of the invention. For use as a vaccine, a lipopolysaccharide of the invention is formulated according to various methods outlined below.

Since the Lipid A component of LPS can render it toxic, preferably the LPS immunogen is detoxifed. Although the use of hydrazine for detoxification of LPS from NTHi is described herein, the use of any reagent or enzyme capable of removing ester-linked fatty acids from Lipid A is within the scope of the present invention. Dried LPS from the selected strain of NTHi is suspended in liquid anhydrous hydrazine at a temperature of between 1° C. and 100° C., preferably between 25° C. and 75° C., more preferably about 37° C., for a period between 1 hour and 24 hours, most preferably for a period of about 2-3 hours. After removal of ester-linked fatty acids, DLPS is conjugated to the linker adipic acid dihydrazide (ADH) prior to conjugation to the immunogenic carrier proteins TT or NTHi HMPs. Although ADH is the preferred linker, the use of any linker capable of stably and efficiently conjugating dLPS to an immunogenic carrier protein is contemplated. The use of linkers is well known in the conjugate vaccine field (see Dick et al., Conjugate Vaccines, J. M. Cruse and R. E. Lewis., Jr., eds., Karger, N.Y., pp. 48-114).

dLPS may be directly covalently bonded to the, carrier. This may be accomplished, for example, by using the cross-linking reagent glutaraldehyde. However, in a preferred embodiment, dLPS and the carrier are separated by a linker. Presence of a linker promotes optimum-immunogenicity of the conjugate and more efficient coupling of the dLPS with the carrier. Linkers separate the two antigenic components by chains whose length and flexibility can be adjusted as desired. Between the bifunctional sites, the chains can contain a variety of structural features, including heteroatoms and cleavage sites. Linkers also permit corresponding increases in translational and rotational characteristics of the antigens, increasing access of the binding sites to soluble antibodies. Besides ADH, suitable linkers include, for example, heterodifunctional linkers such as epsilon. aminohexanoic acid, chlorohexanol dimethyl acetal, D-glucuronolactone and p-nitrophenyl amine. Coupling reagents contemplated for use in the present invention include hydroxysuccinimides and carbodiimides. Many other linkers and coupling reagents known to those of ordinary skill in the art are also suitable for use in the invention. Such compounds are discussed in detail by Dick et al., supra.

The presence of a carrier increases the immmunogenicity of the polysaccharide. In addition, antibodies raised against the carrier are medically beneficial. Polymeric immunogenic carriers can be a natural or synthetic material containing a primary and/or secondary amino group, an azido group or a carboxyl group. The carrier may be water soluble or insoluble.

Any one of a variety of immunogenic carrier proteins may be used in the conjugate vaccine of the present invention. Such classes of proteins include pili, outer membrane proteins and excreted toxins of pathogenic bacteria, nontoxic or "toxoid" forms of such excreted toxins, nontoxic proteins antigenically similar to bacterial toxins (cross-reacting materials or CRMs) and other proteins. Nonlimiting examples of bacterial toxoids contemplated for use in the present invention include tetanus toxin/toxoid, diphtheria toxin/toxoid, detoxified *P. aeruginosa* toxin A, cholera toxin/toxoid, pertussis toxin/toxoid and *Clostridium perfringens* exotoxins/toxoid. The toxoid forms of these bacterial toxins is preferred. The use of viral proteins (i.e. hepatitis B surface/core antigens; rotavirus VP 7 protein and respiratory syncytial virus F and G proteins) is also contemplated.

CRMs include $CRM_{197}$, antigenically equivalent to diphtheria toxin (Pappenheimer et al., Immunochem., 9:891-906, 1972) and CRM3201, a genetically manipulated variant of pertussis toxin (Black et al., Science, 240:656-659, 1988). The use of immunogenic carrier proteins from non-mammalian sources including keyhole limpet hemocyanin, horseshoe crab hemocyanin and plant edestin is also within the scope of the invention.

There are many coupling methods which can be envisioned for dLPS-protein conjugates. dLPS can be selectively activated by 1-methyl-3-(3-dimethylaminopropyl) carbodiimide (EDC)-mediated ADH derivatization of the terminal 3-deoxy-D-manno-2-octulosonic acid (Kdo) group of dLPS, followed by EDC-mediated coupling to TT. Alternatively, another method for producing the instantconjugates involves cystamine derivatization of dLPS, by, for example, EDC-mediated derivatization, followed by disulfide conjugation to N-succimidyl-3-(2-pyridyldithio) propionate-derivatized protein. Other methods well known in the art for effecting conjugation of oligosaccharides to immunogenic carrier proteins are also within the scope of the invention. Such methods are described in, for example, U.S. Pat. Nos. 5,153,312 and 5,204,098; EP 0 497 525; and EP 0 245 045.

The molar ratio of ADH to dLPS in the reaction mixture is typically between about 10:1 and about 250:1. A molar excess of ADH is used to ensure more efficient coupling and to limit dLPS-dLPS coupling. In a preferred embodiment, the molar ratio is between about 50:1 and about 150:1; in a most preferred embodiment, the molar ratio is about 100:1. Similar ratios of AH-dLPS to both TT and HMP in the reaction mixture are also contemplated. In a preferred embodiment, one ADH per dLPS is present in the AH-dLPS conjugate. In another preferred embodiment, in the final dLPS-carrier protein conjugate, the molar ratio of dLPS to carrier is between about 15 and about 75, preferably between about 25 and about 50.

Immunogenicity of the conjugates in both mice and rabbits is enhanced by the use of monophosphoryl Lipid A plus trehalose dimycolate (Ribi-700™; Ribi Immunochemical Research, Hamilton, Mont.) as an adjuvant. Although this adjuvant is not approved for use in humans, the skilled artisan will appreciate that other well known standard adjuvants may be used in the invention, including aluminum compounds (i.e. alum), chemically-modified lipopolysaccharide, suspensions of killed *Bordetella pertussis*, N-acetylmuramyl-L-alanyl-D-glutamine and other adjuvants known to one of ordinary skill in the art. The use of aluminum compounds is particularly preferred. Such adjuvants are described by Warren et. al. (Ann. Rev. Biochem., 4:369-388, 1986).

The dLPS-carrier protein conjugates for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

The conjugate vaccine of the invention may be in soluble or microparticular form, or may be incorporated into microspheres or microvesicles, including liposomes. Although various routes of vaccine administration including, for example, intramuscular, subcutaneous, intraperitoneal and intraarterial are contemplated, the preferred route is intramuscular administration. In a preferred embodiment, the dosage of the conjugate administered will range from about 10 μg to about 50 μg. In a more preferred embodiment, the amount administered will be between about 20 μg and about 40 μg. In a most preferred embodiment, the amount administered is about 25 μg. Greater doses may be administered on the basis of body weight. The exact dosage can be determined by routine dose/response protocols known to one of ordinary skill in the art.

The vaccine of the invention may be administered to warm-blooded mammals of any age and are adapted to induce active immunization in young mammals, particularly humans, against otitis media and respiratory infections caused by NTHi. As a childhood vaccine, the conjugate is administered at about 2 to 4 months of age. Typically, two booster injections of between about 10 μg and about 25 μg are administered at about 2 and again about 13 months after the initial injection. Alternatively, three booster injections are given at 2, 4 and 16 months after the initial injection.

The IgG antibodies elicited by systemic administration of the conjugate vaccine will transfer to local mucosa and inactivate NTHi inoculum on mucosal surfaces (i.e., nasal passages). Secretory IgA will also play a role in mucosal immunity if the conjugate vaccine is administered to the mucosa (i.e. intranasally). Thus, the conjugate vaccine will prevent local, as well as systemic, NTHi infection.

The examples describe conjugate vaccines using NTHi Rdlic11psA. Vaccines from other NTHi strains are within the scope of the present invention and are made using the same techniques. NTHi strain Rdlic11psA. Other clinically relevant NTHi strains contemplated as sources of dLPS for generation of a dLPS-carrier conjugate vaccine include strains 9274, 2019, 1479, 5657 and 7502 (type III, II, I, IV and V, respectively), as well as strains from the Finnish Collection referred to herein. These strains, as well as strain 2019, are described by Campagnari et al. (Infect Immun., 55:882-887, 1987), Patrick et al. (Infect Immun., 55:2902-2911, 1987), and Hood et al., (Mol. Microbiol 33:679-692, 1999), and are generally available from the research community.

A multivalent vaccine comprising a mixture of conjugates, each having a dLPS from a different NTHi strain, is also within the scope of the invention. A person of ordinary skill in the art will appreciate that LPS from these other clinically relevant strains may be detoxified by removal of fatty acids therefrom, for example as described in Gu et al. (U.S. Pat. No. 6,207,157). In a preferred embodiment, the dLPS moieties thus obtained are at least about 5,000 fold less toxic than LPS itself. In a particularly preferred embodiment, the dLPSs are at least about 10,000 fold less toxic than dLPS. Determination of toxicity may be performed, for example, as described in Gu et al. (U.S. Pat. No. 6,207,157).

Live vaccines available in the art include viral vectors such as adenoviruses, alphaviruses and poxviruses as well as bacterial vectors, e.g., *Shigella, Salmonella, Vibrio cholerae, Lactobacillus*, Bacille bilié de Calmette-Guérin (BCG), and *Streptococcus*.

Attenuated *Salmonella typhimurium* strains, genetically engineered for recombinant expression of heterologous antigens or not, and their use as oral vaccines are described in WO 92/11361. Preferred routes of administration include all mucosal routes; most preferably, these vectors are administered intranasally or orally.

Other bacterial strains used as vaccines are described for *Shigella flexneri* in High et al., EMBO 11:1991, 1992 and Sizemore et al., Science 270:299, 1995; for *Streptococcus gordonii* in Medaglini et al., Proc. Natl. Acad. Sci. USA 92:6868, 1995; and for Bacille Calmette Guerin in Flynn J. L., Cell. Mol. Biol. 40 (suppl. I):31, 1994 and in WO 88/06626, WO 90/00594, WO 91/13157, WO 92/01796, and WO 92/21376.

An alternative formulation utilizes the vaccine in association with agents that assist in cellular uptake. Examples of such agents are (i) chemicals that modify cellular permeability, such as bupivacaine (see, e.g., WO 94/16737), (ii) liposomes for encapsulation of the lipopolysaccharide, the vaccine, or partially de-acylated LPS, or (iii) cationic lipids or silica, gold, or tungsten microparticles which associate themselves with the lipopolysaccharides.

Anionic and neutral liposomes are well known in the art (see, e.g., Liposomes: A Practical Approach, RPC New Ed, IRL press (1990), for a detailed description of methods for making liposomes) and are useful for delivering a large range of products, including lipopolysaccharide-based vaccines. For use in a composition of the invention, in one embodiment, a lipopolysaccharide-based vaccine or derivative thereof is formulated into or with liposomes, preferably neutral or anionic liposomes, microspheres, ISCOMS, or virus-like-particles (VLPs) to facilitate delivery and/or enhance the immune response.

Cationic lipids are also known in the art. Such lipids include Lipofectin™ also known as DOTMA (N-[1-(2,3-dioleyloxy)propyl]-N,N,N-trimethylammonium chloride), DOTAP (1,2-bis(oleyloxy)-3-(trimethylammonio) propane), DDAB (dimethyldioctadecylammonium bromide), DOGS (dioctadecylamidologlycyl spermine) and cholesterol derivatives such as DC-Chol (3-β-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928.

The route of administration is any conventional route used in the vaccine field. As general guidance, a lipopolysaccharide-based vaccine of the invention is administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of administration route depends upon a number of parameters, such as the formulation that is selected, and the adjuvant associated with the lipopolysaccharide. A lipopolysaccharide-based vaccine formulated in association with bupivacaine may be advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A lipopolysaccharide in a naked form can advantageously be administered via the intramuscular, intradermal, or sub-cutaneous routes. If a mucosal adjuvant is used, the intranasal or oral route is preferred. If a lipid formulation or an aluminum compound is used, the parenteral route is preferred with the sub-cutaneous or intramuscular route being most preferred. The choice also depends upon the nature of the vaccine agent.

Therapeutic or prophylactic efficacy of a vaccine formulation of the invention can be evaluated as described below. Another aspect of the invention provides (i) a composition comprising a lipopolysaccharide-based vaccine of the invention together with a diluent or carrier; specifically (ii) a pharmaceutical composition containing a therapeutically or prophylactically effective amount of a lipopolysaccharide-based vaccine of the invention; (iii) a method for inducing an immune response against *Haemophilus influenzae* in a mammal, by administering to the mammal an immunogenically effective amount of a lipopolysaccharide of the invention to elicit a protective immune response to *Haemophilus influenzae*; and particularly, (iv) a method for preventing and/or treating a *Haemophilus influenzae* infection, by administering a prophylactic or therapeutic amount of a lipopolysaccharide of the invention to an infected individual. Additionally, the invention encompasses the use of a lipopolysaccharide-based vaccine of the invention in the preparation of a medicament for preventing and/or treating *Haemophilus influenzae* infection.

As used herein, the composition of the invention contains one or several lipopolysaccharides or derivatives of the invention. The composition optionally contains at least one additional *Haemophilus influenzae* antigen, or a subunit, fragment, homolog, mutant, or derivative thereof.

In one embodiment, the lipopolysaccharide-based vaccine, composition or treatment is free of adjuvant, specifically adjuvants commonly or specifically used in rodents. The lipopolysaccharide-based vaccine, composition or treatment may be used to treat disorders whose symptoms are caused or aggravated at least in part by *Haemophilus influenzae* infection, and includes such disorders as otitis media, respiratory infection, meningtidis and pneumonia. Preferred lipopolysaccharide compositions include those formulated for in vivo administration to an animal, preferably a human, to confer protection or treatment against disease caused by *Haemophilus influenzae*. Also preferred are compositions formulated as a microparticle, capsule, or liposome.

Alternatively, the vaccine formulation may further contain an adjuvant, preferably an adjuvant appropriate for human or veterinary use and which preferably excludes rodent-specific adjuvants. If so, a systemic adjuvant that does not require concomitant administration in order to exhibit an adjuvant effect is preferable such as, e.g., QS21, which is described in U.S. Pat. No. 5,057,546. A number of adjuvants are known to those skilled in the art. Preferred adjuvants are selected as provided below.

In one embodiment, adjuvants other than liposomes and the like are also used and are known in the art. Adjuvants may protect the antigen from rapid dispersal by sequestering it in a local deposit, or they may contain substances that stimulate the host to secrete factors that are chemotactic for macrophages and other components of the immune system. An appropriate selection can conventionally be made by those skilled in the art, for example, from those described herein.

Treatment is achieved in a single dose or repeated as necessary at intervals, as can be determined readily by one skilled in the art. For example, a priming dose is followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention is administered by a mucosal route in an amount from about 10 μg to about 500 mg, preferably from about 1 mg to about 200 mg. For the parenteral route of administration, the dose usually does not exceed about 1 mg, preferably about 100 μg.

Adjuvants useful in any of the vaccine compositions described above are as follows. Adjuvants for parenteral administration include aluminum compounds, such as aluminum hydroxide, aluminum phosphate, and aluminum hydroxy phosphate. The antigen is precipitated with, or adsorbed onto, the aluminum compound according to standard protocols. Other adjuvants, such as RIBI (ImmunoChem, Hamilton, Mont.), are used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof such as a purified preparation of native cholera toxin subunit B (CTB). Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/06627 (Arg-192-Gly LT mutant), and WO 95/34323 (Arg-9-Lys and Glu-129-Gly PT mutant). Additional LT mutants that are used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium,* or *Shigella flexneri*; saponins, or polylactide glycolide (PLGA) microspheres, may also be used in mucosal administration.

Adjuvants useful for both mucosal and parenteral administrations include polyphosphazene (WO 95/02415), DC-chol (3-β-(N-(N',N'-dimethyl aminomethane)-carbamoyl) cholesterol; U.S. Pat. No. 5,283,185 and WO 96/14831) and QS-21 (WO 88/09336).

Any pharmaceutical composition of the invention containing a lipopolysaccharide, or an antibody of the invention, is manufactured in a conventional manner. In particular, it is formulated with a pharmaceutically acceptable diluent or carrier, e.g., water or a saline solution such as phosphate buffer saline. In general, a diluent or carrier is selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF (National Formulary).

The invention also includes methods in which *Haemophilus influenzae* infection are treated by oral administration of a *Haemophilus influenzae* lipopolysaccharide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids). In addition, compounds containing more than one of the above-listed components coupled together are used. The invention also includes compositions for carrying out these methods, i.e., compositions containing a *Haemophilus influenzae* antigen (or antigens) of the invention, an adjuvant, and one or more of the above-listed compounds, in a pharmaceutically acceptable carrier or diluent.

Amounts of the above-listed compounds used in the methods and compositions of the invention are readily determined by one skilled in the art. Treatment/immunization schedules are also known and readily designed by one skilled in the art. For example, the non-vaccine components can be administered on days 1-14, and the vaccine antigen+ adjuvant can be administered on days 7, 14, 21, and 28.

Throughout this application, various references are referred to in parenthesis to describe more fully the state of the art to which this invention pertains. The disclosures of these references are hereby incorporated by reference into the present disclosure.

Biological Deposits

Certain strains of *Haemophilus influenzae* that are described and referred to herein have been deposited with the International Depositary Authority of Canada (IDAC) located at Bureau of Microbiology, Health Canada, 1015 Arlington Street, Winnipeg, Manitoba, Canada R3E 3R2. The deposits have been made pursuant to the provisions of the Budapest Treaty. The deposit information is:

*Haemophilus influenzae* strain Rd lic1 lpsA was deposited on Aug. 25, 2001 under accession number IDAC 250801-1.

*Haemophilus influenzae* strain 1003 lic1 lpsA was deposited on Aug. 25, 2001 under accession number IDAC 250801-2.

The invention described and claimed herein is not limited in scope by the biological materials deposited, and the deposited biological material is intended only as an illustration of embodiments of the invention.

EXAMPLES

The following examples illustrate preferred embodiments of aspects of the invention, and are not intended to limit the scope of the invention.

Example 1

Hi LPS Mutant Strains

Bacterial strains and Culture Conditions.

The *H. influenzae* Rd strain was originally obtained from Alexander and Leidy (Alexander et al., J. Exp. Med. 93:345-359, 1951) by Herriot. It was given to H. O. Smith who named the strain KW-20 and used it in the genome sequencing project (Fleischmann et al., Science 269:496-512, 1995). This same strain obtained from the Smith laboratory has been used by Applicant (RM118). The genotypes of mutants derived from this strain are listed in Table 2. *H. influenzae* strains were grown at 37° C. in brain heart infusion (BHI) broth supplemented with haemin (10 μg/ml) and NAD (2 μg/ml). For selection after transformation, kanamycin (10 μg/ml) was added to the growth medium.

*Escherichia coli* strain DH5α was used to propagate cloned PCR products and gene constructs and was grown at 37° C. in Luria-Bertani (LB) broth supplemented with ampicillin (100 μg/ml) or kanamycin (50 μg/ml) as required (Sambrook et al. Molecular cloning; A laboratory manual, $2^{nd}$ Ed., 1989, Cold Spring Harbor Laboratory, Cold Spring Harbor, N.Y.).

Identification of LPS Related Genes from the *H. influenzae* Genome Sequence.

Putative LPS biosynthetic genes had been previously identified by an in silico search of the *H. influenzae* genome sequence with heterologous sequences of LPS biosynthetic genes from a wide range of organisms obtained from publicly available data bases (Hood et al. Mol. Microbiol. 22:951-965, 1996). The RM118lgtF locus (HI0653) was identified by searching the Institute for Genomic Research (TIGR) *H. influenzae* strain Rd sequence database
www.tigr.org/tdb/CMR/ghi/htmls/SplashPage.html
for matches with the LgtF protein sequence from *N. meningitidis* (GenBank Accession No. U58765).

Recombinant DNA Methodology, Cloning and Mutation

Restriction endonucleases and DNA modifying enzymes were obtained from Boehringer Mannheim and used according to the manufacturer's instructions.

Plasmid DNA preparation, Southern blotting and hybridization analysis were performed as described by. Sambrook et al., (Molecular cloning; A laboratory manual, $2^{nd}$ Ed., 1989, Cold Spring Harbor Laboratory, Cold Spring Harbor, N.Y.). Chromosomal DNA was prepared from *Haemophilus* by the method described elsewhere (High et al., Mol. Microbiol. 9:1275-1282, 1993).

Apart from lgtF, putative *H. influenzae* LPS biosynthetic genes were cloned and mutated as previously reported (Hood et al., Mol. Microbiol. 22:951-965, 1996). For the lgtF locus, oligonucleotide primers, lgtFa (5'-TGGTGGTGGGCAAGACGC-3')

and lgtFb (5'-AGCCTGAATTCGACAGCC-3')

were designed from the strain Rd genome sequence to amplify a 1461 bp fragment including HI0653 by the polymerase chain reaction (PCR). PCR conditions were for 1 minute periods of denaturation (94° C.), annealing (50° C.)

and polymerization (72° C.) for 30 cycles. 1 μl of PCR product was ligated with 50 ng of plasmid pT7Blue (Novagen) and transformed into E. coli strain DH5α. Recombinant plasmids were prepared from transformants then confirmed by restriction endonuclease digestion and sequencing from plasmid specific primers (Hood et al., Mol. Microbiol. 22:951-965, 1996). The lgtF gene was inactivated by inserting a kanamycin resistance cassette (released by digestion with EcoR1 from pUC4Kan, Pharmacia) into a MunI restriction site 257 bp inside the 5' end of HI0653 to give plasmid pDQ1.

Construction of Mutant Strains 2-3 μg of linearised plasmid, containing mutated LPS biosynthetic genes, were used to transform H. influenzae strain RM118 by the MIV procedure (Herriot et al., J. Bacteriol. 101:517-524, 1970) and transformants were selected on kanamycin. To construct strain RM118lic1, RM118 was transformed with 5 μg of sheared chromosomal DNA isolated from the corresponding RM153 mutant. Strain RM118lic2A was constructed by transformation of RM118 with 1 μg of a PCR product including lic2A and the adjacent gene ksgA amplified from strain RM153lic2A. PCR used the primers L2A

5'-CTCCATATTACATAAT-3' and L2D

5'-AAACACTTAGGCCATACG-3' under conditions as described above. All transformants were checked by re-culturing on appropriate BHI/antibiotic plates then were confirmed as mutants by PCR amplification and/or Southern blotting/hybridisation of endonuclease digested chromosomal DNA.

lpsAlic1 mutant. The lic1 locus was identified by transfer of a bank of DNA fragments cloned from strain RM7004, which expresses LPS epitopes recognised by monoclonal antibodies (mAb) 4C4, 6A2 and 12D9, into strain RM118 which naturally expresses none of these in epitopes in its LPS. A cloned 4.4 kb fragment of DNA conferring reactivity to mAbs 6A2 and 12D9 was sequenced and 4 open reading frames (ORFs) were identified. These 4 ORFs were knocked out together by deletion of a 2.7 kb ClaI/EcoRV fragment from the cloned DNA and replacement with a tetracycline resistance cassette from plasmid pHVT1. This construct was used to make a lic1 mutation in strain RM7004 then strain RM118 by homologous recombination after transformation.

The lpsA gene was identified from the genome sequence of strain Rd as a homologue of a gene encoding a glycosyltransferase in Pasteurella haemolytica. The gene was amplified by the polymerase chain reaction (PCR) using primers designed from the Rd genome sequence. The PCR product was cloned into plasmid pT7Blue then the gene was disrupted by digestion with NsiI and insertion of a kanamycin resistance cassette derived from pUC4kan, by digestion with PstI. The resulting plasmid was linearised then used to transform strains RM118 and NTHi 1003. The transformants were checked by PCR to confirm mutants.

The double mutant strains RM118lpsAlic1 (referred to interchangeably as RdlpsAlic1 or Rdlic1lpsA) and 1003psAlic1 (referred to interchangeably as 1003lic1lpsA) were constructed by transforming each of the RM118 and 1003 lpsA mutants with chromosomal DNA derived from the RM118lic1 mutant strain. The double mutant strains were confirmed by PCR analysis of, the relevant loci and the backgrounds of the strains were confirmed by restriction enzyme digestion and comparison of the patterns of the DNA fragments on gels with the relevant wild type strains.

Strains were subsequently checked using a number of mAbs, each specific for particular LPS epitopes. In each case the RM118 and 1003 lpsAlic1 double mutant strains had lost reactivity to mAb TEPC-15, an antibody specific for phosphocholine, when compared to wild type. Phosphocholine incorporation into H. influenzae LPS is dependent upon the lic1 locus. The LPS derived from the mutant strains was also fractionated on polyacrylamide gels and compared to the relevant wild type LPS. In each case the double mutant strain had LPS which was truncated when compared to that from wild type strains.

Analysis of Lipopolysaccharide by Immunoblotting

The reactivity of wild-type and mutant strains of H. influenzae strain RM118 to LPS specific monoclonal antibodies was analyzed as described by Roche et al., (FEMS Microbiol. Lett. 120:279-284, 1994).

Analysis of Lipopolysaccharide by Electrophoresis

The patterns of LPS isolated from wild type and mutant strains were determined after fractionation by tricine-SDS-polyacrylamide gel electrophoresis (T-SDS-PAGE) (Lesse et al., J. Immunolog. Methods 126:109-117, 1990) as described previously (Hood et al., Mol. Microbiol. 22:951-965, 1996).

Structural Fingerprinting of Lipopolysaccharides

Cells from 10 L batch cultures (10 lots of 1 L) were harvested after overnight growth, LPS was extracted by the hot phenol-water method (Westphal et al., Meth. Carbohydr. Chem. 5:83-91, 1965), followed by ethanol precipitation as described by Thibault and Richards, 2000). LPS was purified by repeated ultracentrifugation (105 000 g, 4° C., 2×5 h) and samples were analysed as their O-deacylated derivatives (LPS-OH). O-deacylation was achieved by mixing the LPS (1-10 mg) with anhydrous hydrazine (0.2-1.0 ml) at 37° C. for 1 h as previously described (Hoist et al., Eur. J. Biochem. 214:703-710, 1993) Sugars were identified by gas-liquid chromatography-mass spectrometry (GLC-MS) as their alditol acetates as previously described (Jarosik et al., Infect. Immun. 62:4861-4867, 1994). Linkage analysis was accomplished following acetylation of the oligosaccharides with acetic anhydride (0.5 ml) and 4-dimethylaminopyridine (0.5 mg) at room temperature for 24 h. Peracetylated material was then treated with methyl iodide in dimethylsulfoxide in the presence of lithium methylsulfinylmethanide to afford the methylated oligosaccharides which were recovered using a SepPak™ C18 cartridge and subjected to sugar analysis (Blakeney et al, Carbohydr. Res. 140:319-324, 1985). The relative proportions of the various alditol acetates and partially methylated alditol acetates obtained in sugar and methylation analyses were measured from the detector response of the GLC-MS and are uncorrected. GLC-MS was carried out with a Delsi Di200™ chromatograph equipped with a NERMAG R10-10H™ quadrupole mass spectrometer or with a Varian Iontrap™ system using a DB-5 fused silica capillary column (25 m×0.25 mm×0.25 μm) and a temperature gradient of 160° C. (1 mm)→250° C. at 3° C./min. Electrospray ionization-mass spectrometry (ESI-MS) was performed on a VG Quattro™ Mass Spectrometer (Micromass, Manchester, UK) in the negative-ion mode. Samples were dissolved in water and then mixed in a 1:1 ratio with 50% aqueous acetonitrile containing 1% acetic acid. Sample solutions were injected via a syringe pump into a running solvent of $H_2O:CH_3CN$ (1:1) at a flow rate of 5 μL/min. One-dimensional (1D) $^1H$ NMR spectra were recorded at 500 MHz for solutions in deuterium oxide at 22° C., after several lyophylizations with $D_2O$, on a Bruker AMX 500™ spectrometer. To enhance spectral resolution, perdeutero-EDTA (2 mM) and perdeutero-SDS (10 mg/ml) were added to the $D_2O$ solutions (Risberg et al., Eur. J. Biochem. 243:701-707, 1997). Chemical shifts are referenced to the methyl proton resonance (δ; 2.225 ppm) of internal acetone.

Analysis of Enzymatic Activity from LgtC and LgtD

The enzyme encoded by lgtD was assayed with the synthetic acceptor FCHASE-$P^k$ using capillary electrophoresis for detection of the product. Capillary electrophoresis was performed essentially as described previously (Wakarchuk et al., J. Biol. Chem. 271:1916-1917, 1996). FCHASE-$P^k$ was synthesised from FCHASE-Lac using the *Neisseria meningitidis* LgtC enzyme as previously described (Wakarchuk et al., Protein Eng. 11:295-302, 1998). The reaction conditions were 0.5 mM acceptor, 1 mM UDP-GalNAc, 50 mM HEPES-NaOH pH 7.0, 10 mM $MgCl_2$, 10 mM $MnCl_2$. The extract was made by sonicating the cells, and then collecting the membrane fraction by centrifugation at 100,000×g for 30 minutes. Both RM118 and the mutant RM118:lgtD were analysed. The small amount of product was isolated by TLC as previously described (Wakarchuk et al., J. Biol. Chem. 271:1916-1917, 1996). Because the conversion to product was small, some of the starting material was also isolated with it. The recovered mixture was divided into 2 equal parts and then treated with β-hexosaminidase as recommended by the enzyme supplier (NEB). The product of the LgtD reaction was shown to have β-anomeric specificity by digestion with β-hexosaminidase.

Activity for LgtC was below the limit of detection in extracts of RM118, so the gene was cloned into an expression vector and activity was assayed in *E. coli*. The gene was amplified by PCR (as described above) using primers lgtCa

5' GGG GGG CAT ATG GGA CGG ACT GTC AGT CAG ACA ATG and lgtCb

5' GGG GGG GTC GAC TCA TTA ATT ATC TTT TAT TCT CTT TCT TAATC

The gene was then inserted into pCWori plus at the NdeI and SalI sites similar to what was described for lgtC from *N. meningitidis* (Wakarchuk, et al., Protein Eng. 11:295-302, 1998). Crude sonicated extracts of the recombinant clone were assayed with 1 mM FCHASE-Lac, 1 mM UDP-Gal, 10 mM $MnCl_2$, 5 mM DTT, 50 mM HEPES pH 7.5. The enzyme was shown to be unstable in *E. coli* and needed to be assayed within a few hours of when the extracts were made (data not shown). The product of the enzyme reaction was analyzed by specific glycosidase digestion, mass spectrometry and co-chromatography with authentic FCHASE-$P^K$ (data not shown).

Construction and Screening of Mutant Strains

The set of mutants prepared as above was used to investigate in detail the genetic basis of the biosynthesis of the oligosaccharide portion of LPS from *H. influenzae* strain RM118, the index strain from which the complete genome sequence was derived. Table 2 lists the genes which have been investigated. The DNA constructs used to mutate the majority of these genes have been previously reported (Hood et al., Mol. Microbiol. 22:951-965, 1996). Each construct consisted of a plasmid vector into which a putative LPS gene, with a kanamycin resistance gene inserted within the 5' end (first third) of the predicted reading frame, was cloned. There was no obvious candidate gene responsible for adding the glucose to the first heptose (HepI). Searching the Rd genome sequence data base with the lgtF sequence from *Neisseria* gave a match (31% identify over 247 amino acids) to reading frame HI0653. lgtF was amplified by PCR from chromosomal DNA of strains RM118 and RM153. The cloned product from strain RM118 was inactivated by insertion of a kanamycin cassette to give plasmid pDQ1 and used to transform *H. influenzae* strains. lic1 and lic2A are phase variable LPS biosynthetic loci (High et al., Mol. Microbiol. 9:1275-1282, 1993, Weiser, et al., Cell 59:657-665, 1989). lic1 has been shown to be involved in the addition of PCho groups to *H. influenzae* LPS (Weiser, et al. Infect. Immun. 65:943-950, 1997). For each locus, strain RM118 was transformed using the mutated gene constructs ($10-10^5$ transformants/μg input DNA). For most loci, RM118 was the source of DNA that had been cloned but in several instances DNA derived from strain RM153 was used as donor with no change in transformation efficiency. Genes responsible for the synthesis of Kdo, the first sugar added to lipid A (kdsA, kdsB) and the Kdo transferase (kdtA) have been identified from the genome sequence (Fleischmann et al., Science 269:496-512, 1995). Attempts to construct strains mutated in the kdta gene, using a variety of plasmid constructs failed to yield any transformants. This is similar to findings with type b strains (Hood et al., Mol. Microbiol. 22:951-965, 1996) and is assumed to be due to non-viability of this mutant. LPS isolated from RM118 and the isogenic mutant strains was analysed by T-SDS-PAGE (data not shown). Strains mutated in genes most likely encoding glycosyltransferases for RM118 oligosaccharide synthesis, and which showed an altered pattern of LPS bands when compared to wild type by T-SDS-PAGE (FIG. 2), were selected for detailed structural analysis of their LPS as described below. A mutant in which the lic1 locus is inactivated was also investigated.

Structural Characterization of LPS

Figure 2:
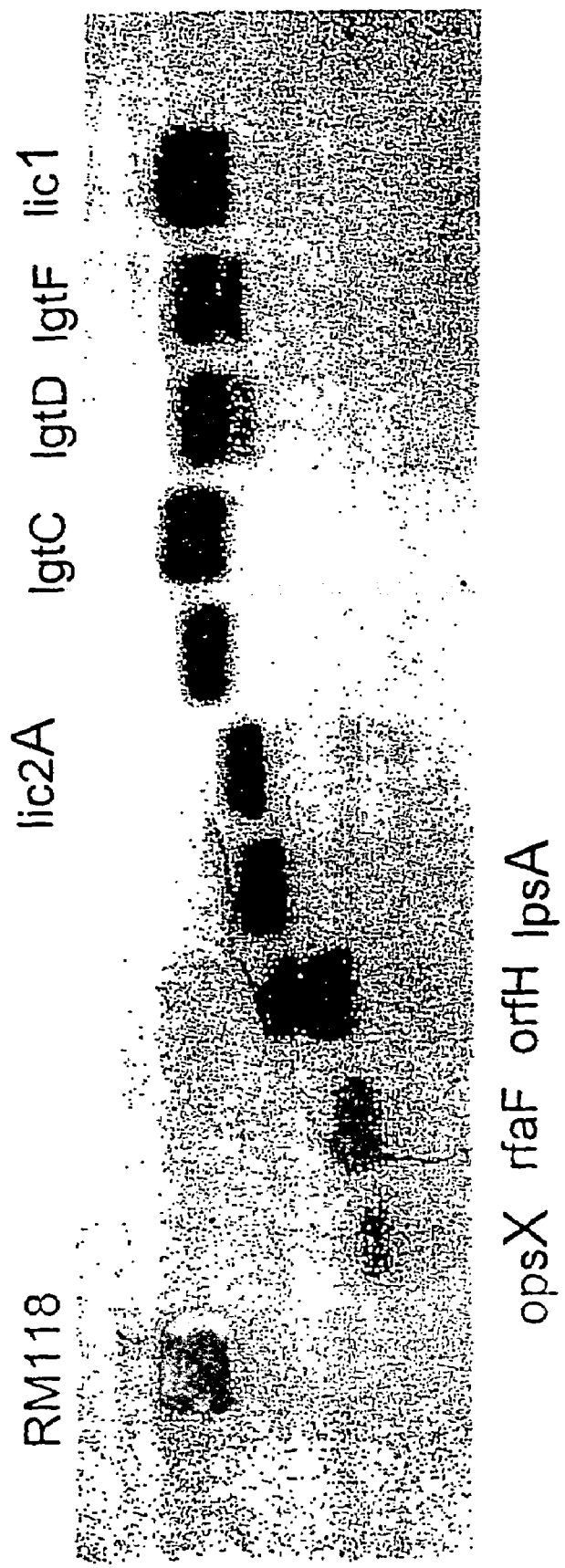
FIG. 2 is the electrophoretic gel-migration patterns after T-SDS-PAGE of LPS purified from RM118 wild type and strains mutated in putative glycosyltransferase genes, wherein RM118 corresponds to the wild type LPS and the isogenic mutants are listed by the relevant LPS gene.

Analysis of LPS from strain RM118 by T-SDS-PAGE showed a heterogeneous pattern of bands corresponding in electrophoretic mobility to populations of low-molecular-mass LPS composed of lipid A and oligosaccharide components differing in the number of attached sugar residues (FIG. 2). Applicant has previously shown that strain RM118 grown under similar conditions expresses populations of LPS containing three to five glycose residues attached to a common inner-core element (Risberg et al., Eur. J. Biochem. 261:171-180, 1999). LPS from strains with mutations in lic1, lgtF, and lgtD showed similar complex banding patterns, while those from strains with mutations in lgtC, lic2A, lpsA, orfH, rfaF and opsX gave less complex patterns comprising bands having consecutively faster mobilities consistent with successive sugar deletions. Identification of the nature and location of sugar deletions in the LPS samples from mutant strains was achieved by comparative structural analysis. LPS was extracted from isogenic mutants of strain RM118 after growth in liquid culture. Structural fingerprinting was done using ESI-MS and 1D $^1H$-NMR analysis of O-deacylated LPS (LPS-OH) samples, obtained following treatment with anhydrous hydrazine. In addition, glycose and linkage analyses were carried out on intact LPS samples.

A comparison of the data obtained from mutant strains containing specifically inactivated putative glycosyltransferase genes with that from the structural model for the globotetraose containing RM118 LPS (Risberg et al., Eur. J. Biochem. 261:171-180, 1999) established the key structural features of the altered LPS glycoforms. ESI-MS provides a valuable tool for probing the structural composition of low molecular mass LPS (Gibson et al., J. Bacteriol. 175:2702-2712, 1993; Masoud et al., Biochem. 36:2091-2103, 1996; Risberg et al., Eur. J. Biochem. 261:171-180, 1999; Risberg et al., Eur. J. Biochem. 243:701-707. 1997; Phillips et al., Biochem. 35:5937-5947, 1996). The ESI-MS data obtained in the negative ion mode on the O-deacylated LPS samples is presented in Table 5. The LPS-OH samples from the mutant strains gave data consistent with the presence of oligosaccharides linked via Kdo-4-phosphate to a common O-deacylated lipid A moiety differing in the number of heptose, hexose and phosphate-containing substituents (Phillips et al., Biochem. 31:4515-4526, 1992; Masoud et al., Biochem. 36:2091-2103, 1996; Risberg et al., Eur. J. Biochem. 261:171-180, 1999; Schweda et al., Carbohydr. Res. 246:319-330, 1993; Schweda et al., Carbohydr. Res. 272:213-224, 1995; Risberg et al., Eur. J. Biochem. 243: 701-707, 1997; Phillips et al., Biochem. 35:5937-5947, 1996).

opsX mutant. Inactivation of opsX gave rise to deep-rough LPS, which was devoid of heptose or hexose residues, containing only a phosphorylated Kdo attached to the Lipid A moiety (Table 5). It has been previously shown that mutation in the opsX gene of *H. influenzae* type b strain RM153 results in truncation of the LPS between HepI and Kdo (Hood et al., Mol. Microbiol. 22:951-965, 1996). MS-MS analysis of that LPS-OH sample by low energy collisional activation of the doubly charged molecular ion (m/z 625) afforded a major fragment ion at m/z 951 (Lipid A-OH) arising from cleavage of the Kdo-β-D-glucosamine bond (data not shown). The mass of this fragment ion is consistent with that expected for *H. influenzae* Lipid A-OH (Helander et al., Eur. J. Biochem. 177:483-492, 1988). It is evident that RM118 and RM153 opsX mutants express LPS similar to that from the previously characterized. Rdisn (I69) mutant strain (Helander et al., Eur. J. Biochem. 177:483-492, 1988; Preston et al., J. Bacteriol. 178:396-402, 1996). The I69 LPS phenotype arises from a mutation in the heptose biosynthetic gene gmhA (Brook et al., J. Bacteriol. 178:3339-3341, 1996), rendering the mutant strain incapable of adding heptose to its LPS.

rfaF Mutant. $^1$H NMR analysis of LPS-OH from RM118rfaF showed, in addition to the expected $^1$H resonance from the α-linked glucosamine residue of lipid A, an anomeric proton-resonance (~5.19 ppm) in the low-field region from a single heptose unit. Sugar analysis confirmed the Hep residue to be L-glycero-D-manno heptose. Correspondingly, the ESI-MS spectrum was dominated by a single abundant doubly charged ion at m/z 721.6 consistent with the structure, Hep$_1$-Kdo-Lipid A-OH (Table 5).

orfH mutant. Organisms in which the orfH gene is inactivated gave a mixture of LPS glycoforms, each containing two Hep residues, as evidenced from the ESI-MS data (Table 5). In addition to the major population of glycoforms containing an additional Hep residue, ie, Hep$_2$.PEtn$_{0-2}$.Kdo-Lipid A-OH, compared to RM118rfaF LPS, were species containing a Hex-PCho unit. Sugar analysis indicated the presence of D-glucose and the PCho methyl protons gave an intense signal in the $^1$H NMR at 3.24 ppm. As expected, LPS from this strain reacted with TEPC-15, a PCho specific monoclonal antibody (Mab) (Weiser et al., Infect. Immun. 65:943-950, 1997), in immunoblot experiments. Linkage analysis revealed the presence of terminal Hep, 3-substituted Hep and 3,4-disubstituted Hep residues (Table 6). Based on the structure of the parent strain, this data is consistent with RM118orfH having the capacity to elaborate LPS expressing the two major glycoform structures 1 and 2 (PEtn shows partial substitution).

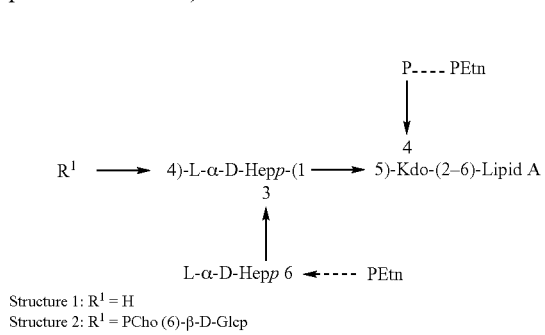

Structure 1: R$^1$ = H
Structure 2: R$^1$ = PCho (6)-β-D-Glcp

The occurrence of two bands for the LPS of RM118orfH when analysed by T-SDS-PAGE (FIG. 2) is consistent with this conclusion.

Figure 3:
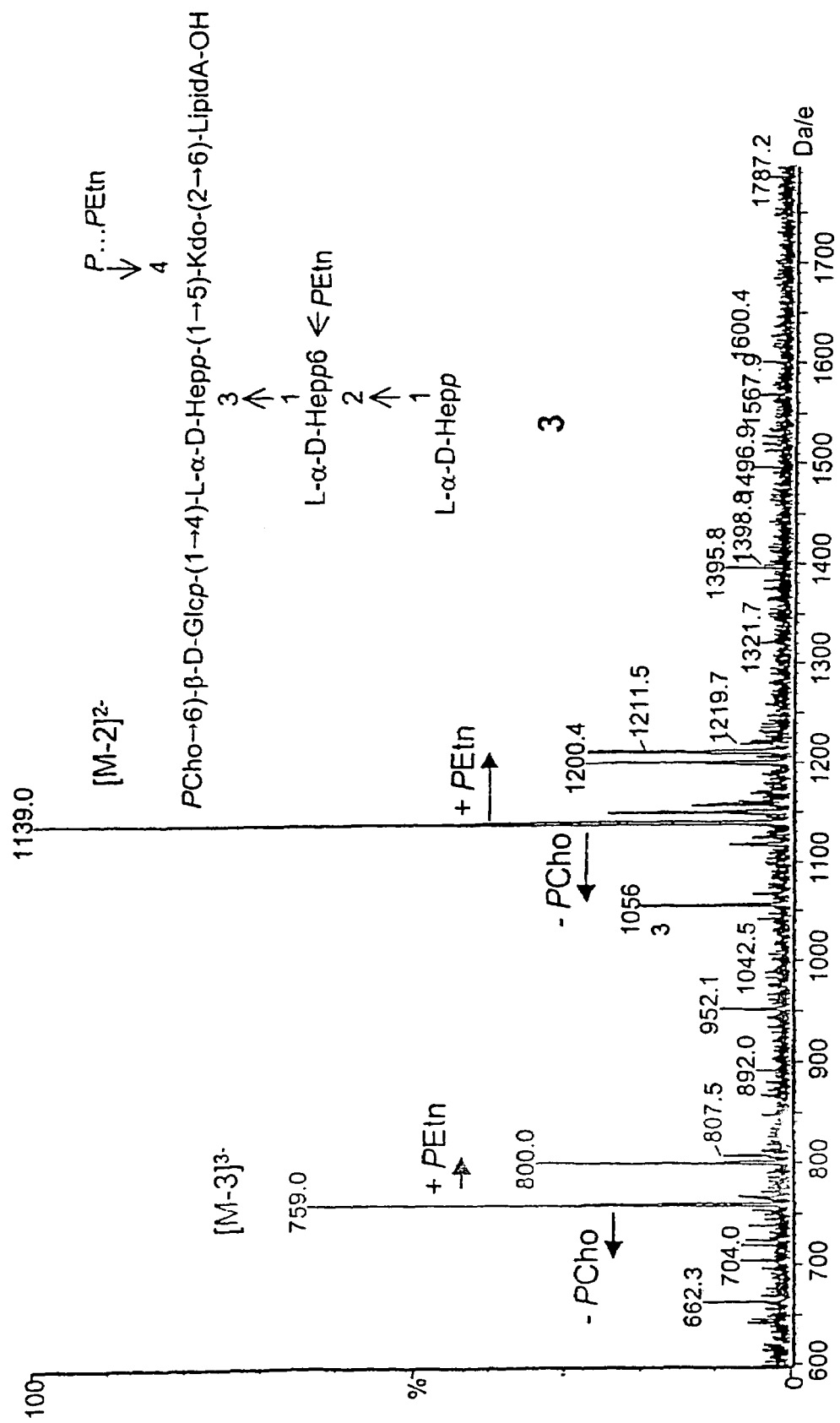
FIG. 3 is a negative ion ESI-MS of the O-deacylated LPS from the lpsA mutant of *H. influenzae* RM118 showing doubly and triply charged ions from the major Hex1 glycoform (Table 1, structure 3).
Figure 4:
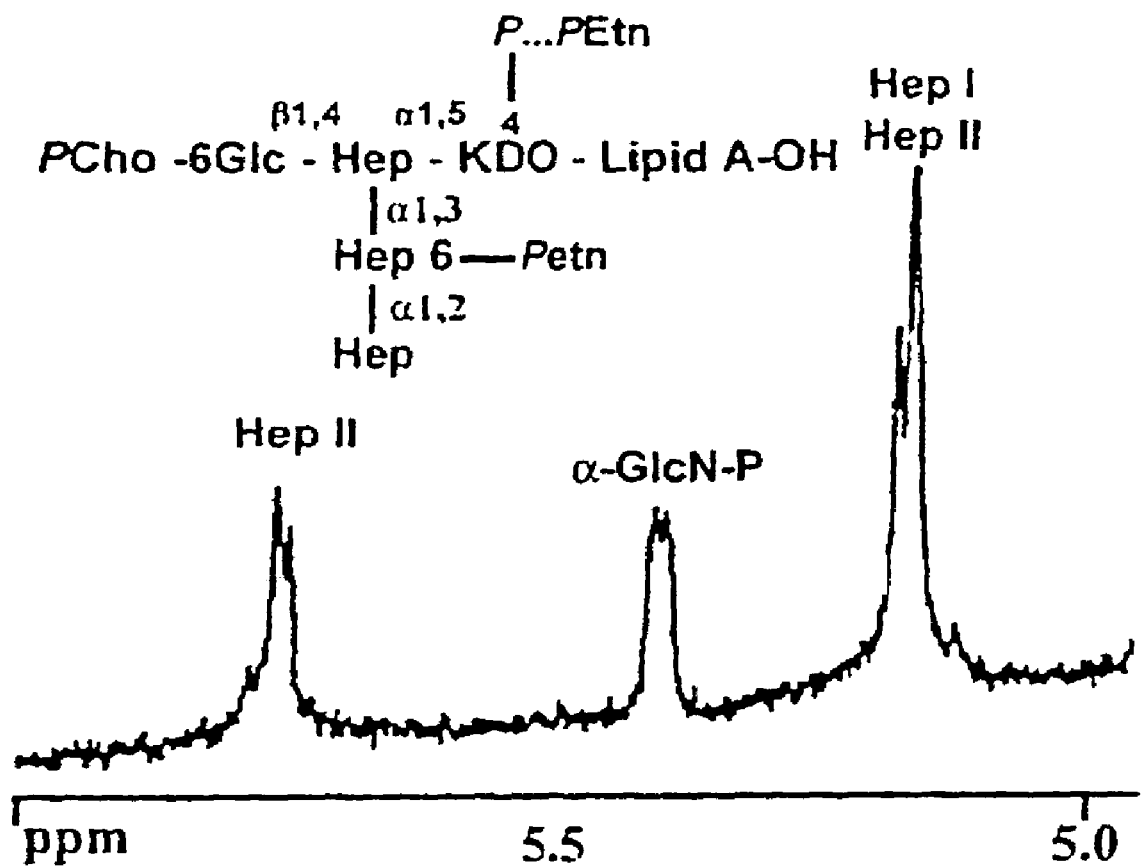
FIG. 4 is a $^1$H NMR spectrum of the O-deacylated LPS from the lpsA mutant of *H. influenzae* RM118 showing the α-anomeric proton region between 5.0 and 6.0 ppm, wherein. anomeric resonances corresponding to the 3,4-disubstituted Hep (HepI), 6-PEtn substituted Hep (HepII), terminal HEP (HEPIII) and phosphorylated α-GlcN in the Lipid A region are indicated.

1psA mutant. ESI-MS analysis of LPS-OH from RM118lpsA indicated it to contain glycoforms having an additional Hep residue when compared to RM118orfH (Table 5), the phosphocholine containing Hex1 glycoform being the major LPS species (FIG. 3). Linkage analysis was consistent with sequential addition of the heptose to the terminal Hep in structure 2 (Table 6). Correspondingly, the $^1$H NMR spectrum of this O-deacylated LPS sample showed the characteristic pattern in the low-field region (5.0-6.0 ppm) for the LPS tri-heptose inner-core element (HepII, 5.76 ppm; HepI/HepIII, 5.16/5.15 ppm) of *H. influenzae* (FIG. 4) (Risberg et al., Eur. J. Biochem. 261:171-180, 1999). This data is consistent with the RM118lpsA-derived LPS having the structure 3 (FIG. 3; Table 1).

1ic2A mutant. ESI-MS analysis of the O-deacylated LPS samples from strain RM118lic2A revealed the presence of Hex2 glycoforms as the major LPS species (Table 5). Compositional analysis of the RM118lic2A LPS indicated the presence of D-glucose as the only neutral hexose, linkage analysis indicating it to be a terminal residue (Table 6). A significant proportion of 2-linked heptose residues was also revealed by linkage analysis. It is noteworthy, that 2-substituted heptose residues were not detected in the LPS sample from the lpsA mutant due to substitution of that residue by PEtn groups (cf. Structure 3 in FIG. 3) which are not readily cleaved under the hydrolysis conditions employed in the linkage analysis procedure. In accord with these findings, it can be concluded that LPS from the lic2A mutant differs from. that of the lpsA mutant in that it carries a glucose residue at the 2-position of HepIII as shown in structure 4 (Table 1). The presence of an additional $^1$H NMR signal at 4.65 ppm indicated the terminal D-Glcp to have the β-configuration, the upfield shifted value of the resonance for HepII (5.58 ppm) compared to that of the unsubstituted analogue, (5.76 ppm) being indicative of the 1,2-linkage to HepIII (structure 4; Table 1) (Masoud et al., *Biochem.* 36:2091-2103, 1996, Schweda et al., Carbohydr. Res. 246: 319-330, 1993; Schweda et al, Carbohydr. Res. 272:213-224, 1995).

Figure 5:
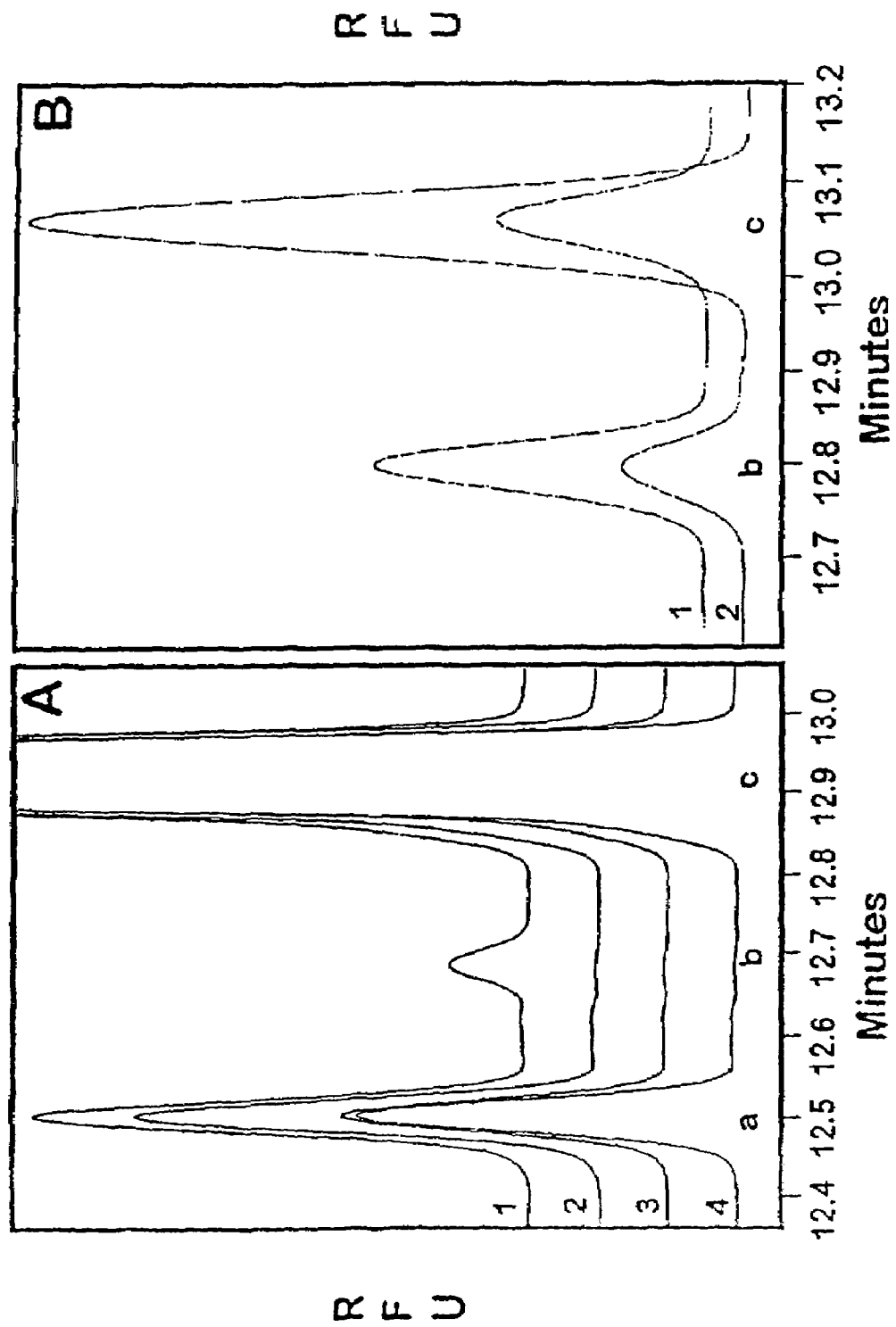
FIG. 5 is a capillary electrophoresis analysis of LgtD activity in *H. influenzae* strain RM118. Panel A, trace 1 is a complete reaction mixture using the 100,000×g pellet of a sonicate as enzyme source; trace 2 is similar to the reaction mixture in 1, except it is missing UDP-GalNAc; trace 3 is a complete reaction mixture from the mutant RM118:lgtD; trace 4 is similar to trace 3 except it is missing UDP-GalNAc. The peak A is an impurity in the FCHASE-$P^K$ preparation, peak b is FCHASE-Globotetraose, peak c is FCHASE-$P^K$. Panel B, trace 1 is the TLC purified product from a reaction as described for Panel A trace 1. Trace 2 is the same material as trace 1, but treated with β-hexosaminidase.

Lic 3A mutant. Similarly, a mutant was generated which permitted investigation of sialylated glycoforms. These studies confirmed the loss of sialic acid in the relevant lic3A mutant. The preparation of the mutant is described in Hood et al., Mol. Microbio. 39:341-350, 2001. The sialylated glycoform was found to be absent in strains containing a lic3A gene disruption. Lic3A has been demonstrated to have a sialyltransferase activity, which is modified by the action of another phase-variable glycosyltransferase, LgtC, which competes for the same lactosyl acceptor moiety.

lgtC mutant. In the RM118lgtC mutant, ESI-MS analysis of the O-deacylated LPS sample revealed the presence of Hex3 glycoforms. Sugar analysis indicated LPS from the lgtC mutant to contain D-galactose, which by linkage analysis was found to be present as a terminal residue (Table 6). Linkage analysis also revealed 4-linked D-Glcp residues consistent with the major Hex3 glycoform (Table 6) being substituted by a lactose moiety at HepIII (structure 5: Table 1). The $^1$H NMR spectrum of the LPS-OH is identical to that previously reported (Risberg et al., Eur. J. Biochem. 261: 171-180, 1999) for the lactose containing Hex3 LPS glycoform which is present in the parent strain. In $N.$ $meningitidis$, the lgtC gene has been shown to encode a 1,4-α-galactosyltransferase (Wakarchuk et al., Protein Eng. 11:295-302, 1998). A similar function was demonstrated for lgtC from RM118 by examination of the transferase activity of the recombinant enzyme and by analysis of the LPS from the RM118lgtC mutant.

lgtD mutant. A mixture of Hex3 and Hex4 LPS glycoforms were elaborated by $H.$ $influenzae$ RM118 in which the lgtD gene is inactivated (Table 5). In accord, two bands were observed upon T-SDS-PAGE analysis of the LPS, one corresponding in electrophoretic mobility to that from the lgtC mutant and a slower migrating band (FIG. 2). LPS from this mutant strain contained terminal and 4-linked D-Galp residues (Table 6). A comparison of the 1D $^1$H NMR spectra with those of the parent strain and its lgtC mutant, pointed to the presence of an α-D-Galp-(1→4)-β-D-Galp unit in the Hex4 glycoform, a signal at 5.01 ppm being indicative of the terminal α-D-Galp residue (structure 6; Table 1). The lgtd gene product was investigated for glycosyltransferase activity with the synthetic acceptor, FCHASE-P$^K$. A comparison of the parent RM118 and the lgtD mutant strains in the CE assay showed loss of β-GalpNAc transferase activity in the mutant (FIG. 5).

lgtF mutant. Mutation of the lgtF gene in $H.$ $influenzae$ gave a strain from which the LPS neither reacted with MAb TEPC-15 (data not shown) nor showed the characteristic PCho methyl proton signal (3.24 ppm) in their $^1$H NMR spectrum. Linkage analysis indicated that the LPS lacked the terminal β-D-Glcp residue, containing only mono-3-substituted HepI residues (Table 6). A similar distribution of glycoforms, as found in the parent strain LPS, differing in the length of the oligosaccharide chain from HepIII was observed for LPS-OH from the lgtF mutant in its ESI-MS (Table 5). It is noteworthy that full extension of the globotetraose unit from HepIII can occur in the absence or the presence of the β-D-Glcp residue at HepI (FIG. 6). Applicant has shown that the parent strain can elaborate mixed populations of LPS glycoforms in which the galabiose unit is elongated by the addition of a terminal β-D-GalpNAc residue giving the globotraose units β-D-GalpNAc-(1→3)-α-D-Galp-(1→4)-β-D-Galp-(1→4)-β-D-Glcp (Risberg et al., Eur. J. Biochem. 261:171-180, 1999).

lic1 mutant. ESI-MS analysis of O-deacylated LPS from the lic1 mutant gave a similar heterogenous mixture of glycoforms (Table 5) as that observed in the parent strain (Risberg et al., Eur. J. Biochem. 261:171-180, 1999), but lacking the presence of PCho substituents. The lic1 locus has been shown to contain genes responsible for expression of PCho substituents at the 6-position of the β-D-Glcp attached to the 3,4-disubstituted heptose (HepI) in RM118 (Risberg et al., Eur. J. Biochem. 261:171-180, 1999; Weiser et al., Infect. Immun. 65:943-950, 1997). Examination of the $^1$H-NMR spectrum of RM118lic1 O-deacylated LPS revealed the absence of the characteristic PCho methyl proton signal at 3.24 ppm. Additionally the LPS from this lic1 mutant, as expected (Weiser et al., Infect. Immun. 65:943-950, 1997), did not react with Mab TEPC-15 (data not shown).

Example 2

Substitutions and Modifications of Inner Core Moiety

In NTHi strain 2019, HepI is substituted by lactose ($R_1$=β-D-Galp-(1→4)-β-D-Glcp; $R_2/R_3$=H) (Phillips et al., Biochemistry 31:4515-4526, 1992). In NTHi strain 375, HepIII is substituted by sialylated lactose in a minor glycoform population ($R_1$=β-D-Glcp, $R_2$=H, $R_3$=Neu5Ac-β-D-Galp-(1→4)-β-D-Glcp-(1→2)) (Hood et al., Mol. Micro. 33:679-692, 1999). This example summarizes the results of structural investigations of LPS from 4 NTHi strains by using methylation analysis, electrospray ionization mass spectrometry (ESI-MS) and NMR.

$H.$ $influenzae$ non-typeable strains 486, 176, 285 and 1159 were obtained from the strain collection of Prof. Eskola (Hood et al., Mol. Microb. 1999) as part of a Finnish otitis media cohort study and are isolates obtained from the inner ear. Bacteria were grown in brain heart infusion (BHI) broth (Difco™ (3.7%, w/v) containing nicotinamide adenine dinucleotide (NAD) (2 μg/mL), hemin (10 μg/mL) and neuraminic acid (NeuAc; 50 μg/mL) at 37° C. LPS was obtained from lyophilized bacteria by using the phenol-chloroform-petroleum ether method, followed by ultracentrifugation (Risberg et al., Eur. J. Biochem. 261:171-180, 1999). Detailed structural studies were made through the use of MS-based methods and high-field NMR techniques on oligosaccharide samples obtained from LPS samples either by O-deacylation with anhydrous hydrazine (37° C., 1 h) or cleavage of the Kdo ketosidic linkage with dilute aqueous acetic acid (100° C., 2 h).

Compositional sugar analyses of LPS from NTHi strains 486, 176, 285 and 1158 all indicated D-glucose (Glc), 2-amino-2-deoxy-D-glucose (GlcN) and L-glycero-D-manno-heptose (Hep) as major components identified by GLC-MS of their corresponding alditol acetate-and 2-butyl glycoside derivatives. In addition, D-galactose (Gal) was identified in strains 486, 176 and 1158. Furthermore, D-glycero-D-manno-heptose was found to be a major component in strain 1158. This sugar was recently identified for the first time as a component in $H.$ $influenzae$ LPS in NTHi strain 9274 (Rahman et al., Glycobiology 9:1371-1380, 1999). Treatment of O-deacylated LPS (LPS-OH) with neuraminidase followed by high-performance anion-exchange chromatography and ESI-MS indicated sialic acid (NeuAc) to be a major component in NTHi strain 486. Minor amounts were detected in NTHi strains 176, 285 and 1158.

Figure 10:
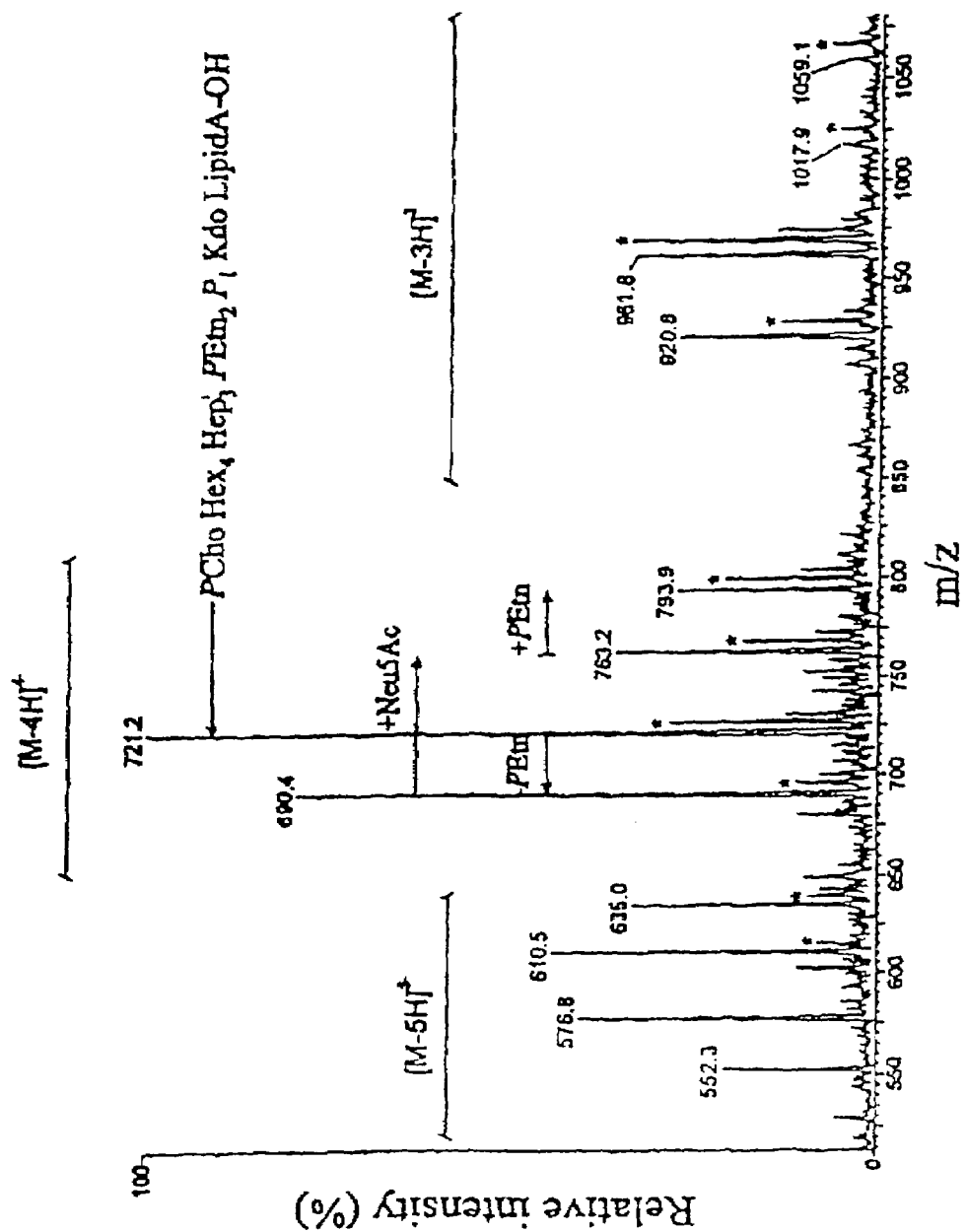
FIG. 10 is a representation of part of the negative-ion ESI-MS spectrum of O-deacylated LPS from NTHi strain 486. The proposed compositions of the major glycoforms are indicated. Sodiated adducts are indicated by an asterisk (*).

ESI-MS of LPS-OH samples indicated heterogeneous mixtures of glycoforms in all strains. Part of the ESI-MS spectrum of LPS-OH from NTHi 486 is shown in FIG. 10.

Proposed compositions for the major LPS glycoforms of the NTHi strains are shown in Table 7. All glycoforms contain the conserved PEtn-substituted triheptosyl inner-core moiety attached via a phosphorylated Kdo linker to the putative O-deacylated lipid A (Lipid A-OH).

PCho is present in all strains as a major component. The presence of two PCho in a Hex2-glycoform is indicated for strain 1158. The shortest glycoform (Hex1) is observed for strain 285.

Figure 11:
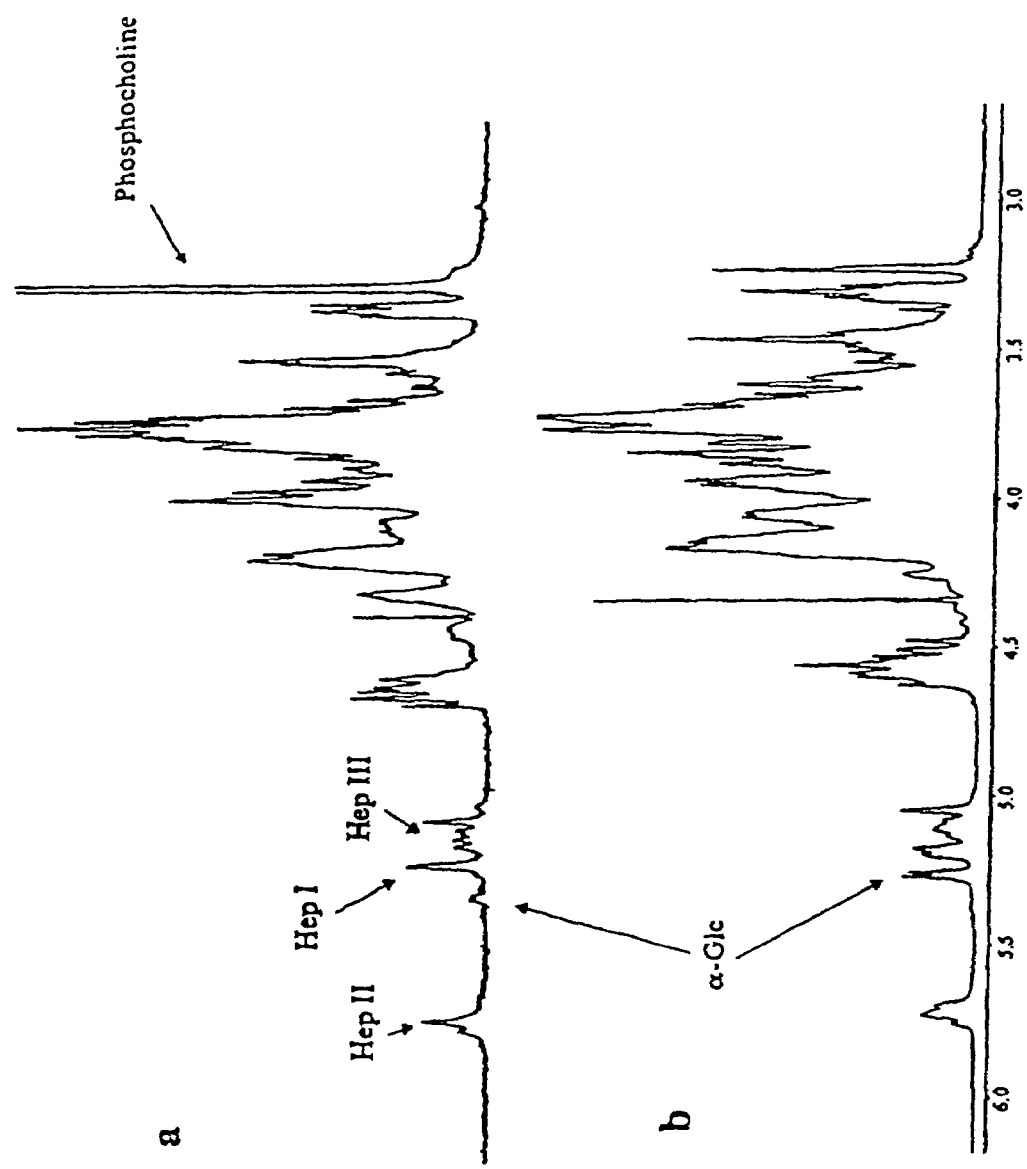
FIG. 11 is a representation of a 270 MHz $^1$H NMR spectra of Fr.2 dervived from NTHi 176 (a) and Fr. 3 (b).
Figure 12:
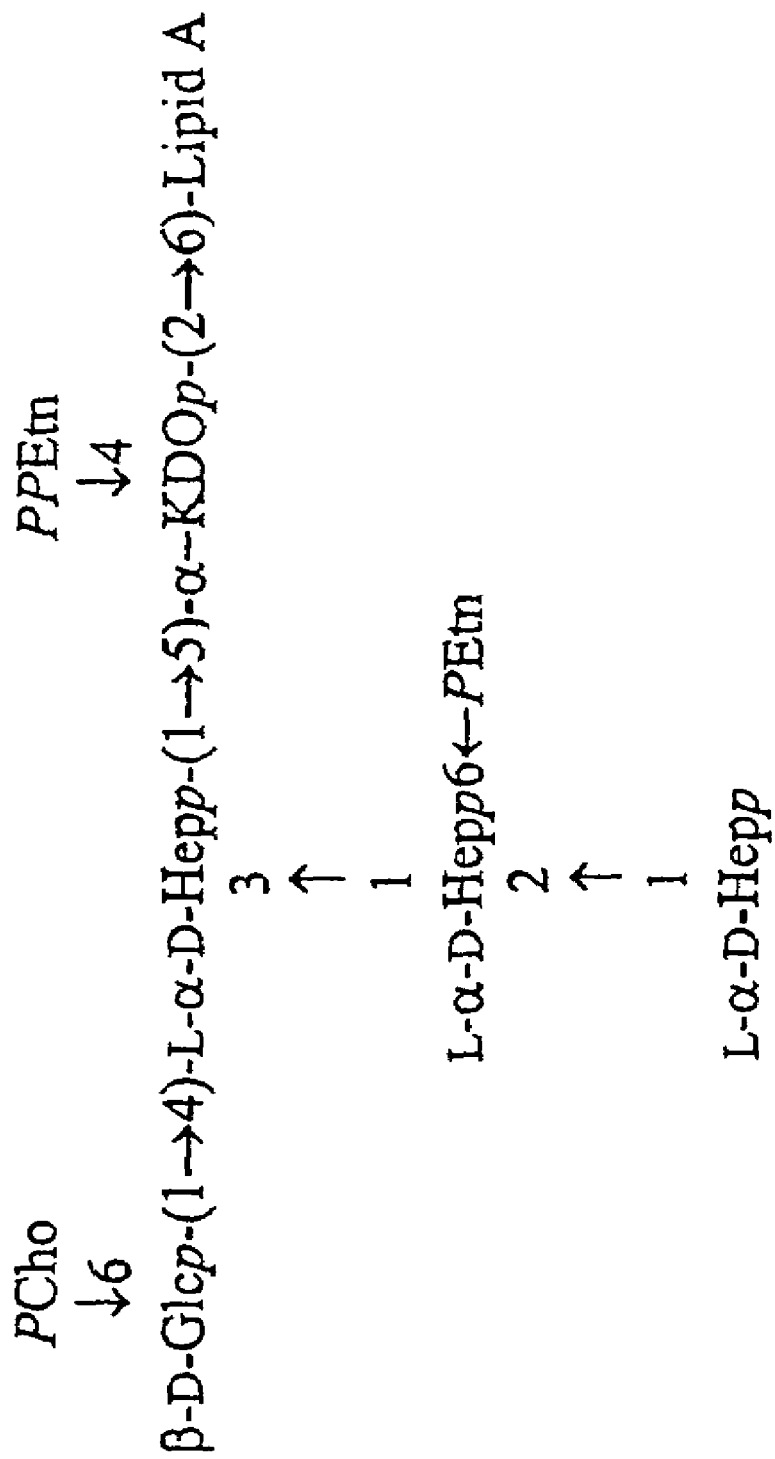
FIG. 12 illustrates the structure of the major Hex1 LPS glycoform observed in NTHi 285.
Figure 13:
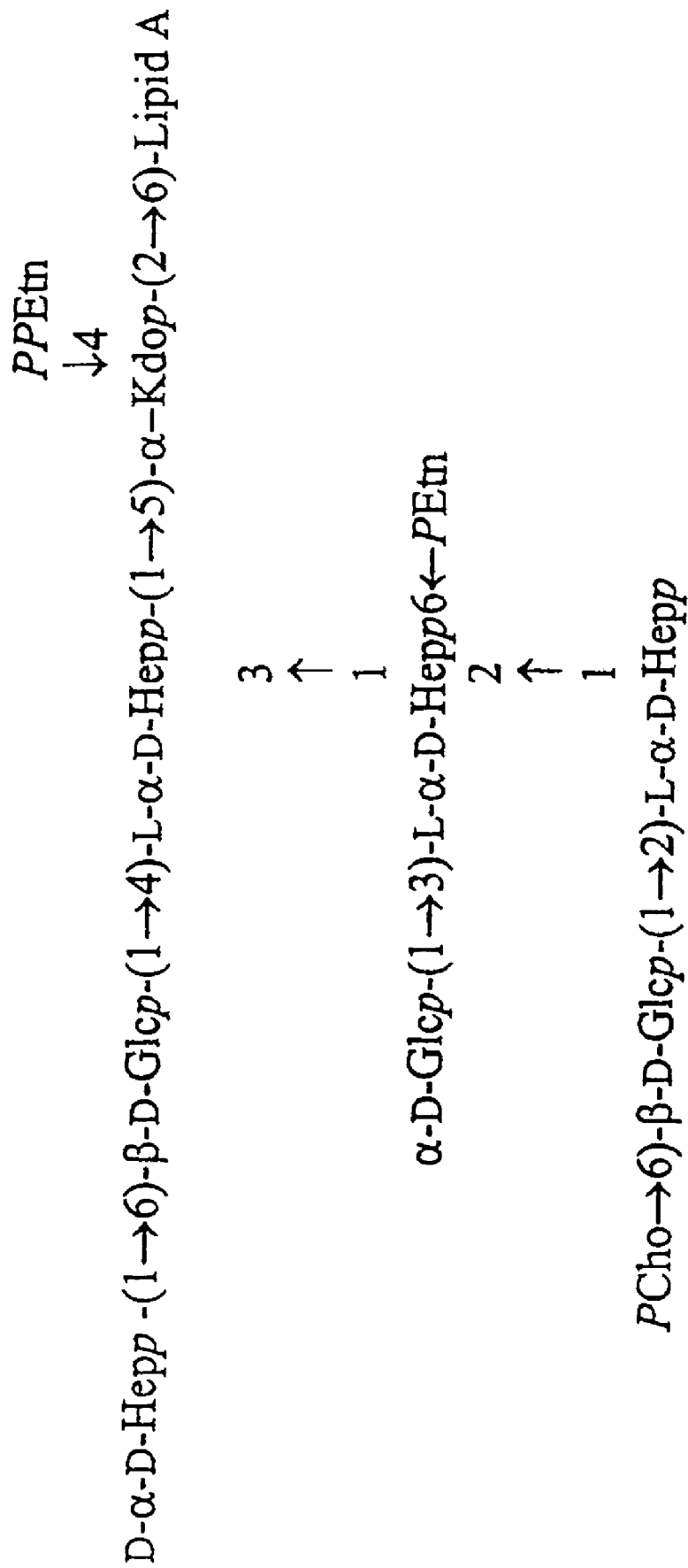
FIG. 13 illustrates the postulated structure of the major LPS glycoform in NTHi 1158.

Methylation analyses data of the LPS samples is given in Table 8. It is noteworthy that only traces of 2-substituted Hep, an integral component of previously published *H. influenzae* structures, was detectable in strains 176 and 486. Instead, significant amounts of 3-substituted Hep were detected pointing to a new substitution pattern in the common L-α-D-Hepp-(1→2)-L-αD-Hepp-(1→3)-[β-D-Glcp-(1→4)-]-L-α-D-Hepp-(1→5)-α-Kdop inner-core element of *H. influenzae* LPS. The complete structures for the major glycoforms in strains 176 and 486 were determined by NMR and the results are summarized in FIG. 11. Methylation analysis of strain 285 revealed, inter alia, high amounts of terminal L,D-Hep in addition to 3,4-disubstituted Hep which indicated an absence of substitution at HepII and HepIII of the triheptosyl inner-core moiety. The complete structure of the Hex1 glycoform in this strain (FIG. 12) was determined by NMR on LPS-OH (data not shown). Methylation analysis of strain 1158 showed, inter alia, 6-substituted D-Glc and terminal D,D-Hep which could be attributed to the structural element, D-α-D-Hepp-(1→6)-β-D-Glcp-(1→4)-L-α-D-Hepp which is evidenced by NMR (data not shown). The major LPS glycoform was found to be substituted at HepII (α-D-Glcp) and HepIII (PCho→6)-β-D-Glcp). A tentative structure of the major glycoform in NTHi 1158 is given in FIG. 13.

Figure 14:
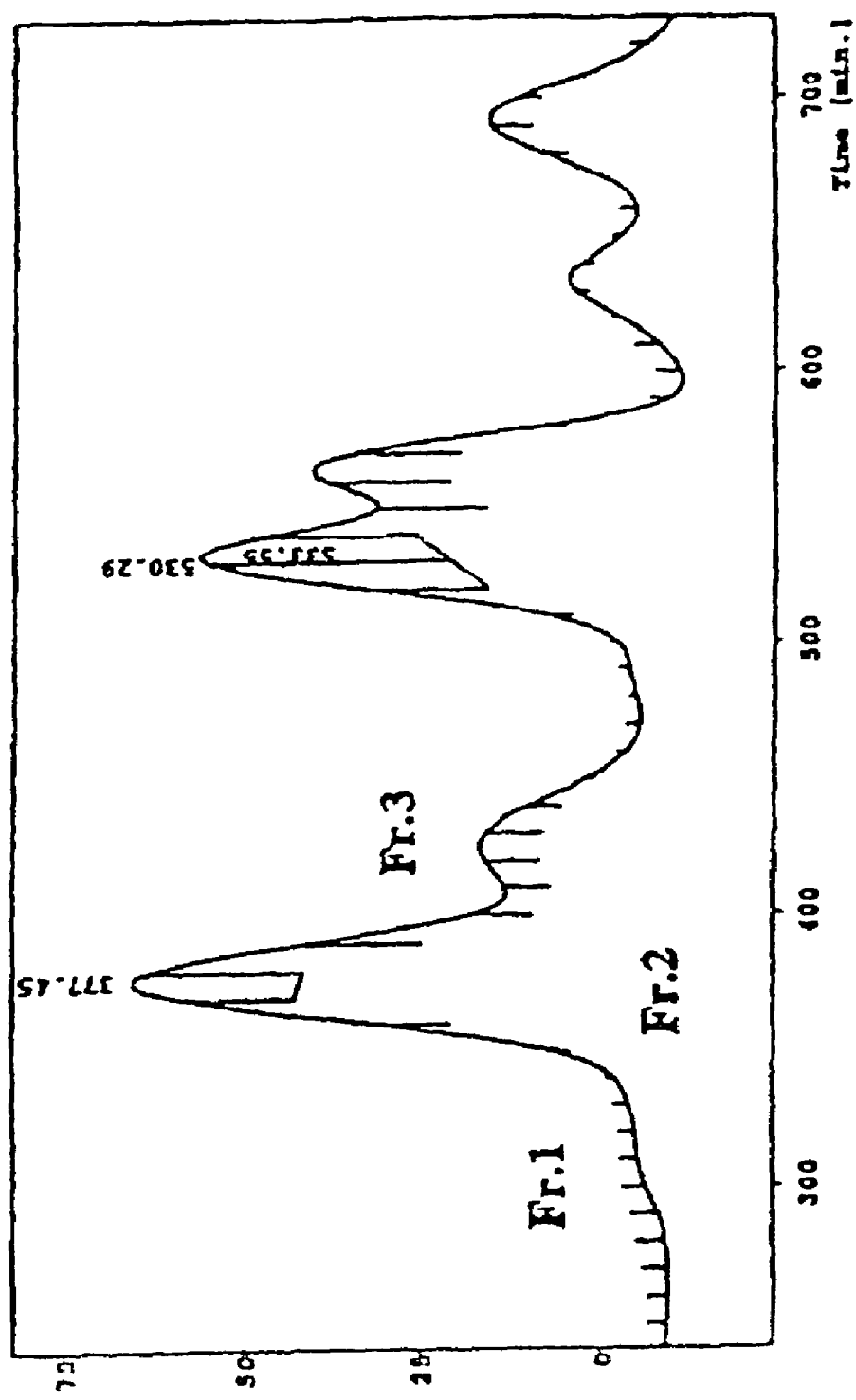
FIG. 14 is a representation of a Biogel P-4 chromatogram of LPS (100 mg) of NTHi 176 after mild acid hydrolysis. Indicated are Fr.1 (1 mg), Fr.2 (10 mg) and Fr.3 (6.4 mg).

Structural Details of NTHi 176. Partial acid hydrolysis of LPS with dilute acetic acid afforded an insoluble lipid A and core oligosaccharide fractions which were separated by GPC (FIG. 14) giving Fr.1, Fr.2 and Fr.3. The methylation analysis data for these fractions are presented in Table 8. The presence of 3- and 6-substituted Gal and 4-substituted GlcN in Fr.1 indicated the presence of novel structural features for his oligosaccharide. CE-ESI-MS on Fr.1 revealed, inter alia, major doubly charged ion at m/z 1214.0 indicating a considerably higher molecular weight glycoform (HMG) in this fraction than observed in Fr.2 and Fr.3. A similar observation was made for NTHi 285 (see below). The ESI-MS spectrum of Fr.2 (data not shown) indicated the major glycoforms to have the composition PCho$_1$.Hex$_2$.Hep$_3$.PEtn.AnKdo-ol and PCho$_1$.Hex$_3$.Hep$_3$.PEtn.AnKdo-ol The ESI-MS for Fr.3 (data not shown) indicated major glycoforms with the respective compositions Hex$_3$.Hep$_3$.PEtn.AnKdo-ol and Hex$_4$.Hep$_3$.PEtn.AnKdo-l.

Figure 15:
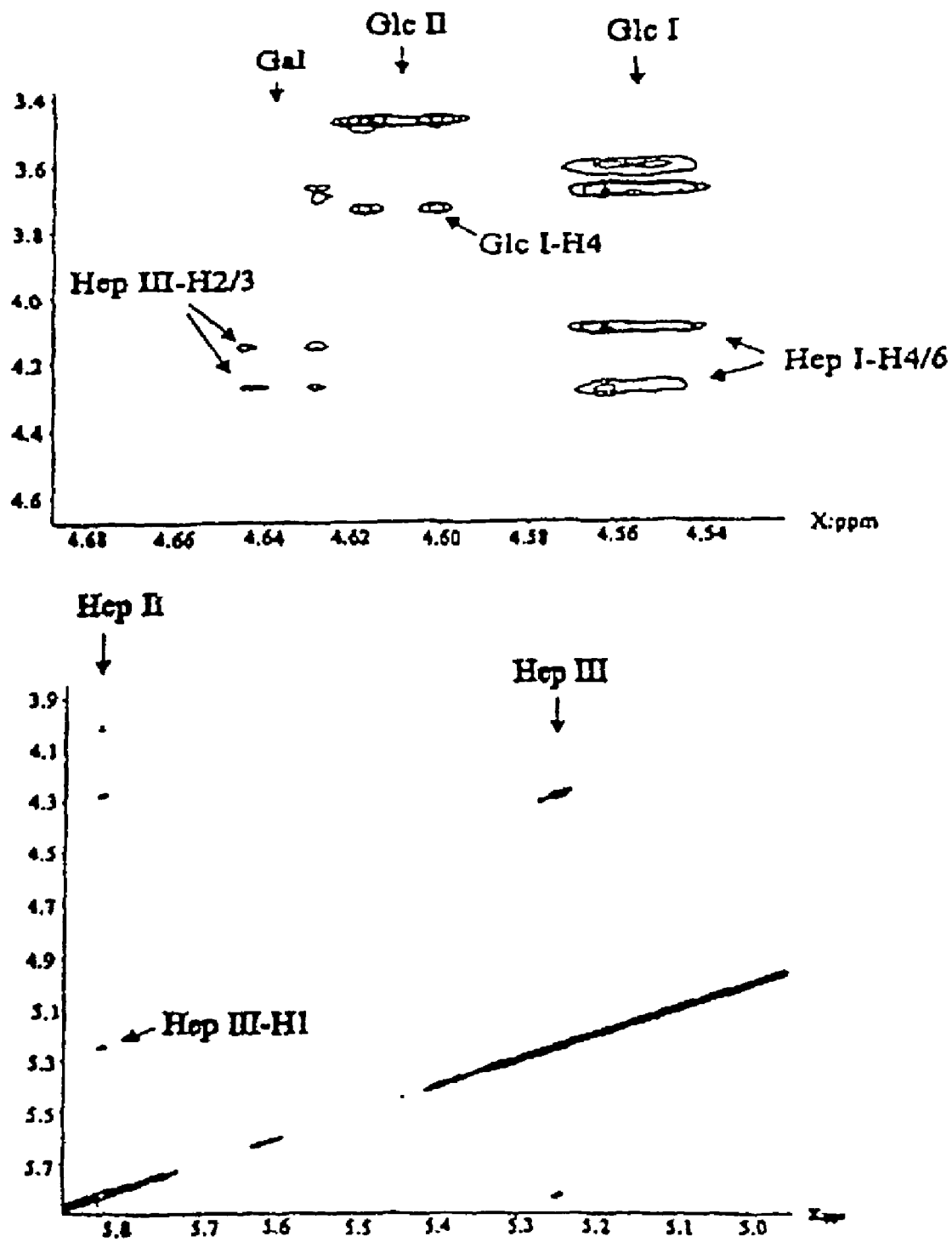
FIG. 15 is a representation of parts of the 500 MHz 2D NOESY spectrum of Fr.2 of NTHi 176.
Figure 16:
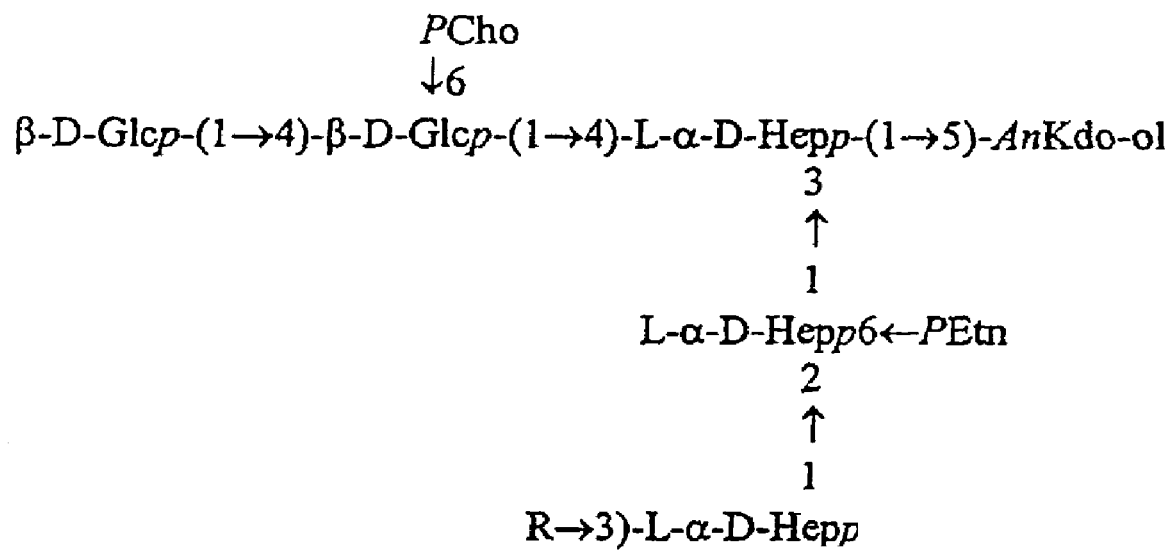
FIG. 16 illustrates various structures of oligosaccharides derived from NTHi 176 LPS.

The structure of the Hex3 glycoform in Fr.2 could be determined by detailed $^1$H-NMR analysis. The $^1$H-NMR spectrum of Fr.2 is shown in FIG. 11a. The characteristic signal for the methyl groups of PCho was observed at δ 3.24. Anomeric resonances of HepI-HepIII were identified at 5.03-5.13, 5.83 and 5.26, respectively. Subspectra corresponding to Glc I, Glc II and Gal were identified in the 2D COSY and TOCSY spectra at δ 4.56, 4.62 and 4.64, respectively. Chemical shift data point to Glc II and Gal being terminal residues in agreement with methylation analyses. The down field shifted value for H-6,6' of Glc I at δ 4.3 indicated this residue to be substituted with PCho at this position. Interresidue NOE connectivities between proton pairs Glc II H-1/Glc I H-4, Glc I H-1/Hep I H-4,6 (FIG. 15) established the sequence of a disaccharide unit and its attachment point to HepI as β-D-Glcp-(1→4)-[PCho→]-β-D-Glcp-(1→4)-L-α-D-Hepp-(1→. Interresidue NOE between H-1 of Gal and H-3/H-2 of HepIII gave evidence for the β-D-Galp-(1→3)-L-α-D-Hepp-(1→unit. From the combined data it could thus be concluded that the PCho substituted Hex3 glycoform has structure 2. Methylation analysis of Fr.2 showed a considerable amount of terminal Hep and it could be concluded that the PCho substituted Hex2 glycoform observed in ESI-MS spectra has structure 3.

The $^1$H-NMR spectrum of Fr.3 is shown in FIG. 11b. In agreement with ESI-MS data it is evident that PCho is not expressed to the high degree as in Fr.2 since the signal for methyl protons of PCho is of low intensity. Signals for anomeric protons of HepI-III resonate at approximately identical chemical shifts as the corresponding ones in Fr.2. At δ 5.26 the anomeric resonance of an α-linked terminal Glc residue (Glc-III) is observed. The anomeric region for β-linked hexoses was more heterogeneous than in Fr.2. In 2D spectra spin systems for terminal Glc residues were observed at δ 4.50 and 4.45. A 4-substituted Glc and two terminal Gal residues were identified at δ 4.56, 4.61 and 4.54. NOE data confirmed the presence of the structural element Glcp-(1→4)-β-D-Glcp-(1→4)-L-α-D-Hepp-(1→ . . . as well as Gal linked to HepIII. In addition, NOE connectivities confirmed the α-linked Glc to be attached to the 3-position of HepII. The combined evidence leads to the structure of the Hex4 glycoform as shown in the structure numbered 4. In agreement with methylation analysis showing 2-substituted Hep and terminal Hep, the Hex3 glycoforms are concluded to have structures 5 and 6.

Figure 17:
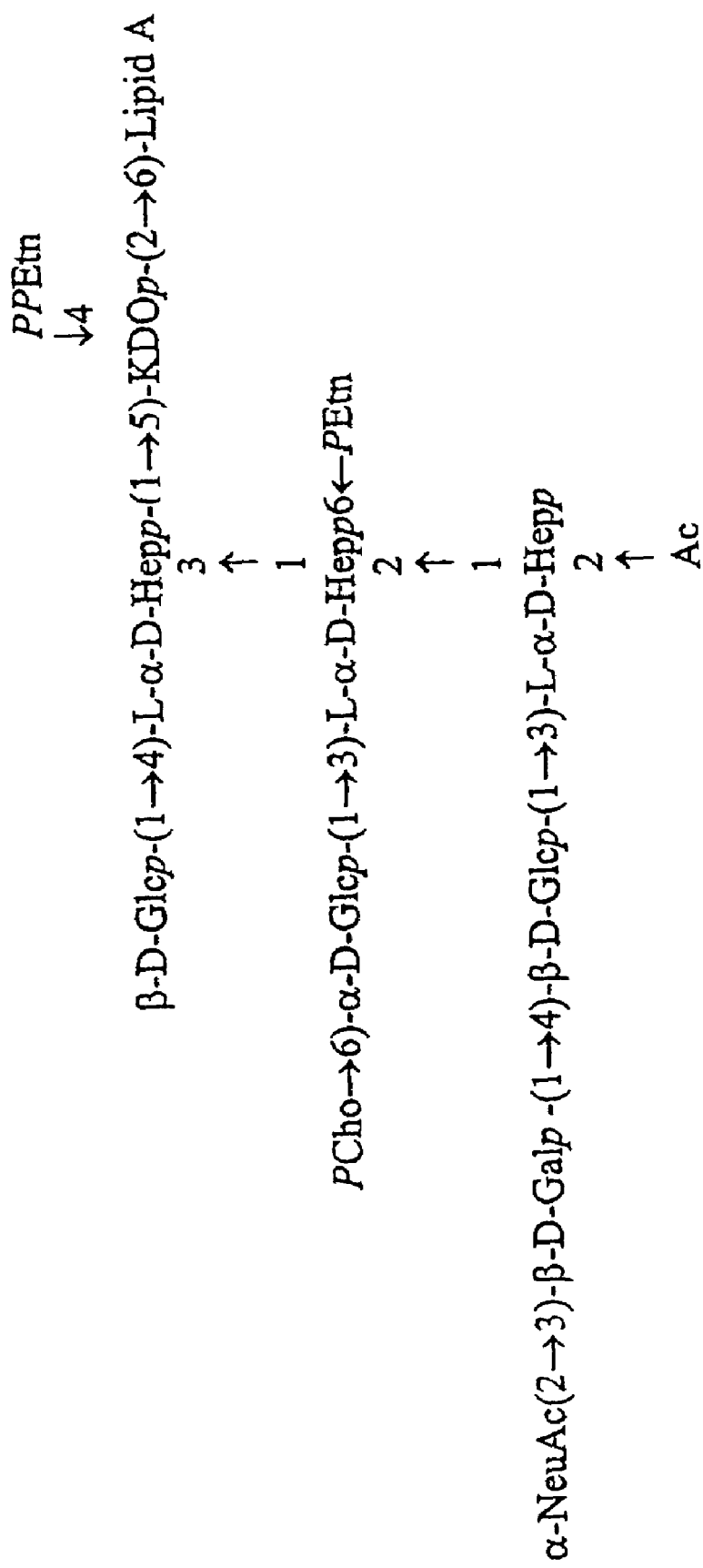
FIG. 17 illustrates the structure of the major NeuAc containing LPS glycoform of NTHi 486.

Structural Details of NTHi 486. The structure of the major LPS of glycoform NTHi 486 was established following extensive use of ESI-MS, NMR and methylation analysis on LPS-OH and oligosaccharide material (OS-1) obtained after mild acid hydrolysis (FIG. 17). As for strain 176, HepIII is substituted at the O-3 position, However in this case, by a glucose residue. NTHi 486 LPS is highly sialylated with Neu5Ac linked to the terminal β-galactose of a lactose moiety.

In the $^1$H NMR spectrum of LPS-OH, five discrete signals of approximately equal area were observed between δ 5.8 and 5.0. Three of these signals corresponded to the H-1 signals of the three heptose residues (HepI-HepIII) in the inner-core region. The anomeric signal of an α-linked glucose residue (Glc I) was identified at δ 5.28 (L 3.8 Hz), anomeric signals corresponding to β-linked hexoses were identified between δ 4.52 and 4.42. In the $^1$H NMR spectrum of OS-1, anomeric resonances of the heptoses as well as one acetylation site were observed at δ 5.83-5.75 (1H, not resolved) and δ 5.14-5.04 (3H, not resolved). An intense signal corresponding to the methyl protons of one O-acetyl group was observed at δ 2.17, which correlated to a $^{13}$C signal at δ 21.0 in the HSQC-spectrum. The sequence of the glycoses within the inner-core region was established from transglycosidic NOE connectivities relating anomeric and aglyconic protons on adjacent residues. Signals for the methyl protons of PCho were observed at δ 3.21 (LPS-OH) and δ 3.23 (OS-1) and spin-systems for ethylene protons from this residue and from PEtn were similar to those observed earlier (Risberg et al., Eur. J. Biochem. 261:171-180, 1999). $^1$H-$^{31}$P NMR correlation studies of LPS-OH and OS-1 demonstrated PCho and PEtn to be linked to Glc I and HepII residues, respectively. Characteristic signals from the H-3 methylene protons of sialic acid were observed at δ 1.79 (H-$3_{ax}$, $J_{3ax,3eq}$=12.3 Hz) and (δ 2.73 (H-$3_{eq}$, $J_{3eq,4}$=4.3 Hz) in the $^1$H NMR spectrum of LPS-OH. Interresidue NOE between H-$3_{ax}$ of Neu5Ac and H-3 of a Gal residue confirmed the sialic acid to be 2,3-linked to galactose as indicated by the methylation analyses, α-D-Neu5Ac-(2→3)-β-D-Galp-(1→. Several chemical shift values for a number of nuclei in HepIII of OS-1 differed considerably from the corresponding chemical shifts in LPS-OH. Downfield shifts were obtained for H-2 (+0.99 ppm), H-1 (+0.03 ppm), H-3 (+0.22 ppm) and C-2 (+1.2 ppm) of HepIII in OS-1, while C-1 (−3.3 ppm) and C-3 (−2.5 ppm) were shifted upfield. Thus, it was indicated that HepIII was acetylated at the O-2-position. The acetylation site was further supported by the HMBC experiment, where a correlation was seen between the carbonyl carbon(δ 174.0) and H-2 of HepIII. In addition, a crosspeak was observed between the carbonyl carbon and the methyl protons of the O-acetyl group, thereby establishing the identity of the substituent.

ESI-MS and methylation analysis of LPS from the lpsA mutant of NTHi 486 indicated an absence of chain extension from HepIII. Methylation analysis of O-deacylated material showed terminal Glc, terminal Hep, 3,4-disubstituted Hep, 2,3-disubstituted Hep and 6-substituted GlcN in the relative proportions 34:39:20:3:4. In the ESI-MS spectrum of LPS-OH, two major triply charged ions at m/z 812.9/853.9 could be seen, corresponding to PCho.Hex$_2$.Hep$_3$.PEtn$_{1-2}$.P$_1$.Kdo$_1$.Lipid A-OH.

High Molecular Weight Glycoforms in NTHi 176 and 285. After mild acid hydrolysis on LPS from NTHi 285, gel filtration showed a minor fraction containing a higher molecular weight glycoform together with a main fraction which contained the glycoform shown in FIG. 12. Sugar analysis of this high molecular (HMW) fraction indicated D-Glc, D-Gal, D-GlcNAc and L,D-Hep and methylation analysis gave terminal Gal, 3-substituted Gal, 6-substituted Gal, 4-substituted GlcNAc, terminal Hep and 3,4-disubstituted Hep. CE-ESI-MS showed, inter alia, a major doubly charged ion at m/z 1052. MS/MS on this ion gave a similar fragmentation pattern as m/z 1214 observed for HMW of NTHi 176 (see above). In particular a daughter ion was observed at m/z 692 corresponding to a composition PchoHex-Hex-HexNAc.

Example 3

Preparation of Monoclonal Antibodies (MAb) to *Heamophilus influenzae* Rd Lic1lpsA Double Mutant Female BALB/c mice, 6-8 weeks of age, were immunised intraperitoneally with formalin-killed Rd lic1lpsA whole cells. Each mouse received $10^8$ cells in 0.5 ml PBS per injection. The mice were boosted on day 14, 35 and trial bled on day 45. The two mice showing the highest antibody titre to the homologous LPS were given two final injections on day 56, an ip injection as given previously and an intravenous injection in 0.1 ml PBS. The fusion was performed three days following the last injection. Stimulated spleen cells from the two immunised mice were fused with SP2/O-Ag14 myeloma cells in a ratio of 10:1 in 33% PEG1450. Putative hybrids surviving the hypoxanthine/aminopterin/thymidine (HAT) selection, were screened by ELISA against homologous Rd lic1lpsA LPS and heterologous Rd LPS. Hybridomas producing antibody of interest were cloned twice using limiting dilution to ensure stability and clonality. Ig subclass was determined on spent supernatant using an EIA mouse MAb isotyping kit (Amersham Canada, Oakville, ON). Clones were expanded as ascitic fluid by intraperitoneal injection of $10^6$ hybridoma cells in BALB/c mice 10-14 days following ip treatment with 0.5 ml 2,6,10,14-tetramethyl-pentadecane (pristane). Ascitic fluid was tapped 7-14 days post-injection.

Indirect ELISA. Culture supernatant and ascitic fluid were assayed against purified LPS in 96-well Nunc Maxisorp EIA plates. Wells were coated at 37° C. for 3 h with 1.0 µg LPS in 100 µl 0.05M carbonate buffer (pH 9.8) containing 0.02 M MgCl$_2$ and then blocked with 200 µl % BSA-PBS for 1 h at room temperature. Following washing with PBS-T (0.05% Tween 20), samples of culture supernatant or ascites, serially diluted in 1% BSA-PBS, were added and incubated 1-3 h at room temperature. The plates were then washed and alkaline phosphatase-labelled goat anti-mouse IgG (Cedarlane Laboratories, Hornby, ON), diluted 1:3000 in 1% BSA-PBS, was added for 1 h at room temperature. The plates were developed with p-NPP Phosphate Substrate System (Kirkegaard & Perry Laboratories, Gaithersberg, Md.). After 30-60 minutes, the plates were scanned at 410 nm in a Dynatech EIA plate reader.

Results. Immunisation of BALB/c mice with formalin-killed whole cells of Rd lic1lpsA, fusion, and initial ELISA screening against the homologous LPS and heterologous Rd LPS resulted in the establishment of 12 hybridomas. Following testing of the 12 MAbs against a panel of Rd mutant LPS, two MAbs, LLA5, IgG$_{2a}$ and LLA4, IgG$_{2b}$, were chosen for further testing. LLA5 was found to cross react with 14 out of 25 non-typable strain LPS whereas LLA4 recognised the homologous LPS. Structural analysis revealed that LLA5 was detecting high molecular weight glycoforms while LLA4 bound to an inner core epitope present in the homologous strain.

Example 4

Preparation of the Hi Rdlic1lpsA LPS-OH-BSA Conjugate

LPS from *H. influenzae* double mutant strain Rdlic1lpsA was isolated and purified by the phenol water extraction protocol and O-deacylated by treatment with anhydrous hydrazine according to the procedures described earlier. Sugar analysis indicated the oligosaccharide portion of the LPS-OH to contain L-glycero-D-manno-heptose and glucose as the only detectable aldoses. ESI-MS of the LPS-OH revealed a doubly charged ion at m/z 1056.5 corresponding to a molecular mass of 2114.9 Da which is consistent with the expected composition of Glc(HepIII.PEtn.Kdo.P-Lipid A-OH(1). $^1$H NMR clearly showed well defined anomeric signals from the heptose residues at 5.16 (HepI), 5.15 (HepIII) and 5.76 ppm (HepII) for the conserved triheptosyl moiety similar to that of LPS-OH observed for the RdlpsA single mutant. No signal due to Pcho methyl resonances (Risberg et al., Eur. J. Biochem. 261:171-180, 1999) was detectable in the $^1$H NMR.

Example 5

Figure 8:
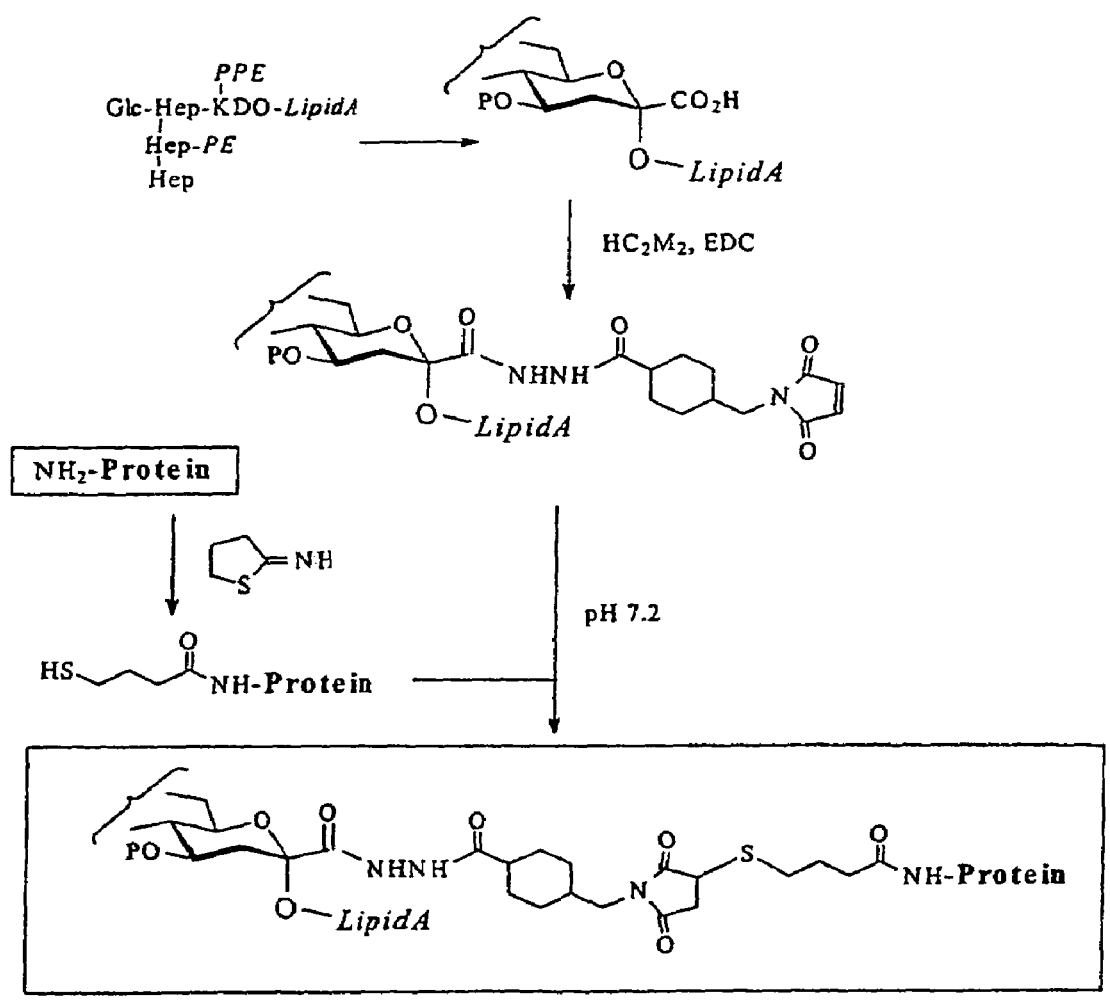
FIG. 8 is a scheme for conjugation of a *H. influenzae* strain Rdlic1lpsA LPS-OH to a carrier protein (BSA in the present example).
Figure 9:
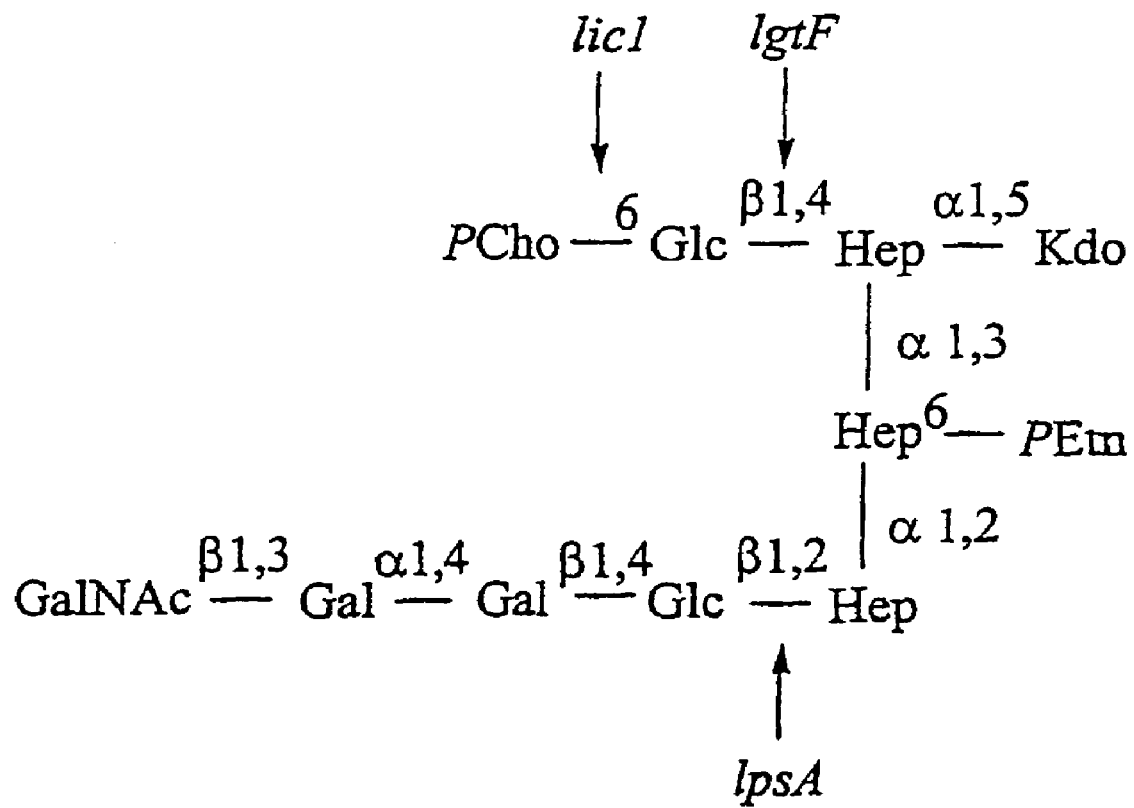
FIG. 9 illustrates the genes involved in chain extension from the LPS inner-core of *H. influenzae* strain Rd⁻. Genes orf3 and lic2b in the lic2 locus control chain extension from Hep II in type b strains: these genes are missing in strain Rd⁻. Lic1 controls incorporation of PCho.

Immunisation with Carbohydrate(CHO)-BSA Conjugate Followed by Non-conjugated CHO The LPS-OH from the previous example can be conjugated to BSA according to the procedure described in Gu et al., Infect.Immun. 64:4047-4053, 1996. Alternatively, it can be conjugated to BSA via the Kdo carboxyl group with $M_2C_2H$ (4(4-N-maleimidomethyl) cyclohexane 1-carboxyl hydrazide ½ dioxane) according to the procedure developed by Wei Zou of National Research Council of Canada as described in FIG. 8. In summary, LPS-OH was conjugated to BSA via selective activation of the Kdo carboxyl group with EDC and the use of the linker strategy shown in the above scheme.

Female BALB/c mice, 6-8 weeks of age, were immunised intraperitoneally with Rd lic11psA odA LPS-BSA conjugate. Each mouse received 2 μg of carbohydrate in 0.2 ml Ribis complete adjuvant (Cedarlane Laboratories Ltd, Hornby, ON) per injection. The mice were boosted on day 21 and 42 with an equivalent amount of conjugated vaccine. On day 137 the mice received a final ip injection containing 10 μg 1003 lic11psA odA LPS in Ribi and serum was collected on day 147.

Example 6

Preparation of Monoclonal Antibodies LLA4 and LLA5 to *Haemophilus influenzae* Strains Strains with defined mutations in the LPS biosynthetic machinery can be used to produce monoclonal antibodies (Mabs) to defined LPS oligosaccharide structures. Murine Mabs were raised against *H. influenzae* mutant strains containing the conserved inner-core moiety. For example, BALB/c mice were immunized with formalin-killed whole cells of Rd lic11psA. Initial ELISA screening against the homologous LPS and heterologous Rd LPS resulted in the establishment of 12 hybridomas. Following testing of the 12 MAbs against a panel of Rd mutant LPS, two MAbs, LLA5, $IgG_{2a}$ and LLA4, $IgG_{2b}$, were chosen for further testing.

LLA4 was found to recognize an inner core epitope present in the homologous strain. In ELISA testing, LLA5 showed cross reactivity with purified LPS from a majority strain from a genetically diverse culture collection (14 out of 25 non-typeable strain LPS) (Table 3). The epitope recognized by Mab LLA5 was present in the RdlpsA single mutant and in the more truncated RdliclorfH double mutant which lacks the HepIII residue (Table 4). The LLA5 epitope is not present in LPS from the single mutant, RdlgtF. As mentioned above the lgtF gene is required for addition of the β-D-Glc residue to the 4-position of HepI.

Surprisingly, a comparison of the LPS from the 25 strains by structural analysis techniques known in the art indicated that Mab LLA5 was detecting a lacto-N-neotetraose (LNnT)-containing oligosaccharide epitope arising from chain extension from the HepI unit of the inner core moiety. Strains that were not recognized by Mab LLA5 were characterized by the absense of the LNnT-containing chain extensions. *H. influenzae* strains that express the LNnT-containing chain extension only express it to a minor extent under standard laboratory growth conditions. It was not previously identified in strain Rd due to low expression levels (Risberg et al., Eur J. Biochem. 261:717-180, 1999). It has now been isolated and characterized by liberating the core oligosaccharide from the LPS of strain Rd (RM 118) by mild acid hydrolysis and separation on gel permeation chromatography on Biogel P-4 in the same fashion as in FIG. 14, procedures known to those skilled in the art. The LNnT-containing core oligosaccharide fraction elutes as a minor high molecular weight component labeled 'HMW-fraction'. This is a minor component compared to the larger peak (centered at 400) which comprised the major glycoforms identified for strain Rd (Risberg et al., Eur J. Biochem. 261:717-180, 1999). The HMW core oligosaccharide from strain Rd was characterized as having LNnT-containg chain extensions from HepI by tandem mass spectrometry (MS/MS) techniques (Thibault et al., Methods in Molecular Biology, Vol 145: Bacterial toxins: Methods and Protocols (Holst, O., ed.) pp 327-344, Humana Press, 1999 and references therein). The fragmentation pattern in the ESI-MS/MS was indicative of the presence of the LNnT oligosaccharide chain extension having the sequence Gal-GlcNAc-Gal-Glc and capped by the terminal sugar unit, PEtn-GalNAc (FIG. 1).

When strain Rd is grown in medium containing sialic acid, LPS glycoforms containing the sialylated oligosaccharides are expressed. Applicant has found sialalyl lactose having the structure α-Neu5Ac-(2→3)-β-D-Galp-(1→4)-β-D-Glc attached as an oligosaccharide extention from HepIII. Furthermore this oligosaccharide extention has been identified in several NTHi strains. The phase-variable gene, lic3A encodes the sialyltransferase that adds CMP-Neu5Ac to the lactose acceptor. Sialylated analogues of LNnT chain extentions are detectable in the LPS in strain Rd when the organism is grown under the conditions described. Sialylated LNnT oligosaccharide chain extentions from the inner-core LPS having the structure α-Neu5Ac-(2→3)-β-D-Galp-(1→4)-β-D-GlcpNAc-(1→3)-β-D-Galp-(1→4)-β-D-Glcp are readily detectable in the RdlgtClic3A double mutant by ES-MS of O-deacylated LPS. Applicant has confirmed the structure of LPS in the conserved inner core has sialylated LNnT-containing chain extensions using MS/MS techniques, high field nuclear magnetic resonance techniques, and methylation analysis, all of which are procedures of structural analysis known to those skilled in the art. Applicant has found that *H. influenzae* utilizes a block mechanism for adding the LNnT-containing oligosaccharide chain extensions which involves genes from the rfb locus. There is an absolute correlation between the presence of the rfb gene and LNnT formation in all Hi strains investigated.

LPS from the NTHi stains that are reactive with Mab LLA5 also show a high molecular weight (HMW) fraction in the gel permeation chromatograms after mild acid hydrolysis. For example, LPS from NTHi strain 285 shows the minor HMW fraction for which the presence of LNnT-containing chain extensions, also capped by a Petn-GalNAc unit, are Characterized from the MS/MS fragmentation pattern in the same fashion as shown in FIG. 1. Further confirmation for this LNnT-containing oligosaccharide chain extension was obtained from an MS/MS/MS experiment. No detectable HMW fraction is found in the mild acid hydrolysates of strains that are LLA5-nonreactive, for example NTHi strain 1247.

TABLE 1

Structures of the major LPS glycoforms of increasing oligosaccharide chain length from HepIII in mutant stains of *H. influenzae* RM118.

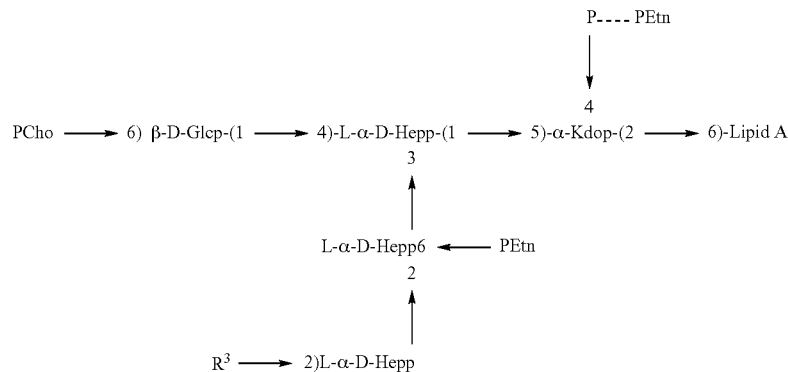

| Structure | Glycoform | Mutant Strain(s) | Substitution Pattern ($R^3$) |
|---|---|---|---|
| 3 | Hex1 | LpsA | H |
| 4 | Hex2 | lic2A | β-D-Glcp |
| 5 | Hex3 | lgtC, lgtD | β-D-Galp-(1 → 4)-β-D-Glcp |
| 6 | Hex4 | LgtD | α-D-Galp-(1 → 4)-β-D-Gal-(1 → 4)-β-D-Glc |

TABLE 2

LPS-related genes investigated in strain RM118 in this study. HI numbers are the ORF designations given by TIGR for the *H. influenzae* genome sequence data base. The genes given in bold are those selected for detailed comparative analysis of the expressed LPS glycoforms.

| Gene | HI number | Reference |
|---|---|---|
| kdtA | 0652 | 1 |
| lgtC | 0259 | 1 |
| lgtD | 1578 | 1 |
| lpsA | 0765 | 1 |
| orfZ | 0260.1 | 1 |
| opsX | 0261 | 1 |
| orfH | 0523 | 1 |
| rfaF | 1105 | 1 |
| lic2A | 0550 | 2 |
| lic1 | 1537-1540 | 3 |
| lgtF | 0653 | 4 |
| cld | 0866 | 1 |
| galU | 0812 | 1 |
| kfiC | 0868 | 1 |
| lsg1 | 0867 | 1 |
| orfM | 0260 | 1 |
| orfE | 0869 | 1 |
| orfO | 0870 | 1 |
| orfY | 0871 | 1 |
| pgmB | 0740 | 1 |
| pgmC | 1337 | 1 |
| rfe | 1716 | 1 |
| rfbP | 0872 | 1 |
| rfbB | 0873 | 1 |

1. Hood et al., Mol. Microbiol. 22:951-965, 1996
2. High et al, Mol. Microbiol. 9:1275-1282, 1993
3. Weiser et al., J. Bacteriol. 172:3304-3309, 1990
4. Applicant's study herein

TABLE 3

Rd lic1lpsA odA-BSA plus 1003 lic1lpsA odA LPS Day 147 sera & LLA5 MAb vs *Haemophilus* mutant & non-typable strain LPS

| Strains | EIA $OD_{410}$ | | |
|---|---|---|---|
| | serum #1 | serum #2 | LLA5 |
| 1003 lic1lpsA odA | 2.329 | 1.575 | — |
| Rd lic1lpsA odA | 0.746 | 0.742 | 1.414 |
| 1268 | 1.143 | 0.240 | 1.371 |
| 1247 | 0.571 | 0.250 | — |
| 1209 | 0.870 | 0.162 | 0.988 |
| 1233 | 0.436 | 0.135 | 1.451 |
| 1181 | 0.702 | 0.244 | 1.452 |
| 1232 | 0.568 | 0.270 | 1.661 |
| 981 | 0.474 | 0.182 | — |
| 486 | 0.512 | 0.287 | — |
| 1292 | 0.433 | 0.184 | 1.675 |
| 1008 | 0.830 | 0.172 | — |
| 1158 | 0.763 | 0.154 | — |
| 1124 | 0.524 | 0.127 | — |
| 1003 | 2.014 | 0.914 | — |
| 667 | 0.606 | 0.252 | 1.239 |
| 285 | 0.658 | 1.350 | 1.334 |
| 176 | 0.360 | 0.237 | 1.444 |
| 162 | 0.462 | 0.251 | 1.388 |
| 1180 | 0.974 | 0.254 | 1.464 |
| 1159 | 0.874 | 0.128 | — |
| 723 | >2.500 | 1.253 | — |
| 1231 | >2.500 | 1.008 | 1.404 |
| 1200 | 1.206 | 0.186 | 1.420 |
| 1207 | 0.667 | 0.137 | 1.040 |
| 432 | 0.530 | 0.159 | — |
| 375 wt | 1.860 | 0.946 | — |

TABLE 4

| mutant LPS | LLA5 Mab EIA OD$_{410}$ |
|---|---|
| Rd lic1lpsA odA | 0.889 |
| Rd lpsA | 1.630 |
| Rd lic1orfH | 1.216 |
| Rd lgtF | — |

TABLE 5

Negative ion ESI-MS data and proposed compositions of O-deacylated LPS from *H. influenzae* strain Rd and mutants. Average mass units were used for calculation of molecular weight based on proposed composition as follows: Lipid A-OH, 953.00; Hex, 162.15; HexNAc, 203.19; Hep, 192.17; Kdo-P, 300.16; PEtn, 123.05. PCho, 165.05

| Strain | Observed Ions (m/z) $(M-2H)^{2-}$ | $(M-3H)^{3-}$ | Molecular Mass (Da) Observed | Calculated | Relative Intensity[b] | Proposed Composition |
|---|---|---|---|---|---|---|
| OpsX[a] | 616.0 | — | 1234.0 | 1235.1 | 80.0 | Kdo-P, Lipid A-OH(—H$_2$O)[c] |
|  | 625.0 | — | 1252.0 | 1253.1 | 20.0 | Kdo-P, Lipid A-OH |
| RfaF | 721.6 | — | 1445.1 | 1445.3 | 100.0 | Hep, Kdo-P, Lipid A-OH |
| OrfH | 817.5 | — | 1637.5 | 1637.3 | 10.6 | 2Hep, Kdo-P, Lipid A-OH |
|  | 879.2 | — | 1760.4 | 1760.5 | 42.4 | 2Hep, PEtn, Kdo-P, Lipid A-OH |
|  | 940.5 | — | 1883.4 | 1883.6 | 15.2 | 2Hep, 2PEtn, Kdo-P, Lipid A-OH |
|  | 1042.3 | — | 2087.5 | 2087.7 | 21.2 | PCho, Hex, 2Hep, PEtn, Kdo-P, Lipid A-OH |
|  | 1104.8 | — | 2211.6 | 2210.8 | 10.6 | PCho, Hex, 2Hep, 2PEtn, Kdo-P, Lipid A-OH |
| LpsA | 1056.3 | — | 2114.7 | 2114.9 | 10.3 | Hex, 3Hep, PEtn, Kdo-P, Lipid A-OH |
|  | 1139.0 | 759.0 | 2280.1 | 2279.9 | 69.0 | PCho, Hex, 3Hep, PEtn, Kdo-P, Lipid A-OH |
|  | 1200.4 | 800.0 | 2403.0 | 2403.0 | 20.7 | PCho, Hex, 3Hep, 2PEtn, Kdo-P, Lipid A-OH |
| Lic2A | 1137.5 | 758.3 | 2277.1 | 2277.1 | 18.0 | 2Hex, 3Hep, PEtn, Kdo-P, Lipid A-OH |
|  | 1220.0 | 813.3 | 2442.5 | 2443.1 | 51.0 | PCho, 2Hex, 3Hep, PEtn, Kdo-P, Lipid A-OH |
|  | 1281.9 | 854.3 | 2565.8 | 2566.1 | 31.0 | PCho, 2Hex, 3Hep, 2PEtn, Kdo-P, Lipid A-OH |
| LgtC | 1301.1 | 867.1 | 2604.3 | 2604.3 | 80.0 | PCho, 3Hex, 3Hep, PEtn, Kdo-P, Lipid A-OH |
|  | 1362.7 | 908.2 | 2727.4 | 2727.3 | 20.0 | PCho, 3Hex, 3Hep, 2PEtn, Kdo-P, Lipid A-OH |
| LgtD | 1300.6 | 867.1 | 2603.9 | 2604.3 | 62.0 | PCho, 3Hex, 3Hep, PEtn, Kdo-P, Lipid A-OH |
|  | 1362.0 | — | 2726.0 | 2727.3 | 5.0 | PCho, 3Hex, 3Hep, 2PEtn, Kdo-P, Lipid A-OH |
|  | 1381.6 | 921.2 | 2765.5 | 2766.3 | 28.0 | PCho, 4Hex, 3Hep, PEtn, Kdo-P, Lipid A-OH |
|  | 1443.3 | 962.1 | 2888.9 | 2889.4 | 5.0 | PCho, 4Hex, 3Hep, 2PEtn, Kdo-P, Lipid A-OH |
| LgtF | 1137.4 | 757.8 | 2276.6 | 2277.1 | 18.0 | 2Hex, 3Hep, PEtn, Kdo-P, Lipid A-OH |
|  | 1218.6 | 812.2 | 2439.4 | 2439.2 | 18.0 | 3Hex, 3Hep, PEtn, Kdo-P, Lipid A-OH |
|  | 1280.0 | 853.2 | 2562.3 | 2562.3 | 10.0 | 3Hex, 3Hep, 2PEtn, Kdo-P, Lipid A-OH |
|  | 1320.3 | 879.9 | 2642.7 | 2642.3 | 38.0 | 3Hex, 3Hep, PEtn, P, Kdo-P, Lipid A-OH |
|  | — | 920.8 | 2765.3 | 2766.3 | 16.0 | HexNAc, 3Hex, 3Hep, 2PEtn, Kdo-P, Lipid A-OH |
| Lic1 | 1056.2 | — | 2114.3 | 2114.9 | 12.8 | Hex, 3Hep, PEtn, Kdo-P, Lipid A-OH |
|  | 1117.4 | 744.9 | 2237.2 | 2237.9 | 7.2 | Hex, 3Hep, 2PEtn, Kdo-P, Lipid A-OH |
|  | 1218.3 | 812.1 | 2439.3 | 2439.2 | 20.0 | 3Hex, 3Hep, PEtn, Kdo-P, Lipid A-OH |
|  | 1279.7 | 852.6 | 2561.1 | 2562.3 | 12.9 | 3Hex, 3Hep, 2PEtn, Kdo-P, Lipid A-OH |
|  | 1299.2 | 865.7 | 2600.3 | 2601.3 | 9.0 | 4Hex, 3Hep, PEtn, Kdo-P, Lipid A-OH |
|  | 1360.6 | 906.5 | 2722.8 | 2724.4 | 10.0 | 4Hex, 3Hep, 2PEtn, Kdo-P, Lipid A-OH |
|  | 1401.1 | 933.7 | 2804.3 | 2804.5 | 12.9 | HexNAc, 4Hex, 3Hep, PEtn, Kdo-P, Lipid A-OH |
|  | 1462.5 | 974.6 | 2927.0 | 2927.5 | 15.1 | HexNAc, 4Hex, 3Hep, 2PEtn, Kdo-P, Lipid A-OH |

[a]Data acquired by CE-ESI-MS on a crystal Model 310 CE instrument interfaced to an API 3000 triple quadrupole mass spectrometer (Perkin-Elmer/Sciex) fitted with a bare fused silica capillary column and using 30 mM morpholine-acetate (pH 9.0) containing 5% methanol as the separation buffer as described (30).
[b]Measured from the respective molecular ions in the reconstructed spectrum.
[c]The major ion observed corresponded to the molecular ion −18 (loss of H$_2$O).

TABLE 6

Linkage analysis data for LPS derived from *H. influenzae* RM118 mutated in LPS biosynthesis genes.

| Methylated Sugar[a] | $T_{gm}$[b] | orfH | lpsA | lic2A | lgtC | lgtD | lgtF | Linkage assignment |
|---|---|---|---|---|---|---|---|---|
| 2,3,4,6-Me$_4$-Glc | 1.00 | −tr[c] | 6.7 | 22.5 | tr | tr |  | D-Glcp-(1→ |
| 2,3,4,6-Me$_4$-Gal | 1.05 | −tr |  |  | 34.3 | 22.9 | 10.3 | D-Galp-(1→ |

TABLE 6-continued

Linkage analysis data for LPS derived from *H. influenzae* RM118 mutated in LPS biosynthesis genes.

| Methylated Sugar[a] | $T_{gm}$[b] | orfH | lpsA | lic2A | lgtC | lgtD | lgtF | Linkage assignment |
|---|---|---|---|---|---|---|---|---|
| 2,3,6-Me$_3$-Glc | 1.18 | −tr | | 6.3 | 33.0 | 24.4 | 18.8 | → 4)-D-Glcp-(1→ |
| 2,3,6-Me$_3$-Gal | 1.17 | | | | | 12.4 | 16.6 | → 4)-D-Galp-(1→ |
| 2,4,6-Me$_3$-Gald | 1.20 | 5.0 | 12.4 | 5.4 | tr | 4.0 | 10.3 | → 3)-D-Galp-(1→ |
| 2,3,4,6,7-Me$_5$-Hep | 1.30 | 27.4 | 35.4 | | | | | L,D-Hepp(1→ |
| 3,4,6,7-Me$_4$-Hep | 1.44 | | | 53.3 | 15.8 | 16.0 | 16.3 | → 2)-L,D-Hepp(1→ |
| 2,4,6,7-Me$_4$-Hep | 1.47 | 37.0 | | | | | 19.7 | → 3)-L,D-Hepp(1→ |
| 2,6,7-Me$_3$-Hep | 1.52 | 23.7 | 45.4 | 12.5 | 10.6 | 17.1 | | → 3,4)-L,D-Hepp-(1→ |
| 2,3,4,6-Me$_4$-GalN | 1.58 | | | | | | 8.0 | D-GalpNAc-1(1→ |

[a]2,3,4,6-Me$_4$-Glc represents 1,5-di-O-acetyl-2,3,4,6-tetra-O-methyl-D-glucitol-1-d$_1$, etc
[b]Retention times ($T_{gm}$) are reported relative to 2,3,4,6-Me$_4$-Glc and values are not corrected for differences in detector response factors.
[c]Trace amount detected.
[d]All samples showed detectable levels of 2,4,6,-Me$_3$-Gal.

TABLE 7

Negative ion ESI-MS data and proposed compositions for major glycoforms in O-deacylated LPS of NTHi strains 176, 486, 285 and 1158. An asterisk (*) indicates predominantions.

| Strain | (M-4H)$^{4-}$ | (M-3H)$^{3-}$ | Observed | Calculated[a] | Proposed Composition |
|---|---|---|---|---|---|
| 176 | 608.8 | 811.9 | 2439.2 | 2439.2 | Hex$_3$•Hep$_3$•PEtn$_1$•P$_1$•Kdo$_1$•Lipid A-OH |
| | 609.5 | 813.0 | 2442.0 | 2442.2 | PCho•Hex$_2$•Hep$_3$•PEtn$_1$•P$_1$•Kdo$_1$•Lipid A-OH |
| | 639.6 | 853.0 | 2562.4 | 2562.1 | Hex$_3$•Hep$_3$•PEtn$_2$•P$_1$•Kdo$_1$•Lipid A-OH |
| | 640.4 | 853.8 | 2565.6 | 2565.3 | PCho•Hex$_2$•Hep$_3$•PEtn$_2$•P$_1$•Kdo$_1$•Lipid A-OH |
| | 650.0 | 867.0 | 2604.0 | 2604.3 | PCho•Hex$_3$•Hep$_3$•PEtn$_1$•P$_1$•Kdo$_1$•Lipid A-OH |
| | 680.9* | 908.3 | 2727.6 | 2727.3 | PCho•Hex$_3$•Hep$_3$•PEtn$_2$•P$_1$•Kdo$_1$•Lipid A-OH |
| 486 | 690.4 | 920.8 | 2765.5 | 2766.4 | PCho•Hex$_4$•Hep$_3$•PEtn$_1$•P$_1$•Kdo$_1$•Lipid A-OH |
| | 721.2* | 961.8 | 2888.6 | 2889.5 | PCho•Hex$_4$•Hep$_3$•PEtn$_2$•P$_1$•Kdo$_1$•Lipid A-OH |
| | 763.2 | 1017.9 | 3056.8 | 3057.7 | Neu5Ac•PCho•Hex$_4$•Hep$_3$•PEtn$_1$•P$_1$•Kdo$_1$•LipidA-OH |
| | 793.9 | 1059.1 | 3180.0 | 3180.7 | Neu5Ac$_1$•PCho•Hex$_4$•Hep$_3$•PEtn$_2$•P$_1$•Kdo$_1$•LipidA-OH |
| 285 | 568.9 | 758.7 | 2279.5 | 2280.0 | PCho•Hex$_1$•Hep$_3$•PEtn$_1$•P$_1$•Kdo$_1$•Lipid A-OH |
| | 599.6* | 799.8 | 2402.3 | 2403.1 | PCho•Hex$_1$•Hep$_3$•PEtn$_2$•P$_1$•Kdo$_1$•Lipid A-OH |
| 1158 | 657.7 | 877.4* | 2634.8 | 2634.4 | PCho•Hex$_2$•Hep$_4$•PEtn$_1$•P$_1$•Kdo$_1$•LipidA-OH |
| | 688.6 | 918.3 | 2758.4 | 2757.4 | PCho•Hex$_2$•Hep$_4$•PEtn$_2$•P$_1$•Kdo$_1$•LipidA-OH |
| | 698.1 | 931.0 | 2796.4 | 2796.6 | PCho•Hex$_3$•Hep$_4$•PEtn$_1$•P$_1$•Kdo$_1$•LipidA-OH |
| | 699.0 | 932.5 | 2800.0 | 2799.5 | PCho$_2$•Hex$_2$•Hep$_4$•PEtn$_1$•P$_1$•Kdo$_1$•LipidA-OH |

[a]Average mass units were used in calculating molecular weights.

TABLE 8

Linkage analysis data for LPS from NTHi strains 176, 486, 1158, 285 and oligosaccharides derived from NTHi 176 LPS.

| | Relative detector response | | | | | | | |
|---|---|---|---|---|---|---|---|---|
| | NTHi strains | | | | NTHi 176 derived | | | |
| Methylated Sugar[a] | 176 | 486 | 285 | 1158 | LPS-P[b] | Fr.1[c] | Fr.2 | Fr.3 | Linkage assignment |
| 2,3,4,6-Me$_4$-Glc | 22 | 16 | | 7 | 13 | 15 | 26 | 32 | D-Glcp-(1→ |
| 2,3,4,6-Me$_4$-Gal | 17 | 16 | 2 | 8 | 10 | 16 | 22 | 18 | D-Galp-(1→ |
| 2,3,6-Me$_3$-Glc | 6 | 27 | | 15 | 14 | 7 | 2 | 15 | 4)-D-Glcp-(1→ |
| 2,3,6-Me$_3$-Gal | | | 2 | 6 | | 2 | | | 4)-D-Galp-(1→ |
| 2,4,6-Me$_3$-Gal | 5 | 7 | 1 | 5 | 1 | 13 | 3 | 2 | 3)-D-Galp-(1→ |
| 2,3,4-Me$_3$-Glc | | | 1 | 11 | 1 | 1 | | | 6)-D-Glcp-(1→ |
| 2,3,4-Me$_3$-Gal | | | | | | 6 | | | 6)-D-Galp-(1→ |
| 2,3,4,6-Me$_5$-Hep | | | | 11 | | 1 | | | D,D-Hepp-(1→ |
| 2,3,4,6,7-Me$_5$-Hep | 1 | | 52 | | 1 | | 5 | | L,D-Hepp-(1→ |
| 3,4,6,7-Me$_4$-Hep | 1 | | 4 | 13 | 12 | | | | 2)-L,D-Hepp-(1→ |
| 2,4,6,7-Me$_4$-Hep | 22 | 12 | | | 12 | 12 | 19 | 14 | 3)-L,D-Hepp-(1→ |
| 2,6,7-Me$_3$-Hep | 22 | 14 | 34 | 16 | 26 | 16 | 23 | 16 | 3,4)-L,D-Hepp-(1→ |
| 4,6,7-Me$_3$-Hep | 2 | 5 | | | 8 | 1 | | | 2,3)-L,D-Hepp-(1→ |

TABLE 8-continued

Linkage analysis data for LPS from NTHi strains 176, 486, 1158, 285 and oligosaccharides derived from NTHi 176 LPS.

| | Relative detector response | | | | | | | |
|---|---|---|---|---|---|---|---|---|
| | NTHi strains | | | | NTHi 176 derived | | | |
| Methylated Sugar[a] | 176 | 486 | 285 | 1158 | LPS-P[b] | Fr.1[c] | Fr.2 | Fr.3 | Linkage assignment |
| 2,3,6-Me$_4$-GlcN | | | | | | 6 | | | 4)-D-GlcpNAc-(1→ |
| 2,3,4-Me$_4$-GlcN | 2 | 2 | 4 | | | | | | 6)-D-GlcpNAc-(1→ |

[a]2,3,4,6-Me$_4$-Glc represents 1,5-di-O-acetyl-2,3,4,6-tetra-O-methyl-D-glucitol-1-d$_1$, etc
[b]LPS-P represents dephosphorylated LPS-OH
[c]Fr.1 represents high molecular weight sample (HMG) of NTHi 176 obtained after mild acid hydrolysis.

The invention claimed is:

1. An isolated lipopolysaccharide moiety consisting essentially of a triheptosyl inner-core moiety having the structure II:

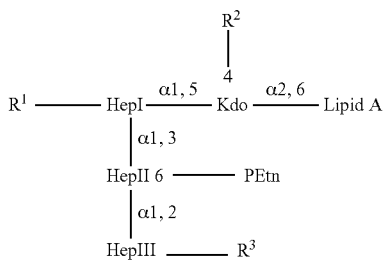

wherein $R^1$ is hydrogen, β-D-Glcp(1→4), or PCho→6)-β-D-Glcp(1→4);

$R^2$ is phosphate (P) or pyrophosphoethanolamine (P-PEtn);

$R^3$ is hydrogen, β-D-Glcp or β-D-Galp, and when $R^1$ is hydrogen or β-D-Glcp(1→4), then $R^3$ may also be β-D-Galp-(1→4)-β-D-Glcp, α-D-Galp-(1→4)-β-D-Galp-(1→4)-β-D-Glcp, β-D-GalpNAc-(1→3)-α-D-Galp-(1→4)-β-D-Galp-(1→4)-β-D-Glcp, or α-NeuAc(2→3)-β-D-Galp-(1→4)-β-D-Glcp-(1→3), wherein $R^3$ is attached at either the O-3 or O-2 position of HepIII;

Kdo is 3-deoxy-D-manno-2-octulosonic acid; and

Lipid A is detoxified.

2. A composition comprising the lipopolysaccharide moiety of claim 1 together with a pharmaceutically acceptable carrier.

3. The composition of claim 2 wherein the pharmaceutically acceptable carrier is immunogenic.

4. Method of treating a disease caused by infection with Haemophilus influenzae comprising administering the composition of claim 2 to a subject in need of such treatment.

5. The method according to claim 4, wherein the Haemophilus influenzae is non-typeable Haemophilus influenzae.

6. The method according to claim 4 wherein the disease is selected from the group consisting of otitis media, meningitis, pneumonia, and respiratory tract infection.

7. A process for preparing a lipopolysaccharide moiety consisting essentially of a conserved triheptosyl inner-core moiety having the structure II:

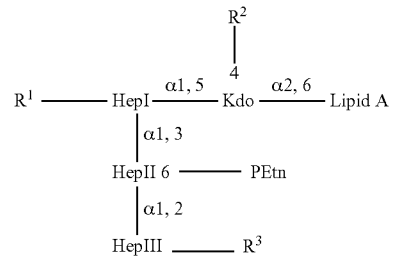

wherein $R^1$ is hydrogen, β-D-Glcp(1→4), or PCho→6)-β-D-Glcp(1→4);

$R^2$ is phosphate (P) or pyrophosphoethanolamine (P-PEtn);

$R^3$ is hydrogen, β-D-Glcp, β-D-Galp, β-D-Galp-(1→4)-β-D-Glcp,

α-D-Galp-(1→4)-β-D-Galp-(1→4)-β-D-Glcp, and when $R^1$ is hydrogen or β-D-Glcp(1→4), then $R^3$ may also be β-D-GalpNAc-(1→3)-α-D-Galp-(1→4)-β-D-Galp-(1→4)-β-D-Glcp, or α-NeuAc(2→3)-β-D-Galp-(1→4)-β-D-Glcp-(1→3), wherein $R^3$ is attached at either the O-3 or O-2 position of HepIII; and Kdo is 3-deoxy-D-manno-2-octulosonic acid; said process comprising:

transforming a recipient Haemophilus influenzae bacterial strain with one or more inactivated genes selected from the group consisting of lpsA, lic1, lic2, lic2A, lic2orf3, lic2B, lic3A, lgtC, lgtD, and lgtF;

culturing the transformed Haemophilus influenzae bacterial strain under conditions suitable for expressing the lipopolysaccharide moiety;

isolating the lipopolysaccharide moiety; and detoxifying the Lipid A portion of the lipopolysaccharide moiety.

8. The process according to claim 7 wherein the Haemophilus influenzae is non-typeable Haemophilus influenzae.

9. The process of claim 7, further comprising identifying the lipopolysaccharide moiety by contacting the lipopolysaccharide moiety with a monoclonal antibody specific for an epitope expressed following inactivation of one or more genes selected from the group consisting of lpsA, lic1, lic2, lic2A, lic2orf3, lic2B, lic3A, lgtC, lgtD, lgtF, rfaF and orfH.

10. The process of claim 9 comprising the monoclonal antibody that binds to the conserved triheptosyl inner-core moiety of claim 1.

11. A glycoconjugate comprising:
the lipopolysaccharide moiety according to claim 1 and an immunogenic carrier cross-linked to the lipopolysaccharide moiety.

12. The glycoconjugate according to claim 11 wherein the lipopolysaccharide moiety and the immunogenic carrier are cross-linked with a linker molecule.

13. The glycoconjugate of claim 11 wherein the linker molecule is selected from the group consisting of adipic acid dihydrazide, epsilon.aminohexanoic acid, chlorohexanol dimethyl acetal, D-glucuronolactone and p-nitrophenylamine.

14. The glycoconjugate of claim 11 wherein the carrier is tetanus toxoid (TT) or nontypeable *Haemophilus influenzae* high-molecular-weight protein (NTHi HMP).

15. An immunogenic composition for raising an immune response against nontypeable *Haemophilus influenzae* infection in a subject, said composition comprising one or more glyconjugates of claim 11 and an adjuvant.

16. The immunogenic composition of claim 15, wherein the composition is formulated as a liposome.

* * * * *